United States Patent
Yu et al.

(10) Patent No.: US 11,680,298 B2
(45) Date of Patent: Jun. 20, 2023

(54) METHOD OF IDENTIFYING RISK OF CANCER AND THERAPEUTIC OPTIONS

(71) Applicants: Agency for Science, Technology and Research, Singapore (SG); Tan Tock Seng Hospital Pte. Ltd., Singapore (SG)

(72) Inventors: Qiang Yu, Singapore (SG); Jian Yuan Goh, Singapore (SG); Min Feng, Singapore (SG); Ern Yu Tan, Singapore (SG)

(73) Assignees: Agency for Science, Technology and Research, Singapore (SG); Tan Tock Seng Hospital Pte. Ltd., Singapore (SG)

(*) Notice: Subject to any disclaimer, the term of this patent is extended or adjusted under 35 U.S.C. 154(b) by 528 days.

(21) Appl. No.: 16/331,072

(22) PCT Filed: Sep. 7, 2017

(86) PCT No.: PCT/SG2017/050448
§ 371 (c)(1),
(2) Date: Mar. 6, 2019

(87) PCT Pub. No.: WO2018/048354
PCT Pub. Date: Mar. 15, 2018

(65) Prior Publication Data
US 2019/0367991 A1     Dec. 5, 2019

(30) Foreign Application Priority Data

Sep. 7, 2016  (SG) ............................. 10201607451Y
Jun. 19, 2017 (SG) ............................. 10201705058S

(51) Int. Cl.
C12Q 1/68       (2018.01)
C12Q 1/6886     (2018.01)
A61K 31/519     (2006.01)

(52) U.S. Cl.
CPC .......... *C12Q 1/6886* (2013.01); *A61K 31/519* (2013.01); *C12Q 2600/112* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 2009/0298054 A1* | 12/2009 | Lesche | C12Q 1/6886 435/6.12 |
| 2011/0104062 A1 | 5/2011 | Siu et al. | |
| 2011/0123990 A1 | 5/2011 | Baker et al. | |
| 2013/0059746 A1 | 3/2013 | Shaughnessy, Jr. et al. | |
| 2013/0280264 A1 | 10/2013 | Davila et al. | |
| 2014/0065620 A1 | 3/2014 | Perez et al. | |

FOREIGN PATENT DOCUMENTS

| | | | |
|---|---|---|---|
| CN | 104293788 A | 1/2015 | |
| WO | WO-2005123945 A2 * | 12/2005 | ........... C12Q 1/6886 |
| WO | WO 2008/057545 A2 | 5/2008 | |
| WO | WO-2016149350 A1 * | 9/2016 | ........... C12Q 1/6886 |
| WO | WO 2017/069710 A1 | 4/2017 | |

OTHER PUBLICATIONS

Carrasco et al. High-resolution genomic profiles define distinct clinic-pathogenetic subgroups of multiple myeloma patients. Cancer Cell;2006;9:313-325. (Year: 2006).*
Carrasco et al. High-resolution genomic profiles define distinct clinic-pathogenetic subgroups of multiple myeloma patients. Cancer Cell;2006;9:313-325. Supplemental data. (Year: 2006).*
Wee et al. IRAK1 is a therapeutic target that drives breast cancer metastasis and resistance to paclitaxel. Nature Communications, 2015;6: pp. 8746: 1-15. (Year: 2015).*
Cleary et al. Pacritinib, a Dual FL T3/JAK2 Inhibitor, Reduces Irak-1 Signaling in Acute Myeloid Leukemia. Blood;2015;126;23:p. 570. (Year: 2015).*
Chen et al. S100 protein family in human cancer. Am J Cancer Res; 2014;4(2):89-115. (Year: 2014).*
Huang et al. A preliminary study of concurrent gains and losses across gene expression profiles and comparative genomic hybridization in Taiwanese breast cancer patients. Transl Cancer Res; 2013;2(1):18-24. (Year: 2013).*
Singer et al. Comprehensive kinase profile of pacritinib, a nonmyelosuppressive Janus kinase 2 inhibitor. Journal of Experimental Pharmacology; Aug. 2016; 8: 11-19. (Year: 2016).*
Crusz and Balkwill. Inflammation and cancer: advances and new agents. Nat. Rev. Clin. Oncol.; 2015;12: p. 584-596. (Year: 2015).*
Ballout et al. Thymoquinone-based nanotechnology for cancer therapy: promises and challenges. Drug Discovery Today; 2018; 23; 5: p. 1089-1098. (Year: 2018).*

(Continued)

*Primary Examiner* — Juliet C Switzer
(74) *Attorney, Agent, or Firm* — Wolf, Greenfield & Sacks, P.C.

(57) ABSTRACT

There is provided a method of identifying risk of cancer in a human subject, the method comprising: determining in a biological sample of the subject, whether a copy number amplification of at least one continuous genomic region specific to human chromosome 1q21 is present, wherein the presence of a copy number amplification of the region specific to human chromosome 1q21 represents an elevated risk of cancer in the subject and the at least one continuous genomic region is selected from the group consisting of: a human TUFT1 gene or a gene from the human S100 family. It is also provided a method of treating cancer in a subject determined to have a copy number amplification of a region specific to human chromosome 1q21, the method comprising administering a therapeutic agent capable of suppressing IRAK1, IRAK4 or a S100 family member, such as Pacritinib. There are also provided a method of treating cancer, related polynucleotides, kits, therapeutic agents and use of the therapeutic agents.

11 Claims, 23 Drawing Sheets
Specification includes a Sequence Listing.

(56) References Cited

OTHER PUBLICATIONS

Khan et al. Thymoquinone, as an anticancer molecule: from basic research to clinical investigation Oncotarget; 2017; 8; 31: p. 51907-51919. (Year: 2017).*
Heizmann and Fritz. Handbook of Cell Signaling; 2010; Handbook of Cell Signaling; Three-Volume Set 2 ed: p. 983-993. (Year: 2010).*
Carrasco et al. Cancer Cell; 2006; 9;4:313-325. (Year: 2006).*
Carrasco et al., Cancer Cell; 2006; 9;4:313-325. Supplemental data. (Year: 2006).*
Silva et al. Cross-species DNA copy number analyses identifies multiple1q21-q23 subtype-specific driver genes for breast cancer. Breast Cancer Res Treat; 2015: 1-10. (Year: 2015).*
Page et al. Detection of HER2 amplification in circulating free DNA in patients with breast cancer; British Journal of Cancer; 2011; 104: 1342-1348. (Year: 2011).*
Zheng et al. Wild-Type N-Ras, Overexpressed in Basal-like Breast Cancer, Promotes Tumor Formation by Inducing IL-8 Secretion via JAK2 Activation. Cell Reports; 2015; 12: 511-524. (Year: 2015).*
Silva et al. Breast Cancer Res Treat; 2015: 1-10. (Year: 2015).*
Zheng et al. Cell Reports; 2015; 12: 511-524. (Year: 2015).*
Hojjat-Farsangi, J Drug Target; 2016; 24(3): 192-211 (published online on Jul. 27, 2015). (Year: 2016).*
Weigman et al. Breast Cancer Res Treat (2012) 133:865-880. (Year: 2012).*
McKiernan et al. Tumor Biol.; 2011; 32:441-450. (Year: 2011).*
Rodriguex-Barrueco et al. Genes& Development; 2015; 29:1631-1648. (Year: 2015).*
International Search Report and Written Opinion for International Application No. PCT/SG2017/050448 dated Dec. 8, 2017.
Acharyya et al., A CXCL1 paracrine network links cancer chemoresistance and metastasis. Cell. Jul. 6, 2012;150(1):165-78. doi: 10.1016/j.cell.2012.04.042. PubMed PMID: 22770218; PubMed Central PMCID: PMC3528019.
Beck et al., Next generation sequencing of serum circulating nucleic acids from patients with invasive ductal breast cancer reveals differences to healthy and nonmalignant controls. Mol Cancer Res. Mar. 2010;8(3):335-42. doi: 10.1158/1541-7786.MCR-09-0314. Epub Mar. 9, 2010. PubMed PMID: 20215424.
Carrasco et al., High-resolution genomic profiles define distinct clinico-pathogenetic subgroups of multiple myeloma patients. Cancer Cell. Apr. 2006;9(4):313-25. PubMed PMID: 16616336.

Chen et al., Chromosome 1q21 amplification and oncogenes in hepatocellular carcinoma. Acta Pharmacol Sin. Sep. 2010;31(9):1165-71. doi: 10.1038/aps.2010.94. Epub Aug. 2, 2010. Review. PubMed PMID: 20676120; PubMed Central PMCID: PMC4002324.
Cleary et al., Pacritinib, a dual FLT3/JAK2 inhibitor, reduces irak-1 signaling in acute myeloid leukemia. Blood. Dec. 3, 2015;126(23):570.
Crowley et al., Liquid biopsy: monitoring cancer-genetics in the blood. Nat Rev Clin Oncol. Aug. 2013;10(8):472-84. doi: 10.1038/nrclinonc.2013.110. Epub Jul. 9, 2013. Review. PubMed PMID: 23836314.
Dawson et al., Analysis of circulating tumor DNA to monitor metastatic breast cancer. N Engl J Med. Mar. 28, 2013;368(13):1199-209. doi: 10.1056/NEJMoa1213261. Epub Mar. 13, 2013. PubMed PMID: 23484797.
Goh et al., Chromosome 1q21.3 amplification is a trackable biomarker and actionable target for breast cancer recurrence. Nat Med. Nov. 2017;23(11):1319-1330. doi: 10.1038/nm.4405. Epub Sep. 25, 2017. PubMed PMID: 28967919.
Huang et al., A preliminary study of concurrent gains and losses across gene expression profiles and comparative genomic hybridization in Taiwanese breast cancer patients. Transl Cancer Res. Feb. 2013;2(1):18-24. doi: 10.3978/J.ISSN.2218-676X.2013.02.07.
Kulski et al., Genomic and phylogenetic analysis of the S100A7 (Psoriasin) gene duplications within the region of the S100 gene cluster on human chromosome 1q21. J Mol Evol. Apr. 2003;56(4):397-406. PubMed PMID: 12664160.
Ma et al., Isolation and characterization of a novel oncogene, amplified in liver cancer 1, within a commonly amplified region at 1q21 in hepatocellular carcinoma. Hepatology. Feb. 2008;47(2):503-10. PubMed PMID: 18023026.
Wee et al., IRAK1 is a therapeutic target that drives breast cancer metastasis and resistance to paclitaxel. Nat Commun. Oct. 27, 2015;6:8746. doi: 10.1038/ncomms9746. Erratum in: Nat Commun. 2015;6:10054. Yi, Bao [Corrected to Bao, Yi], PubMed PMID: 26503059; PubMed Central PMCID: PMC4640083.
Yu et al. The amplification of 1q21 is an adverse prognostic factor in patients with multiple myeloma in a Chinese population. Onco Targets Ther. Jan. 12, 2016;9:295-302. doi: 10.2147/OTT.S95381. eCollection 2016. PubMed PMID: 26834489; PubMed Central PMCID: PMC4716762.
Singaporean Search Report and Written Opinion for 11201901466P dated Nov. 19, 2020.
Silva et al., Cross-species DNA copy number analyses identifies multiple 1q21-q23 subtype-specific driver genes for breast cancer. Breast Cancer Res Treat. Jul. 2015;152(2):347-56. doi: 10.1007/s10549-015-3476-2. Epub Jun. 25, 2015.

* cited by examiner

METHOD OF IDENTIFYING RISK OF CANCER AND THERAPEUTIC OPTIONS

RELATED APPLICATIONS

This application is a national stage filing under 35 U.S.C. § 371 of International Application Number PCT/SG2017/050448, filed Sep. 7, 2017, which claims the benefit of Singapore Application Number 10201607451Y, filed Sep. 7, 2016, and Singapore Application Number 10201705058S, filed Jun. 19, 2017, each of which is herein incorporated by reference in its entirety.

TECHNICAL FIELD

Various embodiments disclosed herein relate broadly to a method of identifying risk of cancer, a method of treating cancer, related polynucleotides, kits, therapeutic agents and use of the therapeutic agents.

BACKGROUND

Cancer is one of the most common causes of death worldwide. Despite advances in therapies for cancer, numerous patients still develop recurrence and die of metastasis years after treatment. Tumour relapse and metastasis remain the primary causes of poor survival rates in cancer patients. However, molecular driver events leading to tumour recurrence and metastasis remain elusive.

Cancer patients show varied responses towards conventional cancer therapy such as chemotherapy and radiotherapy. This may be attributed to tumour heterogeneity, where cancer cells within bulk tumours display different phenotypic properties due to intrinsic genetic and epigenetic differences. Chemoresistance and radiotherapy resistance, as well as metastasis, may be particularly attributed to a distinct and aggressive subpopulation of cancer cells, known as tumour initiating cells (TICs) or cancer stem cells (CSCs), which possess "stem-like" characteristics. While majority of cancer cells can be killed by chemotherapy treatment, TICs are chemoresistant and are thus left behind and allowed to re-populate, resulting in cancer relapse. In addition, circulating TICs may contribute to micrometastasis, or minimal residual disease, which presence cannot be detected by conventional imaging and laboratory test.

Personalized therapy, which seeks to overcome the limitations of standard cancer therapy, requires the identification of new genes and biomarkers specific to disease subtypes and individual patients. As tumours may exhibit a high degree of intra- and inter-tumour heterogeneity, current methods have to rely on deep sequencing or next-generation sequencing (NGS) of primary tumours to identify somatic genetic mutation for personalized assay development.

However, the current NGS-based method has certain shortcomings. In addition to the high cost associated with the assay development, sequencing a part of the primary tumour only provides a snapshot view of the tumour which may not be reflective of the entire genomic landscape of the tumour due to intra-tumour heterogeneity. Furthermore, tumour associated mutations may be lost during tumour evolution or response to drug selection since malignant tumours tend to develop different driver mutations to adapt to the new microenvironment for metastatic spread. Therefore, the NGS-based method involving specific mutation tracking based on primary tumours, may not target evolved subclones and may misrepresent the actual tumour burden in the disease progression of a cancer patient. In addition, the NGS-based method also lacks prognostic value at the time of diagnosis.

In view of the above, there is thus a need to address or at least ameliorate one of the above problems.

SUMMARY

In one aspect, there is provided a method of identifying risk of cancer in a human subject, the method comprising:
 determining in a biological sample of the subject, whether a copy number amplification of a region specific to human chromosome 1q21 is present,
 wherein the presence of a copy number amplification of the region specific to human chromosome 1q21 represents an elevated risk of cancer in the subject.

In one embodiment, the determining step comprises determining whether a copy number amplification of at least one continuous genomic region located on human chromosome 1q21 is present.

In one embodiment, the determining step comprises evaluating a copy number ratio of the at least one continuous genomic region in the subject to a reference continuous genomic region in the subject, wherein a copy number ratio exceeding a threshold value is indicative of a copy number amplification.

In one embodiment, the threshold value is obtained by evaluating a copy number ratio of the at least one continuous genomic region in a healthy subject to a reference continuous genomic region in the healthy subject.

In one embodiment, said evaluating a copy number ratio of the at least one continuous genomic region comprises evaluating an average copy number ratio of at least two continuous genomic regions located on human chromosome 1q21 and wherein said evaluating an average copy number comprises:
 obtaining a copy number ratio of each of the at least two continuous genomic regions; and
 averaging the copy number ratios of the at least two continuous genomic regions to obtain an average copy number ratio.

In one embodiment, the threshold value is obtained by evaluating a mean copy number ratio of the at least one continuous genomic region located on human chromosome 1q21 based on two or more healthy reference subjects and wherein said evaluating a mean copy number ratio based on two or more healthy reference subjects comprises:
 evaluating a copy number ratio of the at least one continuous genomic region of a first healthy reference subject;
 evaluating a copy number ratio of the at least one continuous genomic region of a second healthy reference subject;
 optionally evaluating a copy number ratio of the at least one continuous genomic region of one or more subsequent healthy reference subject to obtain one or more subsequent copy number ratios; and
 adding the copy number ratios of the two or more healthy reference subjects; and
 computing a mean of the copy number ratios.

In one embodiment, the at least one continuous genomic region is selected from the group consisting of: a human TUFT1 gene, a gene from the human S100 family and combinations thereof.

In one embodiment, the determining step comprises performing an assay selected from the group consisting of: Next-Generation Sequencing (NGS), Comparative Genome Hybridization (CGH), Array Comparative Genome Hybridization (aCGH), Fluorescence in situ Hybridization (FISH), digital PCR (dPCR) and quantitative real-time PCR (qPCR).

In one embodiment, the biological sample is a fluid biological sample selected from the group consisting of: blood, plasma, serum and combinations thereof.

In one embodiment, the determining step comprises determining whether a copy number amplification is present in a cell free DNA.

In one embodiment, said risk of cancer is at least one of a risk of occurrence of cancer, a risk of recurrence of cancer, a risk of metastasis of cancer, a risk of non-abatement of cancer, or a risk of cancer-based mortality.

In one embodiment, the method further comprises stratifying the subject for treatment with a cancer therapy if a copy number amplification of the region specific to human chromosome 1q21 is present.

In one embodiment, the therapy comprises administering to the subject a therapeutic agent capable of suppressing interleukin-1 receptor-associated kinase 1 (IRAK1), interleukin-1 receptor-associated kinase 4 (IRAK4) or a S100 family member.

In one aspect, there is provided a method of treating cancer in a subject, the method comprising:
administering to the subject a therapeutic agent capable of suppressing IRAK1, IRAK4 or a S100 family member,
wherein the subject has, or is determined to have in his/her biological sample, a copy number amplification of a region specific to human chromosome 1q21.

In one embodiment, the method is independent of the expression or activity of the following selected from the group consisting of: tyrosine kinase, Janus kinase 2 (JAK2), JAK2V61F, signal transducer and activator of transcription 3 (STAT3), FMS-like tyrosine kinase 3 (FLT3), colony stimulating factor 1 receptor (CSF1R), tyrosine kinase non receptor 1, ROS1 and combinations thereof in the subject.

In one aspect, there is provided a therapeutic agent capable of suppressing IRAK1, IRAK4 or a S100 family member for use in treating cancer in a subject who has, or is determined to have in his/her biological sample, a copy number amplification of a region specific to human chromosome 1q21.

In one aspect, there is provided use of a therapeutic agent capable of suppressing IRAK1, IRAK4 or a S100 family member in the manufacture of a medicament for treating cancer in a subject, wherein the subject has, or is determined to have in his/her biological sample, a copy number amplification of a region specific to human chromosome 1q21.

In one embodiment, the therapeutic agent comprises at least one of pacritinib, thymoquinone, a compound having the chemical formula

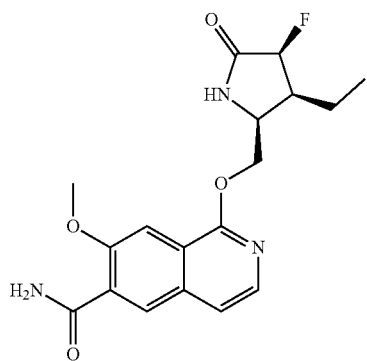 [SMILES: CC[C@@H]1[C@H](F)C(=O)N[C@@H]1COc1nccc2cc(C(N)=O)c(OC)cc12]

or therapeutically effective analogs thereof.

In one embodiment, the subject was previously ineffectively treated for cancer by an earlier therapy.

In one embodiment, the earlier therapy is different from a therapy using the therapeutic agent.

In one embodiment, the cancer is selected from the group consisting of neuroendocrine prostate cancer (NEPC), pancreatic cancer, uterine sarcoma, uterine cancer, ovarian cancer, liver cancer, lung cancer, breast cancer, bile duct cancer, cholangiocarcinoma, bladder cancer, sarcoma, esophagus cancer, prostate cancer, lung squamous cell carcinoma, stomach cancer, adenoid cystic carcinoma (ACC), pheochromocytoma and paraganglioma (PCPG), adenoid cystic carcinoma (ACyC), cervical cancer, melanoma, diffuse large B-cell lymphoma (DLBCL), head and neck cancer, mesothelioma, glioblastoma (GBM) and combinations thereof.

In one embodiment, the cancer comprises breast cancer or lung cancer.

In one aspect, there is provided an isolated polynucleotide comprising a nucleic acid sequence having a copy number amplification of a region specific to human chromosome 1q21.

In one aspect, there is provided a kit for determining whether a copy number amplification of a region specific to human chromosome 1q21 is present in a biological sample, the kit comprising:
one or more oligonucleotides for hybridizing to the region specific to human chromosome 1q21; and
instruction on using the oligonucleotides to determine whether a copy number amplification of the region specific to human chromosome 1q21 is present in the biological sample.

In one embodiment, the one or more oligonucleotides comprises a primer for amplifying at least one continuous genomic region located on human chromosome 1q21.

In one embodiment, the at least one continuous genomic region is selected from the group consisting of: a human TUFT1 gene, a gene from the human S100 family, a human RPP30 gene and combinations thereof.

In one embodiment, the one or more oligonucleotides comprise a hydrolysis probe.

In one embodiment, the one or more oligonucleotides comprise a sequence selected from the group consisting of:

TTTTAATCAGAGGGTGAGGGTGAT; (SEQ ID NO. 1)

GCTTCTCAATGTTGGAGGATACA; (SEQ ID No. 2)

GTCAAGATTGAGGAGGAAGAAGC; (SEQ ID No. 3)

TTCATAGATGGCTATGCCTCGG; (SEQ ID No. 4)

GGTGTTTCCCCACTAGCCA; (SEQ ID No. 5)

CCCAGAGAGTGTATTGGCCC; (SEQ ID No. 6)

TGCTATGTGGCCTTGGACAGATCACC; (SEQ ID No. 7)

AGTTTAAAGATCTCAGAGAGAGCCGAGGCA; (SEQ ID No. 8)

CCTTAGCGTATCACATGTGGACATGGACA; (SEQ ID No. 9)

-continued

GTTAGAGAGTCTCCAGGCCC;                (SEQ ID No. 10)

ACTGTAATCCAGCAAAAGCGG;               (SEQ ID No. 11)

TGTCCACAGACTTTCTCAAAAGATAGGGCC;      (SEQ ID No. 12)

and combinations thereof.

In one embodiment, the method or the kit has a sensitivity of no less than 85% and a specificity of no less than 85% in detecting a copy number amplification of a region specific to human chromosome 1q21.

In one embodiment, the human chromosome 1q21 comprises a region spanning from human chromosome chr1q21.1 to chr1q21.3.

DEFINITIONS

The term "region specific to" as used herein in reference to a chromosome or a chromosome locus refers to deoxyribonucleic acid (DNA) segments therein that are capable of distinguishing the chromosome or the chromosome locus from other chromosomes or the chromosome loci. For example, it may refer to DNA segments therein that are unique to that specific chromosome or that specific chromosome locus. A "region specific to" a chromosome or a chromosome locus is not limited to one continuous DNA segment within the chromosome or the chromosome locus, and includes a plurality of separate DNA segments within the chromosome or the chromosome locus, which in totality, are unique to the chromosome or the chromosome locus. In the practical sense, a "region specific to" a chromosome or a chromosome locus may be understood as DNA segments therein that can function as targets for probes that are preferential to the chromosome or the chromosome locus as compared to other chromosomes or chromosome loci. A "region" is not limited to the coding segments of a gene and therefore a "region specific to" a chromosome or a chromosome locus does not necessarily have to contain a gene. Accordingly, a "region" may contain non-coding segments. Further, a "region" as used herein in reference to a chromosome or a chromosome locus is not limited to a part of the chromosome or the chromosome locus and is intended to cover also the whole of the chromosome or the chromosome locus.

The term "copy number amplification" which is used interchangably with "copy number gain" herein, refers to an increase in the number of copies of a nucleic acid sequence, a chromosome region, a continuous genomic region or a gene in a sample such as a test sample as compared to a control/reference sample. A "copy number amplification" may result from a multiplication of a nucleic acid sequence, a chromosome region, a continuous genomic region or a gene, or it may result from translocation or aneuploidy.

"Determining a copy number amplification" as used herein includes direct and indirect means of determining whether there is an increase in copy number of a nucleic acid sequence, a chromosome region, a continuous genomic region or a gene. For example, a copy number amplification of a chromosome region may be directly detected by DNA sequencing methods or by performing a quantitative real-time polymerase chain reaction (qPCR) analysis of one or more continuous genomic regions such as genes located on the chromosome region or it may be indirectly detected through determination of downstream events such as the presence/level of corresponding ribonucleic acid (RNA) transcripts and/or protein expression.

The term "amplifying", when associated with the use of an oligonucleotide or a primer, refers to a process whereby one or more copies of a particular nucleic acid sequence, which may be a gene, is generated from a nucleic acid template sequence, preferably by the method of polymerase chain reaction (PCR). Other methods of amplification include, but are not limited to, ligase chain reaction (LCR), polynucleotide-specific based amplification (NSBA), or any other methods known in the art.

The term "threshold value" as used herein refers to any number that is used as a cutoff to characterize a sample such as a test sample as having a copy number amplification of a nucleic acid sequence, a chromosome region, a continuous genomic region or a gene. In certain embodiments, a "threshold value" is calculated using data associated with normal tissue samples (as opposed to tumour tissue samples), and/or tissue samples of healthy subjects. If, in relation to a test sample, the same type of data exceeds the "threshold value", the test sample can be considered to have a copy number amplification of the nucleic acid sequence, the chromosome region, the continuous genomic region or the gene.

The terms "coding sequences" and "coding region" as used herein refer to nucleotide sequences and nucleic acid sequences, including both RNA and DNA, that encode genetic information for the synthesis of an RNA, a protein, or any portion of an RNA or protein. Conversely, the terms "non-coding sequences" and "non-coding region" as used herein refer to nucleotide sequences and nucleic acid sequences that do not encode genetic information for the synthesis of an RNA, a protein, or any portion of an RNA or protein.

The term "expressed" or "expression" as used herein refers to the transcription from a gene to give an RNA nucleic acid molecule at least complementary in part to a region of one of the two nucleic acid strands of the gene. The term "expressed" or "expression" as used herein can also refer to the translation of RNA to produce a protein or peptide. As such, determining an "expression" of a gene includes determining an amount or an activity of the RNA nucleic acid molecule thereof or the protein or peptide thereof.

The term "isolated" as used herein means the removal of a nucleic acid or polynucelotide from its natural environment. An "isolated" nucleic acid or polynucelotide is typically partially purified.

The term "biological fluid" herein refers to a liquid taken from a biological source and includes, for example, blood, serum, plasma, sputum, lavage fluid, cerebrospinal fluid, urine, semen, sweat, tears, saliva, and the like. As used herein, the terms "blood," "plasma" and "serum" encompass fractions or processed portions thereof. Similarly, where a sample is taken from a biopsy, swab, smear, etc., the "sample" encompass a processed fraction or portion derived from the biopsy, swab, smear, etc.

The term "and/or", e.g., "X and/or Y" is understood to mean either "X and Y" or "X or Y" and should be taken to provide explicit support for both meanings or for either meaning.

The terms "coupled" or "connected" when used in this description are intended to cover both directly connected or connected through one or more intermediate means, unless otherwise stated.

The term "associated with", used herein when referring to two elements refers to a broad relationship between the two elements. The relationship includes, but is not limited to a physical, a chemical or a biological relationship. For example, when element A is associated with element B, elements A and B may be directly or indirectly attached to each other or element A may contain element B or vice versa.

Further, in the description herein, the word "substantially" whenever used is understood to include, but not restricted to, "entirely" or "completely" and the like. In addition, terms such as "comprising", "comprise", and the like whenever used, are intended to be non-restricting descriptive language in that they broadly include elements/components recited after such terms, in addition to other components not explicitly recited. Further, terms such as "about", "approximately" and the like whenever used, typically means a reasonable variation, for example a variation of +/−5% of the disclosed value, or a variance of 4% of the disclosed value, or a variance of 3% of the disclosed value, a variance of 2% of the disclosed value or a variance of 1% of the disclosed value.

Furthermore, in the description herein, certain values may be disclosed in a range. The values showing the end points of a range are intended to illustrate a preferred range. Whenever a range has been described, it is intended that the range covers and teaches all possible sub-ranges as well as individual numerical values within that range. That is, the end points of a range should not be interpreted as inflexible limitations. For example, a description of a range of 1% to 5% is intended to have specifically disclosed sub-ranges 1% to 2%, 1% to 3%, 1% to 4%, 2% to 3% etc., as well as individually, values within that range such as 1%, 2%, 3%, 4% and 5%. The intention of the above specific disclosure is applicable to any depth/breadth of a range.

Additionally, when describing some embodiments, the disclosure may have disclosed a method and/or process as a particular sequence of steps. However, unless otherwise required, it will be appreciated the method or process should not be limited to the particular sequence of steps disclosed. Other sequences of steps may be possible. The particular order of the steps disclosed herein should not be construed as undue limitations. Unless otherwise required, a method and/or process disclosed herein should not be limited to the steps being carried out in the order written. The sequence of steps may be varied and still remain within the scope of the disclosure.

Description of Embodiments

Exemplary, non-limiting embodiments of the disclosure are provided hereinafter.

In various embodiments, there is provided a method of obtaining/predicting a clinical picture of a test subject, the method comprising: determining in a biological sample of the test subject, a biological data associated with one or more nucleic acid sequences located on human chromosome 1q arm, wherein a deviation in the biological data relative to a reference control is indicative of the clinical picture in the test subject.

In various embodiments, the clinical picture comprises at least one of: a likelihood/propensity/risk of a disease in a test subject, a likelihood/propensity/risk of recurrence/relapse of a disease in a test subject, an indication of the life expectancy/survival rate/time to death of a test subject having a disease or an efficacy of a treatment regimen for a test subject having a disease.

In some embodiments, the biological data is selected from the group consisting of: a copy number of the one or more nucleic acid sequences located on chromosome 1q arm, the level of mRNA transcripts of the one or more nucleic acid sequences located on chromosome 1q arm, the level of peptides encoded by the one or more nucleic acid sequences located on chromosome 1q arm, a copy number of chromosome 1q arm, a copy number of a region specific to chromosome 1q arm and combinations thereof. In some embodiments, the biological data is associated with two or more nucleic acid sequences located on chromosome 1q arm.

In various embodiments, the one or more nucleic acid sequences are located within the region spanning from chr1q21 to chr1q22 of the chromosome 1q arm, the region spanning from chr1q21.1 to chr1q21.3 of the chromosome 1q arm or at the chr1q21.3 position of the chromosome 1q arm. In various embodiments, the biological data comprises a copy number of chromosome 1q21, a copy number of chromosome 1q21.3, a copy number of a region specific to chromosome 1q21 to 1q22, a region specific to chromosome 1q21.1 to 1q21.3, or a region specific to chromosome 1q21.3.

In some embodiments, the human chromosome 1q21 comprises a region spanning from human chromosome chr1q21.1 to chr1q21.3.

In some embodiments, the reference control is a copy number of the one or more nucleic acid sequences in a reference healthy subject and wherein a copy number amplification/gain of the one or more nucleic acid sequences of the test subject relative to the reference control is indicative of a higher likelihood/propensity of a disease in the test subject compared to the reference healthy subject, a higher likelihood/propensity of recurrence of a disease in the test subject compared to the reference healthy subject, and/or a shorter life expectancy/survival rate/time to death of the test subject compared to the reference healthy subject.

In some embodiments, the reference control is a copy number of the one or more nucleic acid sequences in the test subject before the test subject undergoes a treatment regimen, and wherein a decrease in the copy number in the biological sample of the test subject obtained after the start of the treatment regimen is indicative that the treatment regimen is effective in the test subject.

In some embodiments, the reference control is a copy number of the one or more nucleic acid sequences in a healthy tissue sample of the test subject and wherein a copy number amplification/gain of the one or more nucleic acid sequences of a test sample in the test subject relative to the reference control is indicative of a higher likelihood/propensity of a disease in the test subject, a higher likelihood/propensity of recurrence of a disease in the test subject, and/or a shorter life expectancy/survival rate/time to death of the test subject.

In some embodiments, the reference control is a level of mRNA transcripts of the one or more nucleic acid sequences of a reference healthy subject and wherein an elevated level of the mRNA transcripts of the test subject relative to the reference control is indicative of a higher likelihood/propensity of a disease in the test subject compared to the reference healthy subject, a higher likelihood/propensity of recurrence of a disease in the test subject compared to the reference healthy subject, and/or a shorter life expectancy/survival rate/time to death of the test subject compared to the reference healthy subject.

In some embodiments, the reference control is a level of mRNA transcripts of the one or more nucleic acid sequences in the test subject before the test subject undergoes a treatment regimen, and wherein a decrease in the level of mRNA transcripts in the biological sample of the test subject obtained after the start of the treatment regimen indicates that the treatment regimen is effective in the test subject.

In some embodiments, the reference control is a level of mRNA transcripts of the one or more nucleic acid sequences in a healthy tissue sample of the test subject and wherein an elevated level of the mRNA transcripts in a test sample in the test subject relative to the reference control is indicative of a higher likelihood/propensity of a disease in the test subject, a higher likelihood/propensity of recurrence of a disease in the test subject, and/or a shorter life expectancy/survival rate/time to death of the test subject.

In some embodiments, the reference control is a level of peptides encoded by the one or more nucleic acid sequences of a reference healthy subject and wherein an elevated level of the peptides of the test subject relative to the reference control is indicative of a higher likelihood/propensity of a disease in the test subject compared to the reference healthy subject, a higher likelihood/propensity of recurrence of a disease in the test subject compared to the reference healthy subject, and/or a shorter life expectancy/survival rate/time to death of the test subject compared to the reference healthy subject.

In some embodiments, the reference control is a level of peptides encoded by the one or more nucleic acid sequences in the test subject before the test subject undergoes a treatment regimen, and wherein a decrease in the level of the peptides in the biological sample of the test subject obtained after the start of the treatment regimen indicates that the treatment regimen is effective in the test subject.

In some embodiments, the reference control is a level of peptides encoded by the one or more nucleic acid sequences in a healthy tissue sample of the test subject and wherein an elevated level of the peptides in a test sample in the test subject relative to the reference control is indicative of a higher likelihood/propensity of a disease in the test subject, a higher likelihood/propensity of recurrence of a disease in the test subject, and/or a shorter life expectancy/survival rate/time to death of the test subject.

In various embodiments, the disease is selected from the group consisting of: autoimmune disease, inflammatory disease, cardiovascular disease, metabolic disease, neoplastic disease, proliferative disease and combinations thereof. In some embodiments, the disease comprises a proliferative disease. In some embodiments, the proliferative disease is cancer.

In various embodiments, the test subject comprises a human subject. In certain embodiments, the human subject comprises a cancer patient. In various embodiments, a chromosome comprises a human chromosome.

In various embodiments therefore, there is provided a method of identifying risk of cancer in a human subject, the method comprising: determining in a biological sample of the subject, whether a copy number amplification/gain of a region specific to human chromosome 1q21 is present, wherein the presence of a copy number amplification/gain of the region specific to human chromosome 1q21 represents an elevated risk of cancer in the subject.

As may be appreciated by a person skilled in the art, cancer initiating stem-like cells, often called cancer stem cells (CSCs) or tumour initiating cells (TICs), are one of the contributing factors for cancer disease relapse as they are refractory to chemotherapy. As such, CSCs/TICs may repopulate following chemotherapy, leading to metastasis and tumour recurrence.

The inventors have identified a specific genomic locus, human chromosome 1q21, preferably chr1q21.3, which is enriched in CSCs/TICs. Further, the inventors have also found that DNA copy number amplification of the region is strongly associated with tumour recurrence, and correlates with poor prognosis, metastatsis and chemoresistance in breast cancer patients. Particularly, in various embodiments, DNA copy number amplification of the region can be detected in about 75% of recurrent breast cancer patients. DNA copy number amplification of the region may therefore be used as a biomarker for cancer diagnosis or prognosis, or for predicting, detecting or monitoring cancer recurrence, metastasis/micrometastasis or disease progression.

Accordingly, in some embodiments, said risk of cancer is at least one of a risk of occurrence of cancer, a risk of recurrence of cancer, a risk of metastasis of cancer, a risk of non-abatement of cancer, or a risk of cancer-based mortality.

In some embodiments, said one or more nucleic acid sequences or said region specific to chromosome 1q arm comprises non-coding sequences or a non-coding region. In some embodiments, said one or more nucleic acid sequences or said region specific to chromosome 1q arm comprises coding sequences, a coding region or a gene.

Accordingly, in some embodiments, determining a copy number of chromosome 1q arm or a region specific to chromosome 1q arm comprises determining a copy number of one or more nucleic acid sequences located on chromosome 1q arm, a copy number of one or more continuous genomic regions located on chromosome 1q arm, a copy number of one or more genes located on chromosome 1q arm or a gene expression of one or more genes located on chromosome 1q arm. In some embodiments, determining a copy number amplification of chromosome 1q arm or a region specific to chromosome 1q arm comprises determining a copy number amplification of one or more nucleic acid sequences located on chromosome 1q arm, a copy number amplification of one or more continuous genomic regions located on chromosome 1q arm, a copy number amplification of one or more genes located on chromosome 1q arm or an overexpression of one or more genes located on chromosome 1q arm.

In various embodiments therefore, the determining step comprises determining whether a copy number amplification/gain of at least one continuous genomic region, at least two continuous genomic regions, at least three continuous genomic regions or at least four continuous genomic regions located on human chromosome 1q21 or preferably 1q21.3 is present. Advantageously, detecting the copy number amplification of continuous genomic regions such as genes located on human chromosome 1q21 or preferably 1q21.3 as a proxy for detecting the copy number amplification of human chromosome 1q21 or preferably 1q21.3 is reliable and efficient.

In various embodiments, detecting a copy number amplification/gain is based on evaluating a copy number ratio of the one or more nucleic acid sequences of the test subject to a control/reference nucleic acid sequence in the test subject and wherein a copy number ratio exceeding a threshold value is indicative of a copy number amplification/gain. Accordingly, in various embodiments, the determining step further comprises evaluating a copy number ratio of at least one continuous genomic region, at least two continuous genomic regions, at least three continuous genomic regions or at least four continuous genomic regions in the subject to a control/reference continuous genomic region in the subject, wherein a copy number ratio exceeding a threshold value is indicative of a copy number amplification.

In various embodiments, the threshold value is based on evaluating a copy number ratio of the one or more nucleic acid sequences of a healthy reference subject to a control/reference nucleic acid sequence in the healthy reference subject. Accordingly, in various embodiments, the threshold value is obtained by evaluating a copy number ratio of the at least one continuous genomic region, the at least two continuous genomic regions, the at least three continuous genomic regions or the at least four continuous genomic regions in a healthy subject to a control/reference continuous genomic region in the healthy subject.

In various embodiments, the threshold value is based on evaluating a copy number ratio of the one or more nucleic acid sequences in a healthy tissue sample of the test subject to a control/reference nucleic acid sequence in the healthy tissue sample of the test subject. Accordingly, in various embodiments, the threshold value is obtained by evaluating a copy number ratio of the at least one continuous genomic region, the at least two continuous genomic regions, the at least three continuous genomic regions or the at least four continuous genomic regions in a healthy tissue sample of the test subject to a control/reference continuous genomic region in the healthy tissue sample of the test subject. The tissue sample may be a biological fluid sample or a biological solid sample.

In various embodiments, said evaluating a copy number ratio of the one or more nucleic acid sequences, the at least one continuous genomic region, the at least two continuous genomic regions, the at least three continuous genomic regions or the at least four continuous genomic regions comprises evaluating an average copy number ratio of at least two nucleic acid sequences, the at least two continuous genomic regions, the at least three continuous genomic regions or the at least four continuous genomic regions. Advantageously, evaluating an average copy number ratio increases the robustness of the method and gives greater confidence in identifying samples with copy number amplification.

In various embodiments, said evaluating an average copy number ratio of the at least two nucleic acid sequences, the at least two continuous genomic regions, the at least three continuous genomic regions or the at least four continuous genomic regions of the healthy reference subject comprises: obtaining a copy number ratio of each of the at least two or more nucleic acid sequences, the at least two continuous genomic regions, the at least three continuous genomic regions or the at least four continuous genomic regions of the healthy reference subject; and averaging the copy number ratios of the at least two or more nucleic acid sequences, the at least two continuous genomic regions, the at least three continuous genomic regions or the at least four continuous genomic regions of the healthy reference subject to obtain an average copy number ratio of the healthy reference subject.

In various embodiments, said evaluating a copy number ratio of the at least one continuous genomic region comprises evaluating an average copy number ratio of at least two continuous genomic regions, at least three continuous genomic regions or at least four continuous genomic regions located on human chromosome 1q arm or preferably 1q21 and wherein said evaluating an average copy number comprises: obtaining a copy number ratio of each of the at least two continuous genomic regions; and averaging the copy number ratios of the at least two continuous genomic regions to obtain an average copy number ratio.

In various embodiments, the threshold value is obtained by evaluating a mean copy number ratio based on two or more healthy reference subjects. In some embodiments, said evaluating a mean copy number ratio based on two or more healthy reference subjects comprises: (a) obtaining a copy number ratio of each of the at least two or more nucleic acid sequences, the at least two continuous genomic regions, the at least three continuous genomic regions or the at least four continuous genomic regions of a first healthy reference subject; (b) averaging the copy number ratios of the at least two or more nucleic acid sequences, the at least two continuous genomic regions, the at least three continuous genomic regions or the at least four continuous genomic regions of the first healthy reference subject to obtain a first average copy number ratio of the first healthy reference subject (c) repeating (a) and (b) for a second healthy reference subject to obtain a second average copy number ratio of the second healthy reference subject; (d) optionally repeating (c) for one or more subsequent healthy reference subject to obtain one or more subsequent average copy number ratio; and (e) adding the average copy number ratios of the two or more healthy reference subjects; and (b) computing a mean of the average copy number ratios.

In various embodiments, the threshold value is obtained by evaluating a mean copy number ratio of the at least one continuous genomic region located on human chromosome 1q arm or preferably 1q21 based on two or more healthy reference subjects and wherein said evaluating a mean copy number ratio based on two or more healthy reference subjects comprises: evaluating a copy number ratio of the at least one continuous genomic region of a first healthy reference subject; evaluating a copy number ratio of the at least one continuous genomic region of a second healthy reference subject; optionally evaluating a copy number ratio of the at least one continuous genomic region of one or more subsequent healthy reference subject to obtain one or more subsequent copy number ratios; and adding the copy number ratios of the two or more healthy reference subjects; and computing a mean of the copy number ratios.

In some embodiments, the method further comprises applying about 1 standard deviation, about 2 standard deviations or about 3 standard deviations to the mean of the average copy number ratios.

In some embodiments, the threshold value is at least about 1.01, at least about 1.02, at least about 1.03, at least about 1.04, at least about 1.05, at least about 1.06, at least about 1.07, at least about 1.08, at least about 1.09, at least about 1.10, at least about 1.11, at least about 1.12, at least about 1.13, at least about 1.14, at least about 1.15, at least about 1.20, at least about, 1.30, at least about 1.40 or at least about 1.50.

In various embodiments, said control/reference nucleic acid sequence or control/reference continuous genomic region is in a locus other than a locus in the chromosome 1q arm and/or in a locus other than a locus in the region spanning from 1q21.1 to 1q21.3 of the chromosome 1q arm. In some embodiments, the control/reference continuous genomic region comprises a continuous genomic region, such as a human gene, that is not located on human chromosome 1q21.3.

In some embodiments, the control/reference nucleic acid sequence or control/reference continuous genomic region is located on human chromosome 10, human chromosome 14 or human chromosome 17. In various embodiments, the control/reference continuous genomic region can be selected from but is not limited to: a human RPP30 gene or fragment thereof, a human RPPH1 gene or fragment thereof, a human EFTUD2 gene or fragment thereof and any combinations thereof.

In some embodiments, the continuous genomic region comprises a gene. In some embodiments, the continuous genomic region comprises a human gene. In some embodiments, the continuous genomic region is at least about 16 bp, at least about 17 bp, at least about 18 bp, at least about 19 bp, at least about 20 bp, at least about 21 bp, at least about 22 bp, at least about 23 bp, at least about 24 bp, at least about 25 bp, at least about 26 bp, at least about 27 bp, at least about 28 bp, at least about 29 bp or at least about 30 bp in length. In some embodiments, the continuous genomic region comprises non-coding DNA segments. In some embodiments, the continuous genomic region comprises junk DNA.

It may be appreciated that when the continuous genomic region comprises a gene, determining a copy number amplification of the continuous genomic region may include an indirect determination through determination of downstream events such as the presence/level of corresponding RNA transcripts and/or protein expression.

In various embodiments, the one or more nucleic acid sequences or the at least one continuous genomic region located on chromosome 1q arm is selected from the group consisting of the genes listed in the table in Table 1 below.

TABLE 1

| No. | Band | Chromosome | Gene Name |
|---|---|---|---|
| 1 | q21.3 | 1 | EFNA4 |
| 2 | q21.1 | 1 | SRGAP2B |
| 3 | q21.3 | 1 | S100A7L2 |
| 4 | q21.1 | 1 | RNVU1-18 |
| 5 | q21.1 | 1 | FAM72C |
| 6 | q21.3 | 1 | MIR8083 |
| 7 | q21.3 | 1 | MIR5698 |
| 8 | q21.3 | 1 | MIR190B |
| 9 | q21.1 | 1 | RNVU1-17 |
| 10 | q21.3 | 1 | RPTN |
| 11 | q21.2 | 1 | MIR5087 |
| 12 | q21.3 | 1 | C1orf189 |
| 13 | q21.1 | 1 | PIAS3 |
| 14 | q21.3 | 1 | CRCT1 |
| 15 | q21.3 | 1 | LCE1B |
| 16 | q21.1 | 1 | MIR6736 |
| 17 | q22 | 1 | RAB25 |
| 18 | q21.3 | 1 | BNIPL |
| 19 | q22 | 1 | RHBG |
| 20 | q21.1 | 1 | PPIAL4E |
| 21 | q22 | 1 | YY1AP1 |
| 22 | q21.3 | 1 | LCE1D |
| 23 | q21.3 | 1 | S100A2 |
| 24 | q22 | 1 | NAXE |
| 25 | q21.2 | 1 | NBPF9 |
| 26 | q21.2 | 1 | ACP6 |
| 27 | q22 | 1 | ARHGEF2 |
| 28 | q21.2 | 1 | TARS2 |
| 29 | q21.2 | 1 | HIST2H2AA3 |
| 30 | q22 | 1 | PAQR6 |
| 31 | q21.3 | 1 | SHE |
| 32 | q21.2 | 1 | HIST2H2BE |
| 33 | q21.3 | 1 | LCE2B |
| 34 | q21.3 | 1 | S100A5 |
| 35 | q21.1 | 1 | AC243756.1 |
| 36 | q21.2 | 1 | PLEKHO1 |
| 37 | q21.2 | 1 | NBPF11 |
| 38 | q21.3 | 1 | SPRR2G |
| 39 | q21.3 | 1 | S100A16 |
| 40 | q21.3 | 1 | SCNM1 |
| 41 | q21.3 | 1 | SPRR2A |
| 42 | q22 | 1 | UBQLN4 |
| 43 | q21.3 | 1 | LCE1A |
| 44 | q21.3 | 1 | LELP1 |
| 45 | q21.1 | 1 | NBPF20 |
| 46 | q22 | 1 | PMF1-BGLAP |
| 47 | q21.3 | 1 | RAB13 |
| 48 | q21.3 | 1 | ADAMTSL4 |
| 49 | q21.3 | 1 | LCE3D |
| 50 | q21.3 | 1 | NPR1 |
| 51 | q21.3 | 1 | JTB |
| 52 | q22 | 1 | BGLAP |

TABLE 1-continued

| No. | Band | Chromosome | Gene Name |
|---|---|---|---|
| 53 | q21.3 | 1 | SNX27 |
| 54 | q21.3 | 1 | RP11-126K1.2 |
| 55 | q21.2 | 1 | C1orf54 |
| 56 | q21.3 | 1 | ENSA |
| 57 | q21.3 | 1 | S100A12 |
| 58 | q21.3 | 1 | GATAD2B |
| 59 | q21.3 | 1 | POGZ |
| 60 | q22 | 1 | SCARNA4 |
| 61 | q21.3 | 1 | TNFAIP8L2 |
| 62 | q21.1 | 1 | RP11-14N7.2 |
| 63 | q21.3 | 1 | LYSMD1 |
| 64 | q21.2 | 1 | GPR89B |
| 65 | q21.3 | 1 | KCNN3 |
| 66 | q21.2 | 1 | MTMR11 |
| 67 | q22 | 1 | RIT1 |
| 68 | q21.3 | 1 | FLG2 |
| 69 | q21.3 | 1 | FLAD1 |
| 70 | q21.3 | 1 | CKS1B |
| 71 | q21.2 | 1 | MCL1 |
| 72 | q21.3 | 1 | HORMAD1 |
| 73 | q21.3 | 1 | CRNN |
| 74 | q21.3 | 1 | SPRR2E |
| 75 | q22 | 1 | GBAP1 |
| 76 | q21.3 | 1 | MIR4258 |
| 77 | q21.2 | 1 | RNVU1-7 |
| 78 | q21.1 | 1 | NBPF25P |
| 79 | q21.3 | 1 | SPRR1A |
| 80 | q21.3 | 1 | LCE3C |
| 81 | q21.3 | 1 | MRPL9 |
| 82 | q21.3 | 1 | INTS3 |
| 83 | q21.3 | 1 | CERS2 |
| 84 | q21.3 | 1 | PSMB4 |
| 85 | q21.3 | 1 | ZBTB7B |
| 86 | q21.3 | 1 | SPRR2F |
| 87 | q21.3 | 1 | HRNR |
| 88 | q21.3 | 1 | C2CD4D |
| 89 | q21.3 | 1 | TCHH |
| 90 | q21.2 | 1 | NBPF19 |
| 91 | q22 | 1 | SSR2 |
| 92 | q22 | 1 | CCT3 |
| 93 | q22 | 1 | THBS3 |
| 94 | q21.2 | 1 | HIST2H4A |
| 95 | q22 | 1 | RUSC1 |
| 96 | q21.2 | 1 | SF3B4 |
| 97 | q21.2 | 1 | LINC00624 |
| 98 | q21.3 | 1 | LCE5A |
| 99 | q21.3 | 1 | S100A7 |
| 100 | q21.3 | 1 | S100A6 |
| 101 | q21.3 | 1 | TCHHL1 |
| 102 | q21.3 | 1 | SELENBP1 |
| 103 | q21.3 | 1 | C1orf43 |
| 104 | q21.3 | 1 | GOLPH3L |
| 105 | q22 | 1 | GON4L |
| 106 | q21.3 | 1 | MIR554 |
| 107 | q21.3 | 1 | SLC39A1 |
| 108 | q21.2 | 1 | ANP32E |
| 109 | q22 | 1 | SLC25A44 |
| 110 | q22 | 1 | KIAA0907 |
| 111 | q21.2 | 1 | MIR4257 |
| 112 | q21.1 | 1 | LIX1L |
| 113 | q22 | 1 | MIR9-1 |
| 114 | q22 | 1 | RXFP4 |
| 115 | q21.1 | 1 | PEX11B |
| 116 | q21.3 | 1 | THEM5 |
| 117 | q22 | 1 | PMF1 |
| 118 | q21.2 | 1 | FALEC |
| 119 | q21.3 | 1 | IL6R |
| 120 | q21.2 | 1 | RPRD2 |
| 121 | q21.2 | 1 | GJA8 |
| 122 | q21.2 | 1 | ECM1 |
| 123 | q22 | 1 | EFNA1 |
| 124 | q21.3 | 1 | FLG-AS1 |
| 125 | q21.3 | 1 | ADAM15 |
| 126 | q21.3 | 1 | PSMD4 |
| 127 | q21.3 | 1 | NUP210L |
| 128 | q21.3 | 1 | SNAPIN |
| 129 | q21.3 | 1 | RFX5 |
| 130 | q21.3 | 1 | SPRR3 |

TABLE 1-continued

| No. | Band | Chromosome | Gene Name |
|---|---|---|---|
| 131 | q21.2 | 1 | PRPF3 |
| 132 | q21.1 | 1 | TXNIP |
| 133 | q22 | 1 | TTC24 |
| 134 | q21.3 | 1 | LCE2C |
| 135 | q21.1 | 1 | CH17-125A10.1 |
| 136 | q21.2 | 1 | BCL9 |
| 137 | q21.1 | 1 | GPR89A |
| 138 | q21.3 | 1 | FLG |
| 139 | q22 | 1 | SLC50A1 |
| 140 | q21.3 | 1 | ZNF687 |
| 141 | q21.1 | 1 | RNVU1-6 |
| 142 | q21.3 | 1 | S100A8 |
| 143 | q22 | 1 | TRIM46 |
| 144 | q21.3 | 1 | PIP5K1A |
| 145 | q21.3 | 1 | S100A10 |
| 146 | q21.3 | 1 | C1orf56 |
| 147 | q21.3 | 1 | MLLT11 |
| 148 | q21.1 | 1 | RNVU1-15 |
| 149 | q21.2 | 1 | RNVU1-1 |
| 150 | q21.3 | 1 | S100A14 |
| 151 | q22 | 1 | SMG5 |
| 152 | q21.3 | 1 | UBAP2L |
| 153 | q21.2 | 1 | VPS45 |
| 154 | q21.3 | 1 | LINC01527 |
| 155 | q21.2 | 1 | MRPS21 |
| 156 | q21.3 | 1 | LCE1C |
| 157 | q21.2 | 1 | ADAMTSL4- |
| 158 | q21.3 | 1 | LCE4A |
| 159 | q21.3 | 1 | OAZ3 |
| 160 | q22 | 1 | MUC1 |
| 161 | q22 | 1 | SEMA4A |
| 162 | q21.2 | 1 | BOLA1 |
| 163 | q21.3 | 1 | EFNA3 |
| 164 | q21.1 | 1 | RNVU1-14 |
| 165 | q21.3 | 1 | CGN |
| 166 | q21.1 | 1 | ANKRD34A |
| 167 | q22 | 1 | LAMTOR2 |
| 168 | q22 | 1 | PKLR |
| 169 | q21.3 | 1 | CHTOP |
| 170 | q22 | 1 | HCN3 |
| 171 | q21.2 | 1 | APH1A |
| 172 | q21.1 | 1 | CHD1L |
| 173 | q21.3 | 1 | PYGO2 |
| 174 | q22 | 1 | MTX1 |
| 175 | q21.1 | 1 | NUDT17 |
| 176 | q22 | 1 | FDPS |
| 177 | q21.2 | 1 | HIST2H2AB |
| 178 | q21.3 | 1 | DENND4B |
| 179 | q21.3 | 1 | CELF3 |
| 180 | q21.3 | 1 | LCE6A |
| 181 | q21.2 | 1 | FAM231D |
| 182 | q21.2 | 1 | RNVU1-3 |
| 183 | q22 | 1 | SNORA80E |
| 184 | q21.1 | 1 | GNRHR2 |
| 185 | q21.1 | 1 | RBM8A |
| 186 | q22 | 1 | LMNA |
| 187 | q22 | 1 | SCAMP3 |
| 188 | q21.3 | 1 | S100A11 |
| 189 | q21.3 | 1 | GABPB2 |
| 190 | q21.3 | 1 | TDRKH |
| 191 | q21.3 | 1 | DCST1 |
| 192 | q21.3 | 1 | RIIAD1 |
| 193 | q21.3 | 1 | PGLYRP4 |
| 194 | q21.3 | 1 | S100A1 |
| 195 | q21.3 | 1 | SHC1 |
| 196 | q21.2 | 1 | PPIAL4G |
| 197 | q21.2 | 1 | PDE4DIP |
| 198 | q21.3 | 1 | CDC42SE1 |
| 199 | q22 | 1 | POU5F1P4 |
| 200 | q21.3 | 1 | TMOD4 |
| 201 | q22 | 1 | ASH1L |
| 202 | q21.2 | 1 | PPIAL4C |
| 203 | q22 | 1 | TSACC |
| 204 | q21.3 | 1 | THEM4 |
| 205 | q21.3 | 1 | ARNT |
| 206 | q22 | 1 | FAM189B |
| 207 | q21.3 | 1 | PRUNE1 |
| 208 | q21.2 | 1 | HIST2H2BF |
| 209 | q21.3 | 1 | S100A4 |
| 210 | q22 | 1 | MIR92B |
| 211 | q21.3 | 1 | PMVK |
| 212 | q21.3 | 1 | ANXA9 |
| 213 | q21.3 | 1 | TPM3 |
| 214 | q21.2 | 1 | GJA5 |
| 215 | q21.3 | 1 | PI4KB |
| 216 | q21.3 | 1 | LENEP |
| 217 | q22 | 1 | MEF2D |
| 218 | q21.3 | 1 | UBE2Q1-AS1 |
| 219 | q21.3 | 1 | CRTC2 |
| 220 | q21.1 | 1 | PDZK1 |
| 221 | q21.3 | 1 | PGLYRP3 |
| 222 | q22 | 1 | SYT11 |
| 223 | q21.1 | 1 | PRKAB2 |
| 224 | q21.3 | 1 | CTSS |
| 225 | q21.3 | 1 | CHRNB2 |
| 226 | q21.3 | 1 | ILF2 |
| 227 | q21.2 | 1 | LINC00869 |
| 228 | q21.3 | 1 | PBXIP1 |
| 229 | q21.3 | 1 | S100A13 |
| 230 | q22 | 1 | KRTCAP2 |
| 231 | q21.2 | 1 | FCGR1A |
| 232 | q21.3 | 1 | KPRP |
| 233 | q21.3 | 1 | SMCP |
| 234 | q21.1 | 1 | NBPF12 |
| 235 | q21.3 | 1 | CTSK |
| 236 | q21.3 | 1 | AQP10 |
| 237 | q21.3 | 1 | RP1-140J1.1 |
| 238 | q21.3 | 1 | VPS72 |
| 239 | q21.2 | 1 | NBPF14 |
| 240 | q21.3 | 1 | PRR9 |
| 241 | q21.3 | 1 | S100A3 |
| 242 | q22 | 1 | GBA |
| 243 | q21.3 | 1 | SETDB1 |
| 244 | q21.3 | 1 | UBE2Q1 |
| 245 | q21.2 | 1 | HIST2H2BC |
| 246 | q21.2 | 1 | HIST2H3A |
| 247 | q21.3 | 1 | LCE3A |
| 248 | q21.3 | 1 | LCE1E |
| 249 | q21.3 | 1 | LCE1F |
| 250 | q21.3 | 1 | RP11-216N14.5 |
| 251 | q21.1 | 1 | HFE2 |
| 252 | q22 | 1 | CLK2 |
| 253 | q21.3 | 1 | MIR6737 |
| 254 | q22 | 1 | MIR6738 |
| 255 | q21.3 | 1 | SPRR2B |
| 256 | q22 | 1 | C1orf61 |
| 257 | q21.1 | 1 | POLR3GL |
| 258 | q21.1 | 1 | FAM72D |
| 259 | q21.3 | 1 | SEMA6C |
| 260 | q21.3 | 1 | ADAR |
| 261 | q21.3 | 1 | S100A7A |
| 262 | q21.3 | 1 | LOR |
| 263 | q21.2 | 1 | SV2A |
| 264 | q21.2 | 1 | HIST2H3D |
| 265 | q21.2 | 1 | TUFT1 |
| 266 | q21.3 | 1 | TDRD10 |
| 267 | q21.3 | 1 | SPRR1B |
| 268 | q21.2 | 1 | CA14 |
| 269 | q21.3 | 1 | HAX1 |
| 270 | q21.3 | 1 | DCST2 |
| 271 | q21.3 | 1 | LCE3E |
| 272 | q21.1 | 1 | PPIAL4D |
| 273 | q22 | 1 | GLMP |
| 274 | q22 | 1 | DAP3 |
| 275 | q22 | 1 | IQGAP3 |
| 276 | q21.1 | 1 | NOTCH2NL |
| 277 | q21.2 | 1 | HIST2H2AA4 |
| 278 | q22 | 1 | TMEM79 |
| 279 | q21.1 | 1 | NBPF10 |
| 280 | q21.3 | 1 | FAM63A |
| 281 | q21.3 | 1 | LCE2A |
| 282 | q21.1 | 1 | CD160 |
| 283 | q21.1 | 1 | ITGA10 |
| 284 | q21.3 | 1 | RORC |
| 285 | q21.2 | 1 | OTUD7B |
| 286 | q21.1 | 1 | RP11-403I13.8 |

TABLE 1-continued

| No. | Band | Chromosome | Gene Name |
|---|---|---|---|
| 287 | q21.2 | 1 | HIST2H4B |
| 288 | q21.3 | 1 | ATP8B2 |
| 289 | q22 | 1 | VHLL |
| 290 | q21.3 | 1 | CREB3L4 |
| 291 | q21.3 | 1 | LINGO4 |
| 292 | q21.2 | 1 | HIST2H2AC |
| 293 | q21.3 | 1 | IVL |
| 294 | q21.2 | 1 | CIART |
| 295 | q21.1 | 1 | FMO5 |
| 296 | q21.1 | 1 | ANKRD35 |
| 297 | q21.2 | 1 | HIST2H3C |
| 298 | q21.1 | 1 | PPIAL4F |
| 299 | q22 | 1 | MSTO1 |
| 300 | q21.3 | 1 | SPRR2D |
| 301 | q23.1 | 1 | GPATCH4 |
| 302 | q21.1 | 1 | POLR3C |
| 303 | q22 | 1 | MEX3A |
| 304 | q21.3 | 1 | SLC27A3 |
| 305 | q21.1 | 1 | RNF115 |
| 306 | q21.3 | 1 | RPS27 |
| 307 | q21.3 | 1 | S100A9 |
| 308 | q21.3 | 1 | LCE3B |
| 309 | q21.3 | 1 | LCE2D |
| 310 | q22 | 1 | DPM3 |
| 311 | q21.3 | 1 | C1orf68 |
| 312 | q21.1 | 1 | NBPF15 |
| 313 | q21.3 | 1 | SPRR4 |
| 314 | q21.2 | 1 | MIR6077 |

In various embodiments, the one or more nucleic acid sequences or the at least one continuous genomic region located on chromosome 1q arm is selected from the group consisting of a human TUFT1 gene or fragment thereof, a human S100A10 gene or fragment thereof, a human S100A11 gene or fragment thereof, a human SPRR1A gene or fragment thereof, a human SPRR1B gene or fragment thereof, a human S100A9 gene or fragment thereof, a human S100A8 gene or fragment thereof, a human S100A7 gene or fragment thereof, a human S100A6 gene or fragment thereof, a human S100A2 gene or fragment thereof, a human S100A16 gene or fragment thereof, a human S100A14 gene or fragment thereof, a human SNAPIN gene or fragment thereof, a human JTB gene or fragment thereof, a human RAB13 gene or fragment thereof, a human UBE2Q1 gene or fragment thereof, and a human EFNA3 gene or fragment thereof. In some embodiments, the one or more nucleic acid sequences or the at least one continuous genomic region is selected from the group consisting of: a human TUFT1 gene, a gene from the human S100 family and combinations thereof. In some embodiments, a gene from the human S100 family comprises a human S100A7 gene, a human S100A8 gene or a human S100A9 gene. In further embodiments, the one or more nucleic acid sequences or the at least one continuous genomic region comprises a human TUFT1 gene or fragment thereof, a human S100A8 gene or fragment thereof, and a human S100A7 gene or fragment thereof, or any combinations thereof.

The inventors have found that a 17-gene signature comprising the genes as disclosed herein above correlates with lower relapse-free survival in cancer patients, particularly breast cancer patients regardless of their estrogen receptor (ER) status. Further, the inventors have also found that the copy number amplification of the genes as disclosed herein above may act as a reliable proxy for detecting the copy number amplification of chromosome 1q arm, preferably 1q21.

In some embodiments, the biological sample comprises a solid biological sample. In certain embodiments, the solid biological sample comprises a solid sample derived from a solid excrement of the subject. In certain embodiments, the solid biological sample comprises a solid sample derived from a breast tissue or a tumour tissue such as a solid bulk tumour. In certain embodiments, the solid sample derived from a breast tissue or a tumour tissue comprises a breast tissue biopsy or a tumour biopsy.

In other embodiments, the biological sample comprises a biological fluid sample. In various embodiments, the biological fluid sample is selected from the group consisting of blood, serum, plasma, sputum, lavage fluid, cerebrospinal fluid, urine, semen, sweat, tears, saliva and the like. In certain embodiments, the biological fluid sample is selected from the group consisting of blood, plasma, serum and combinations thereof. In certain embodiments therefore, the biological sample is a fluid biological sample selected from the group consisting of: blood, plasma, serum and combinations thereof.

In various embodiments, the one or more nucleic acid sequences or the at least one continuous genomic region is present as cell-free DNA in the biological sample including solid sample and fluid sample. In various embodiments, the biological sample comprises circulating DNA of a tumour cell, circulating DNA of a tumour initiating cell, circulating DNA of a tumour stem cell, or circulating DNA of a cancer stem cell. In various embodiments, the one or more nucleic acid sequences or the at least one continuous genomic region is present in the biological sample as circulating DNA of a tumour cell, circulating DNA of a tumour initiating cell, circulating DNA of a tumour stem cell, or circulating DNA of a cancer stem cell. Accordingly, in an embodiment, the determining step comprises determining whether a copy number amplification is present in a cell-free DNA.

Without being bound by theory, it is believed that tumours may shed fragments of DNA into the bloodstream. Advantageously, embodiments of the method are capable of detecting a copy number or a copy number amplification of chromosome 1q arm, preferably 1q21, or one or more nucleic acid sequences or at least one continuous genomic region located on chromosome 1q arm, preferably 1q21 in the cell-free DNA present in the bloodstream of cancer patients. As may be appreciated by a skilled person, embodiments of the method may therefore be implemented as a liquid biopsy assay, which, as compared to a tissue assay, is more cost effective, less painful and less risky for cancer patients. Further, embodiments of the method are non-invasive, facilitate serial sampling and regular monitoring, enable unbiased detection of tumour specific finger print, are applicable in cases where tumour tissue is not available after surgery, have a small equipment footprint and are easy to implement. Embodiments of the method are therefore also particularly suitable for use in clinical settings.

Accordingly, in various embodiments, the method comprises a non-invasive method or a minimally invasive method.

In various embodiments, the method further comprises obtaining the biological sample from the test subject prior to the determining step. In various embodiments, the step of obtaining the biological sample from the test subject is a non-surgical step, a non-invasive step or a minimally invasive step. In some embodiments, the step of obtaining the biological sample from the test subject comprising withdrawing a blood sample from the test subject or obtaining a tumour biopsy from the test subject. In some embodiments, the method further comprises the step of removing particulate blood components from the blood sample to leave behind blood plasma or serum for use in the determining step. In various embodiments, the particulate blood components are selected from the group consisting red blood cells, white blood cells, platelets and combinations thereof.

In various embodiments, the determining step is carried out by performing an assay capable of detecting polymorphism in a nucleic acid sequence. In some embodiments, the assay comprises an assay that is capable of detecting copy number variation in a nucleic acid sequence. In certain embodiments therefore, the determining step comprises performing an assay selected from the group consisting of: Next-Generation Sequencing (NGS), Comparative Genome Hybridization (CGH), Array Comparative Genome Hybridization (aCGH), Fluorescence in situ Hybridization (FISH), digital PCR (dPCR) and quantitative real-time PCR (qPCR). As may be appreciated by a person skilled in the art, any other methods known in the art that are capable of detecting a copy number variation in a nucleic acid sequence may also be employed.

In one embodiment, the determining step comprises performing a digital PCR assay. In one embodiment, the determining step comprises performing a droplet digital PCR (ddPCR) assay. Advantageously, digital PCR and droplet digital PCR are highly sensitive and quantitative. As such, embodiments of the method comprising a digital PCR-based assay method allow for efficient and highly specific determination/measurement/detection of a copy number or a copy number amplification of chromosome 1q arm.

Accordingly, in various embodiments, the method requires no more than about 2 millilitres, no more than about 1.5 millilitres, no more than about 1 millilitres, no more than about 0.9 millilitres, no more than about 0.8 millilitres, no more than about 0.7 millilitres, no more than about 0.6 millilitres, no more than about 500 microlitres of biological sample, no more than about 450 microlitres of biological sample, no more than about 400 microlitres of biological sample, no more than about 350 microlitres of biological sample or no more than about 300 microlitres of biological sample. In various embodiments, the method is capable of determining/measuring/detecting a copy number or a copy number amplification of chromosome 1q arm in no more than about, 2 millilitres, no more than about 1.5 millilitres, no more than about 1 millilitres, no more than about 0.9 millilitres, no more than about 0.8 millilitres, no more than about 0.7 millilitres, no more than about 0.6 millilitres, no more than about 500 microlitres of biological sample, no more than about 450 microlitres of biological sample, no more than about 400 microlitres of biological sample, no more than about 350 microlitres of biological sample or no more than about 300 microlitres of biological sample.

In various embodiments, the method or kit has a sensitivity of no less than about 85%, no less than about 86%, no less than about 87%, no less than about 88%, no less than about 89%, no less than about 90%, no less than about 91%, no less than about 92% or no less than about 93% in detecting a copy number amplification of chromosome 1q arm, preferably 1q21 or a copy number amplification of one or more nucleic acid sequences or continuous genomic regions located on chromosome 1q arm, preferably 1q21.3. In various embodiments, the method or kit has a specificity of no less than about 85%, no less than about 86%, no less than about 87%, no less than about 88%, no less than about 89%, no less than about 90%, no less than about 91%, no less than about 92%, no less than about 93% no less than about 94%, no less than about 95%, no less than about 96% or no less than about 97% in detecting a copy number amplification of chromosome 1q arm, preferably 1q21.3 or a copy number amplification of one or more nucleic acid sequences or continuous genomic regions located on chromosome 1q arm, preferably 1q21. Accordingly, in some embodiments, the method has a sensitivity of no less than 85% and a specificity of no less than 85% in detecting a copy number amplification of a region specific to human chromosome 1q21.

In various embodiments, the method requires no more than about 48 hours to complete, no more than about 42 hours to complete, no more than about 36 hours to complete, no more than about 30 hours to complete, no more than about 24 hours to complete, no more than about 18 hours to complete, no more than about 12 hours to complete, no more than about 6 hours to complete or no more than about 3 hours to complete.

In some embodiments, the method is at least one of a diagnosis method or a prognosis method. In some embodiments, the method is an in vitro or ex vivo method.

In certain embodiments, the method further comprises stratifying the subject for treatment with a cancer therapy if a copy number amplification of chromosome 1q arm or of the region specific to chromosome 1q21 is present. In certain embodiments therefore, there is provided a method of stratifying a subject for a treatment/therapy, the method comprising: (a) determining in a biological sample of the patient, a biological data associated with one or more nucleic acid sequences located on human chromosome 1q arm; and (b) assessing whether the biological data deviates from a reference control; and (c) selecting a treatment/therapy based on the assessment in (b).

In various embodiments, there is provided a method of treating/preventing a condition/disease in a patient in need thereof, the method comprising: determining in a biological sample of the patient, a biological data associated with one or more nucleic acid sequences located on human chromosome 1q arm; and subjecting the patient to a treatment/therapy if the sample shows a deviation in the biological data relative to a reference control.

In some embodiments, the treatment/therapy is selected from the group consisting of radiation therapy, combination therapy, alternative therapy, complementary therapy, chemotherapy, drugs which show efficacy in killing tumour-initiating cells, drugs which show efficacy in treating recurrent patients, anthracyclines such as Adriamycin (doxorubicin) and Ellence (epirubicin), taxanes such as Taxol (paclitaxel) and Taxotere (docetaxel), alkylating agents such as cytoxan (cyclophosphamide), Selective Estrogen-Receptor Modulators such as Tamoxifen, Evista (raloxifene), Fareston (toremifene), aromatase inhibitors such as Aromasin (exemestane), Femara (letrozole), Arimidex (anastrozole), Megace (megestrol), biologic response modifiers such as Herceptin (trastuzumab) and other hormonal therapies such as Zoladex (goserelin acetate), Faslodex (fulvestrant), tyrosine kinase inhibitors and drugs that target JAK-STAT pathway (JAK: Janus kinase; STAT: Signal Transducer and Activator of Transcription). As may be appreciated by a person skilled in the art, an alternative therapy may be understood as a therapy that is used in place of conventional/traditional medicine while a complementary therapy may be understood as a therapy that is used as a supplement to conventional/traditional medicine.

In some embodiments, the treatment/therapy comprises administering a tyrosine kinase inhibitor to the patient. In some embodiments, the tyrosine kinase inhibitor comprises a Janus kinase inhibitor. In an embodiment, the Janus kinase inhibitor comprises pacritinib. Advantageously, the inventors have found out that a tyrosine kinase inhibitor showed higher efficacy in a patient who is positive for chr1q21.3 amplification as compared to, for example, conventional chemotherapy drugs such as Adriamycin and Taxol.

Accordingly, in some embodiments, the treatment/therapy of said subjecting step does not comprise administration of an anthracycline such as Adriamycin or a taxane such as Taxol.

In some embodiments, the patient was previously treated for the condition/disease by an earlier treatment/therapy. In some embodiments, the subject was previously ineffectively treated for cancer by an earlier therapy. In some embodiments, the patient was previously ineffectively treated for the condition/disease by the earlier treatment/therapy. In some embodiments, the earlier treatment/therapy is different from the treatment/therapy of said subjecting step. In some embodiments, the earlier therapy is different from a therapy using the therapeutic agent. In some embodiments, the earlier treatment/therapy comprises administration of an anthracycline such as Adriamycin or a taxane such as Taxol.

In various embodiments, there is provided a method of treating/preventing a condition/disease in a patient in need thereof, the method comprising: (a) subjecting the patient to a first treatment/therapy; (b) determining in the biological sample of the patient, a biological data associated with one or more nucleic acid sequences located on human chromosome 1q arm after said first treatment/therapy; (c) subjecting the patient to a second treatment/therapy if the sample shows a deviation in the biological data relative to a reference control in (b).

In various embodiments, there is provided a method of treating/preventing a condition/disease in a patient in need thereof, the method comprising: (a) determining in the biological sample of the patient, a biological data associated with one or more nucleic acid sequences located on human chromosome 1q arm; (b) subjecting the patient to a first treatment/therapy; (c) determining in the biological sample of the patient, the biological data associated with the one or more nucleic acid sequences located on human chromosome 1q arm after said first treatment/therapy; (d) subjecting the patient to a second treatment/therapy if in (c), the sample in (b) shows a deviation in the biological data relative to a reference control and/or relative to the biological data in (a).

In some embodiments, the first treatment/therapy is different from the second treatment/therapy. In some embodiments, the first treatment/therapy and/or second treatment/therapy is/are selected from the group consisting of radiation therapy, combination therapy, alternative therapy, complementary therapy, chemotherapy, drugs which show efficacy in killing tumour-initiating cells, drugs which show efficacy in treating recurrent patients, anthracyclines such as Adriamycin (doxorubicin) and Ellence (epirubicin), taxanes such as Taxol (paclitaxel) and Taxotere (docetaxel), alkylating agents such as cytoxan (cyclophosphamide), Selective Estrogen-Receptor Modulators such as Tamoxifen, Evista (raloxifene), Fareston (toremifene), aromatase inhibitors such as Aromasin (exemestane), Femara (letrozole), Arimidex (anastrozole), Megace (megestrol), biologic response modifiers such as Herceptin (trastuzumab) and other hormonal therapies such as Zoladex (goserelin acetate), Faslodex (fulvestrant), tyrosine kinase inhibitors and drugs that target JAK-STAT pathway. In certain embodiments, the first treatment/therapy comprises administration of an anthracycline such as Adriamycin or a taxane such as Taxol.

In some embodiments, the second treatment/therapy comprises administering a tyrosine kinase inhibitor to the patient. In some embodiments, the tyrosine kinase inhibitor comprises a Janus kinase inhibitor. In an embodiment, the Janus kinase inhibitor comprises pacritinib. In certain embodiments, the second treatment/therapy does not comprise administration of an anthracycline such as Adriamycin or a taxane such as Taxol.

The inventors have identified that a copy number amplification/gain of a region specific to chromosome 1q21, and/or a copy number amplification/gain of S100A8 and/or S100A9 located on chromosome 1q21 is a driver event associated with tumour survival and recurrence in multiple cancers. The inventors have also found out that inhibition of interleukin-1 receptor-associated kinase 1 (IRAK1) by a clinical inhibitor pacritinib blocks S100A8 and/or S100A9 as these proteins are downstream targets of IRAK1 signaling. Particularly, the inventors found that inhibition of IRAK1 phosphorylation by IRAK1/JAK2 inhibitor pacritinib ablated S100As expression, resulting in preferential growth inhibition of breast cancer cells containing amplified S100A8 and/or S100A9 genes. Accordingly, a copy number amplification of a region specific to chromosome 1q21, a copy number amplification of at least one continuous genomic region and/or a copy number amplification of at least one gene located on chromosome 1q21, is not only useful as a biomarker for the purposes described herein above, but it is also useful as an indicator of subjects who may benefit from therapeutic agents targeting the IRAK1-S100A8/A9 signaling pathway, the participants of the pathway including IRAK1, interleukin-1 receptor-associated kinase 4 (IRAK4), and S100 family members such at S100A7, S100A8 and S100A9. Particularly, IRAK4 was found to function upstream of IRAK1 kinase, and can phosphorylate and activate IRAK1. Accordingly, therapeutic agents targeting IRAK4 may also inhibit the activities of IRAK1.

Accordingly, in some embodiments, the treatment/therapy/cancer therapy comprises administering to the subject a therapeutic agent capable of suppressing IRAK1, IRAK4 or a S100 family member. Such a therapeutic agent may suppress the level, expression and/or (normal) activity of IRAK1, IRAK4 or the S100 family member by acting directly on these proteins, or their associated RNA transcripts or DNA sequences to cause a reduction and/or elimination of the expression and/or (normal) activity of IRAK1, IRAK4 or the S100 family member. Alternatively, such a therapeutic agent may suppress the level, expression and/or activity of IRAK1, IRAK4 or the S100 family member by acting on targets upstream of these proteins to cause a downstream reduction and/or elimination of the expression and/or (normal) activity of IRAK1, IRAK4 or the S100 family member. Methods known in the art for determining whether a therapeutic agent is capable of suppressing IRAK1, IRAK4 or a S100 family member may be employed. For example, western blot analysis may be carried out to determine if the level, expression or phosphorylation of IRAK1 in cells treated with a therapeutic agent is decreased as compared to untreated control cells.

In some embodiments, the therapeutic agent is capable of inhibiting/blocking the phosphorylation/kinase activity of IRAK1 and/or IRAK4.

In various embodiments therefore, there is provided a method of identifying/selecting/stratifying a subject for treatment/prevention/alleviation of a condition/disease by a therapeutic agent, the method comprising: determining in a biological sample of the subject, one or more biological data selected from the group consisting of: a copy number of human chromosome 1q arm, a copy number of one or more continuous genomic regions located on human chromosome 1q arm, a copy number of one or more genes located on human chromosome 1q arm and a gene expression of one or more genes located on human chromosome 1q arm; comparing the copy number and/or the gene expression to a threshold value, wherein an increased copy number and/or gene expression relative to the threshold value is indicative that the subject is a suitable candidate for treatment/prevention/alleviation of the condition/disease by the therapeutic agent, wherein the therapeutic agent is capable of modulating/inhibiting/downregulating/suppressing an activity/expression of IRAK1, IRAK4 and/or one or more S100 family members.

In various embodiments, there is also provided a method of determining a response and/or resistance to a therapeutic agent in a subject suffering from a condition/disease, the method comprising: determining a first biological data from a first biological sample of the subject before therapy or before a new cycle of therapy by the therapeutic agent; determining a second biological data from a second biological sample of the subject during therapy, after therapy or after completion of a cycle of therapy by the therapeutic agent; comparing the first biological data with the second biological data, wherein the biological data is one or more selected from the group consisting of: a copy number of human chromosome 1q arm, a copy number of one or more continuous genomic regions located on human chromosome 1q arm, a copy number of one or more genes located on human chromosome 1q arm and a gene expression of one or more genes located on human chromosome 1q arm, wherein the first biological data and the second biological data are the same type of biological data, wherein the therapeutic agent is capable of modulating/inhibiting/downregulating/suppressing an activity/expression of IRAK1, IRAK4 and/or one or more S100 family members, wherein the value of the second biological data relative to the value of the first biological data is indicative of the response and/or resistance to the therapeutic agent.

In some embodiments, a decreased value of the second biological data relative to the value of the first biological data is indicative of a positive response to the therapeutic agent. In some embodiments, an increased value or a substantially unchanged value of the second biological data relative to the value of the first biological data is indicative of resistance to the therapeutic agent.

In various embodiments, there is also provided a method of stratifying a subject for continual treatment/prevention/alleviation of a condition/disease by a therapeutic agent that is capable of modulating/inhibiting/downregulating/suppressing an activity/expression of IRAK1, IRAK4 and/or one or more S100 family members, the method comprising: determining a response and/or resistance to the therapeutic agent. In some embodiments, a positive response is indicative that the subject is a suitable candidate for continual treatment/prevention/alleviation of the condition/disease by the therapeutic agent. In some embodiments, resistance is indicative that the subject is not a suitable candidate for continual treatment/prevention/alleviation of the condition/disease by the therapeutic agent.

In various embodiments, there is provided a method of stratifying a subject for alternative treatment/prevention/alleviation of a condition/disease following treatment/prevention/alleviation of the condition/disease by a therapeutic agent that is capable of modulating/inhibiting/downregulating/suppressing an activity/expression of IRAK1, IRAK4 and/or one or more S100 family members, the method comprising: determining a response and/or resistance to the therapeutic agent. In some embodiments, a positive response is indicative that the subject is not a suitable candidate for alternative treatment/prevention/alleviation. In some embodiments, resistance is indicative that the subject is a suitable candidate for alternative treatment/prevention/alleviation.

In further embodiments, there is provided a method of treating/preventing/alleviating a condition/disease in a subject, the method comprising: administering to the subject a therapeutic agent that is capable of inhibiting/downregulating/suppressing an activity/expression of IRAK1, IRAK4 and/or one or more S100 family members, wherein the subject has, or is determined to have in his/her biological sample, an increased copy number and/or an increased gene expression of human chromosome 1q arm, one or more continuous genomic regions and/or one or more genes located on human chromosome 1q arm relative to a threshold value.

In certain embodiments, the subject was previously ineffectively treated for the condition/disease by an earlier treatment/therapy. In certain embodiments, the subject was previously ineffectively treated for the condition/disease by an earlier treatment/therapy that is not treatment/therapy by the therapeutic agent.

In some embodiments, the condition/disease comprises an IRAK1-mediated condition/disease and/or an IRAK4-mediated condition/disease, which include but is not limited a condition/disease selected from the group consisting of: autoimmune disease, inflammatory disease, cardiovascular disease, metabolic disease, neoplastic disease, proliferative disease such as cancer or combinations thereof.

Accordingly, in some embodiments, there is provided a method of treating cancer in a subject, the method comprising: administering to the subject a therapeutic agent capable of suppressing IRAK1, IRAK4 or a S100 family member, wherein the subject has, or is determined to have in his/her biological sample, a copy number amplification of a region specific to human chromosome 1q21.

In certain embodiments, the method comprises administering the therapeutic agent in combination with a chemotherapy drug. In an embodiment, the chemotherapy drug comprises paclitaxel. Advantageously, the inventors have found out that a neoadjuvant therapy comprising the administration of a chemotherapy drug to induce tumour regression before surgical removal of the tumour, followed by administration of embodiments of the therapeutic agent as described herein, whether alone or in combination with a chemotherapy drug, is well-tolerated and may prolong the disease free period before tumour regrowth in in vivo models.

Notably, while the inventors observed that the IRAK1-S100A7/8/9 signaling pathway showed correlation with the copy number amplification/gain of a region specific to chromosome 1q21, and/or the copy number amplification/gain of S100A8 and/or S100A9 located on chromosome 1q21, no correlation was observed between JAK2 signaling pathway and the copy number amplifications/gains. Accordingly, in some embodiments, the method is independent of or does not comprise determining the expression or activity of the following selected from the group consisting of: tyrosine kinase, Janus kinase 2 (JAK2), JAK2V61F, signal transducer and activator of transcription 3 (STAT3), FMS-like tyrosine kinase 3 (FLT3), colony stimulating factor 1 receptor (CSF1R), tyrosine kinase non receptor 1, ROS1 and combinations thereof in the subject.

In various embodiments, there is provided a therapeutic agent that is capable of modulating/inhibiting/downregulating/suppressing an activity/expression of IRAK1, IRAK4 and/or one or more S100 family members for use in the treatment of a condition/disease in a subject, wherein the subject has, or is determined to have in his/her biological sample, an increased copy number and/or an increased gene expression of human chromosome 1q arm, one or more continuous genomic regions and/or one or more genes located on human chromosome 1q arm relative to a threshold value. In some embodiments, there is provided a therapeutic agent capable of suppressing IRAK1, IRAK4 or a S100 family member for use in treating cancer in a subject who has, or is determined to have in his/her biological sample, a copy number amplification of a region specific to human chromosome 1q21.

In various embodiments, there is provided use of a therapeutic agent that is capable of modulating/inhibiting/downregulating/suppressing an activity/expression of IRAK1, IRAK4 and/or one or more S100 family members for use in the manufacture of a medicament for the treatment of a condition/disease in a subject, wherein the subject has, or is determined to have in his/her biological sample, an increased copy number and/or an increased gene expression of human chromosome 1q arm, one or more continuous genomic regions and/or one or more genes located on human chromosome 1q arm relative to a threshold value. In some embodiments, there is provided use of a therapeutic agent capable of suppressing IRAK1, IRAK4 or a S100 family member in the manufacture of a medicament for treating cancer in a subject, wherein the subject has, or is determined to have in his/her biological sample, a copy number amplification of a region specific to human chromosome 1q21.

In various embodiments, the therapeutic agent is selected from the group consisting of: a small molecule inhibitor, an antisense oligonucleotide, a gapmer, a short interfering RNA, a short hairpin RNA, a peptide, a CRISPR-Cas, an antibody, a ribozyme, and any combinations thereof.

In certain embodiments, the therapeutic agent comprises at least one of pacritinib, thymoquinone, a compound having the chemical formula

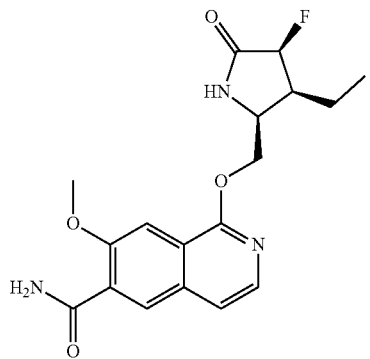 [SMILES: CC[C@@H]1[C@H](F)C(=O)N[C@@H]1COc1nccc2cc(C(N)=O)c(OC)cc12]

or analogs or therapeutically effective analogs thereof.

In some embodiments, there is provided a method of identifying/selecting/stratifying a subject for treatment/prevention/alleviation of a condition/disease by IRAK1/JAK2 inhibitors such as pacritinib or analogs thereof, the method comprising: determining in a biological sample of the subject, one or more biological data selected from the group consisting of: a copy number amplification/gain of S100A8, a copy number amplification/gain of S100A9, an overexpression of S100A8, an overexpression of S100A9 or combinations thereof.

In some embodiments, there is provided a method of predicting and/or monitoring tumour response to IRAK1/JAK2 inhibitors such as pacritinib or analogs thereof, the method comprising detecting S100A8 or S100A9 gene copy number or gene copy number amplification in cell free DNA in blood.

In some embodiments, there is provided a method of predicting and/or monitoring tumour response to IRAK1/JAK2 inhibitors such as pacritinib or analogs thereof, the method comprising detecting S100A8 or S100A9 mRNA expression in the tumour.

In some embodiments, there is provided a method of predicting and/or monitoring tumour response to IRAK1/JAK2 inhibitors such as pacritinib or analogs thereof, the method comprising detecting serum levels of S100A8 or S100A9 protein expression.

In some embodiments, said determining the biological data comprises contacting the biological sample with one or more oligonucleotides, primers and/or probes for hybridizing under stringent conditions to a region specific to human chromosome 1q arm or to one or more continuous genomic regions located on human chromosome 1q arm. In some embodiments, said determining the biological data comprises contacting the biological sample with a primer and/or probe for hybridizing under stringent conditions to a control/reference continuous genomic region.

Accordingly, in various embodiments, there is provided a kit comprising PCR primers for amplifying one, two, three or more polynucleotides selected from the group consisting of: (a) a nucleic acid sequence with a length of at least 16 base pairs located within the region spanning from chr1q21 to chr1q22 of the chromosome 1q arm, or (b) a polynucleotide having at least about 75%, at least about 80%, or at least about 85% sequence identity to the polynucleotide of (a).

In some embodiments, the polynucleotides to be amplified comprises non-coding sequences. In some embodiments, the polynucleotides to be amplified comprises the human genes listed in Table 1 or fragments thereof. In some embodiments, the polynucleotides to be amplified comprises a human TUFT1 gene or fragment thereof, a human S100A10 gene or fragment thereof, a human S100A11 gene or fragment thereof, a human SPRR1A gene or fragment thereof, a human SPRR1B gene or fragment thereof, a human S100A9 gene or fragment thereof, a human S100A8 gene or fragment thereof, a human S100A7 gene or fragment thereof, a human S100A6 gene or fragment thereof, a human S100A2 gene or fragment thereof, a human S100A16 gene or fragment thereof, a human S100A14 gene or fragment thereof, a human SNAPIN gene or fragment thereof, a human JTB gene or fragment thereof, a human RAB13 gene or fragment thereof, a human UBE2Q1 gene or fragment thereof, and a human EFNA3 gene or fragment thereof.

In certain embodiments, the kit comprises PCR primers for amplifying a human TUFT1 gene or fragment thereof, a human S100A8 gene or fragment thereof, and a human S100A7 gene or fragment thereof.

In some embodiments, the kit further comprises PCR primers for amplifying a human RPP30 gene or fragment thereof, a human RPPH1 gene or fragment thereof, and a human EFTUD2 gene or fragment thereof.

In various embodiments, there is provided a kit for determining whether a copy number amplification of a region specific to human chromosome 1q21 is present in a biological sample, the kit comprising: one or more oligonucleotides for hybridizing to a region specific to human chromosome 1q21 or for hybridizing to at least one continuous genomic region located on human chromosome 1q21; and instruction on using the oligonucleotides to determine whether a copy number amplification of a region specific to human chromosome 1q21 is present in the biological sample.

In some embodiments, the one or more oligonucleotides comprises a primer for amplifying at least one continuous genomic region located on human chromosome 1q21. In some embodiments, the at least one continuous genomic region is selected from the group consisting of: a human TUFT1 gene, a gene from the human S100 family, a human RPP30 gene and combinations thereof.

In further embodiments, the one or more oligonucleotides comprises a probe. In some embodiments, the one or more oligonucleotides comprises a hydrolysis probe. In some embodiments, the hydrolysis probe is labelled with a reporter fluorophore and/or a quencher fluorophore. In some embodiments, the hydrolysis probe is dual labelled. In one embodiment, the one or more oligonucleotides comprises a TaqMan probe.

In various embodiments therefore, there is provided a kit comprising probes for hybridizing under stringent conditions to one, two, three or more polynucleotides selected from the group consisting of: (a) a nucleic acid sequence with a length of at least 16 base pairs located within the region spanning from chr1q21 to chr1q22 of the chromosome 1q arm, or (b) a polynucleotide having at least about 75%, at least about 80%, or at least about 85% sequence identity to the polynucleotide of (a).

In some embodiments, the polynucleotides to which the probes are capable of hybridizing to comprise non-coding sequences. In some embodiments, the polynucleotides to which the probes are capable of hybridizing to comprise the human genes listed in Table 1 or fragments thereof. In some embodiments, the polynucleotides to which the probes are capable of hybridizing to comprise a human TUFT1 gene or fragment thereof, a human S100A10 gene or fragment thereof, a human S100A11 gene or fragment thereof, a human SPRR1A gene or fragment thereof, a human SPRR1B gene or fragment thereof, a human S100A9 gene or fragment thereof, a human S100A8 gene or fragment thereof, a human S100A7 gene or fragment thereof, a human S100A6 gene or fragment thereof, a human S100A2 gene or fragment thereof, a human S100A16 gene or fragment thereof, a human S100A14 gene or fragment thereof, a human SNAPIN gene or fragment thereof, a human JTB gene or fragment thereof, a human RAB13 gene or fragment thereof, a human UBE2Q1 gene or fragment thereof, and a human EFNA3 gene or fragment thereof.

In certain embodiments, the kit comprises probes for hybridizing under stringent conditions to a human TUFT1 gene or fragment thereof, a human S100A8 gene or fragment thereof, and a human S100A7 gene or fragment thereof.

In some embodiments, the one or more oligonucleotides, the primers or the probes comprise a sequence selected from the group consisting of:

TTTTAATCAGAGGGTGAGGGTGAT; (SEQ ID NO. 1)

GCTTCTCAATGTTGGAGGATACA; (SEQ ID No. 2)

GTCAAGATTGAGGAGGAAGAAGC; (SEQ ID No. 3)

TTCATAGATGGCTATGCCTCGG; (SEQ ID No. 4)

GGTGTTTCCCCACTAGCCA; (SEQ ID No. 5)

CCCAGAGAGTGTATTGGCCC; (SEQ ID No. 6)

TGCTATGTGGCCTTGGACAGATCACC; (SEQ ID No. 7)

AGTTTAAAGATCTCAGAGAGAGCCGAGGCA; (SEQ ID No. 8)

CCTTAGCGTATCACATGTGGACATGGACA; (SEQ ID No. 9)

and combinations thereof.

In some embodiments, the one or more oligonucleotides, the primers or the probes comprise a sequence selected from the group consisting of:

GTTAGAGAGTCTCCAGGCCC; (SEQ ID No. 10)

ACTGTAATCCAGCAAAAGCGG; (SEQ ID No. 11)

TGTCCACAGACTTTCTCAAAAGATAGGGCC; (SEQ ID No. 12)

and combinations thereof.

In some embodiments, the one or more oligonucleotides, the primers or the probes comprise a sequence selected from the group consisting of:

TTTTAATCAGAGGGTGAGGGTGAT; (SEQ ID NO. 1)

GCTTCTCAATGTTGGAGGATACA; (SEQ ID No. 2)

GTCAAGATTGAGGAGGAAGAAGC; (SEQ ID No. 3)

TTCATAGATGGCTATGCCTCGG; (SEQ ID No. 4)

GGTGTTTCCCCACTAGCCA; (SEQ ID No. 5)

CCCAGAGAGTGTATTGGCCC; (SEQ ID No. 6)

TGCTATGTGGCCTTGGACAGATCACC; (SEQ ID No. 7)

AGTTTAAAGATCTCAGAGAGAGCCGAGGCA; (SEQ ID No. 8)

CCTTAGCGTATCACATGTGGACATGGACA; (SEQ ID No. 9)

GTTAGAGAGTCTCCAGGCCC; (SEQ ID No. 10)

ACTGTAATCCAGCAAAAGCGG; (SEQ ID No. 11)

TGTCCACAGACTTTCTCAAAAGATAGGGCC; (SEQ ID No. 12)

and combinations thereof.

In various embodiments, said cancer is selected from the group consisting of neuroendocrine prostate cancer (NEPC), pancreatic cancer, uterine sarcoma, uterine cancer, ovarian cancer, liver cancer, lung cancer, breast cancer, bile duct cancer, cholangiocarcinoma, bladder cancer, sarcoma, esophagus cancer, prostate cancer, lung squamous cell carcinoma, stomach cancer, adenoid cystic carcinoma (ACC), pheochromocytoma and paraganglioma (PCPG), adenoid cystic carcinoma (ACyC), cervical cancer, melanoma, diffuse large B-cell lymphoma (DLBCL), head and neck cancer, mesothelioma, glioblastoma (GBM) and combinations thereof. In certain embodiments, the cancer comprises lung cancer or breast cancer. In an embodiment, the lung cancer is non-small cell lung cancer (NSCLC). Advantageously, embodiments of the method are capable of detecting chr1q21.3 copy number amplification in the circulating free DNA of patients with metastatic NSCLC (FIG. 17).

In some embodiments, said cancer comprises various forms of breast cancer, independent of subtype. As may be appreciated by a person skilled in the art, prior to the findings by the inventors, a biomarker which is applicable to a majority of breast cancers independent of their subtypes is not available, despite intense sequencing efforts to identify driver mutations in breast cancers.

In some embodiments, said cancer comprises a recurrent and/or a metastatic cancer.

In various embodiments, there is provided an isolated polynucleotide comprising more than one copy of: (a) a nucleic acid sequence with a length of at least 16 base pairs located within the region spanning from chr1q21 to chr1q22 of the chromosome 1q arm, or (b) a polynucleotide having at least about 75%, at least about 80%, or at least about 85% sequence identity to the polynucleotide of (a).

In some embodiments, the nucleic acid sequence with a length of at least 16 base pairs located within the region spanning from chr1q21 to chr1q22 of the chromosome 1q arm comprises a polynucleotide selected from the group consisting of human genes listed in Table 1 or fragments thereof. In some embodiments, the nucleic acid sequence with a length of at least 16 base pairs located within the region spanning from chr1q21 to chr1q22 of the chromosome 1q arm comprises a polynucleotide selected from the group consisting of a human TUFT1 gene or fragment thereof, a human S100A10 gene or fragment thereof, a human S100A11 gene or fragment thereof, a human SPRR1A gene or fragment thereof, a human SPRR1B gene or fragment thereof, a human S100A9 gene or fragment thereof, a human S100A8 gene or fragment thereof, a human S100A7 gene or fragment thereof, a human S100A6 gene or fragment thereof, a human S100A2 gene or fragment thereof, a human S100A16 gene or fragment thereof, a human S100A14 gene or fragment thereof, a human SNAPIN gene or fragment thereof, a human JTB gene or fragment thereof, a human RAB13 gene or fragment thereof, a human UBE2Q1 gene or fragment thereof, and a human EFNA3 gene or fragment thereof.

In some embodiments, the nucleic acid sequence with a length of at least 16 base pairs located within the region spanning from chr1q21 to chr1q22 of the chromosome 1q arm comprises a gene. In other embodiments, the nucleic acid sequence with a length of at least 16 base pairs located within the region spanning from chr1q21 to chr1q22 of the chromosome 1q arm belongs to a non-coding region. In certain embodiments, there is provided an isolated polynucleotide comprising a nucleic acid sequence having a copy number amplification of a region specific to human chromosome 1q21.

BRIEF DESCRIPTION OF FIGURES

FIG. 7 (B) shows the flow cytometry analysis for the ALDH activity in primary tumours and corresponding tumoursphere cells.

FIG. 8 (B) shows the Kaplan-Meier survival analysis of breast cancer patients with positive or negative S100A8 amplification in primary tumours.

FIG. 9 (B) is a ddPCR analysis of 1q21.3 genes in FACS-sorted ALDH positive and negative tumoursphere cells. FIG. 9 (C) is a ddPCR analysis of the copy number ratio of S100A8, PVRL4 and LAMB3 in normal tissues and tumoursphere cells normalized to the control reference gene RPP30.

FIG. 10 (B) is a ddPCR analysis of the primary tumours and matched recurrent tumours from patients who had recurrence within 5 years in OUH validation cohort. Shown are the averaged ratios of the three target genes TUFT1, S100A8 and S100A7 relative to the reference gene RPP30. FIG. 10 (C) is a breast orthotopic PDX model workflow. NOD-SCID mice bearing a breast PDX tumour were treated with vehicle or 20 mg/kg paclitaxel for 14 days to induce tumour regression. Untreated (n=4) and residual (n=5) tumours were harvested at the end of paclitaxel treatment. Recurrent (n=4) PDX tumours were harvested when the tumour relapse and its volume reached ~800 mm$^3$. FIG. 10 (D) is a ddPCR analysis of 1q21.3 amplification in indicated tumours. p-values were calculated with unpaired two-tailed Student's t-test. * p<0.05, *** p<0.001.

FIG. 11 (B) is a ddPCR analysis of 1q21.3 amplification in matching primary tumour DNA and plasma cfDNA of breast cancer patients from two independent cohorts. Positive 1q21.3 amplification was defined as those respective cutoff values as shown.

FIG. 13 (B) is a graph showing cell proliferation of MB231, MB436 and MB468 after individual shRNA knockdown of S100A7, S100A8 and S100A9. Data are expressed as means±s.d. of three technical replicates. FIG. 13 (C) is a representative western blot analysis showing induction of phospho-IRAK1 in MCF10A cells after treatment of S100A7/8/9 recombinant protein for 10 days. FIG. 13 (D) is a bar chart showing quantification of the number of tumourspheres after long term treatment of S100A7/8/9 recombinant protein separately in MCF10A. Data are expressed as means±s.d. of three independent experiments. FIG. 13 (E) is a graph showing cell proliferation of MCF10A after long term treatment of S100A7/8/9 recombinant protein separately. Data are expressed as means±s.d. of four technical replicates. FIG. 13 (F) is a bar chart showing quantification of the number of tumourspheres after IRAK1 wild-type (WT) and K239S mutant overexpression in MCF10A. Data are expressed as means±s.d. of three independent experiments. FIG. 13 (G) is a real time RT-PCR analysis of S100A7/8/9 gene expression in MCF10A tumourspheres overexpressing IRAK1 WT and K239S mutant. Data are expressed as means±s.d. of three technical replicates. All p-values were calculated with two tailed Student's t-test. * p<0.05, *** p<0.001.

FIG. 14 (B) is a real time RT-PCR analysis of S100A7/8/9 expression in HCC70 xenograft (n=4) treated with pacritinib. Data are expressed as means±s.e.m. of four xenograft tumour per group.

EXAMPLES

Example embodiments of the disclosure will be better understood and readily apparent to one of ordinary skill in the art from the following examples, tables and if applicable, in conjunction with the figures.

Figure 1:
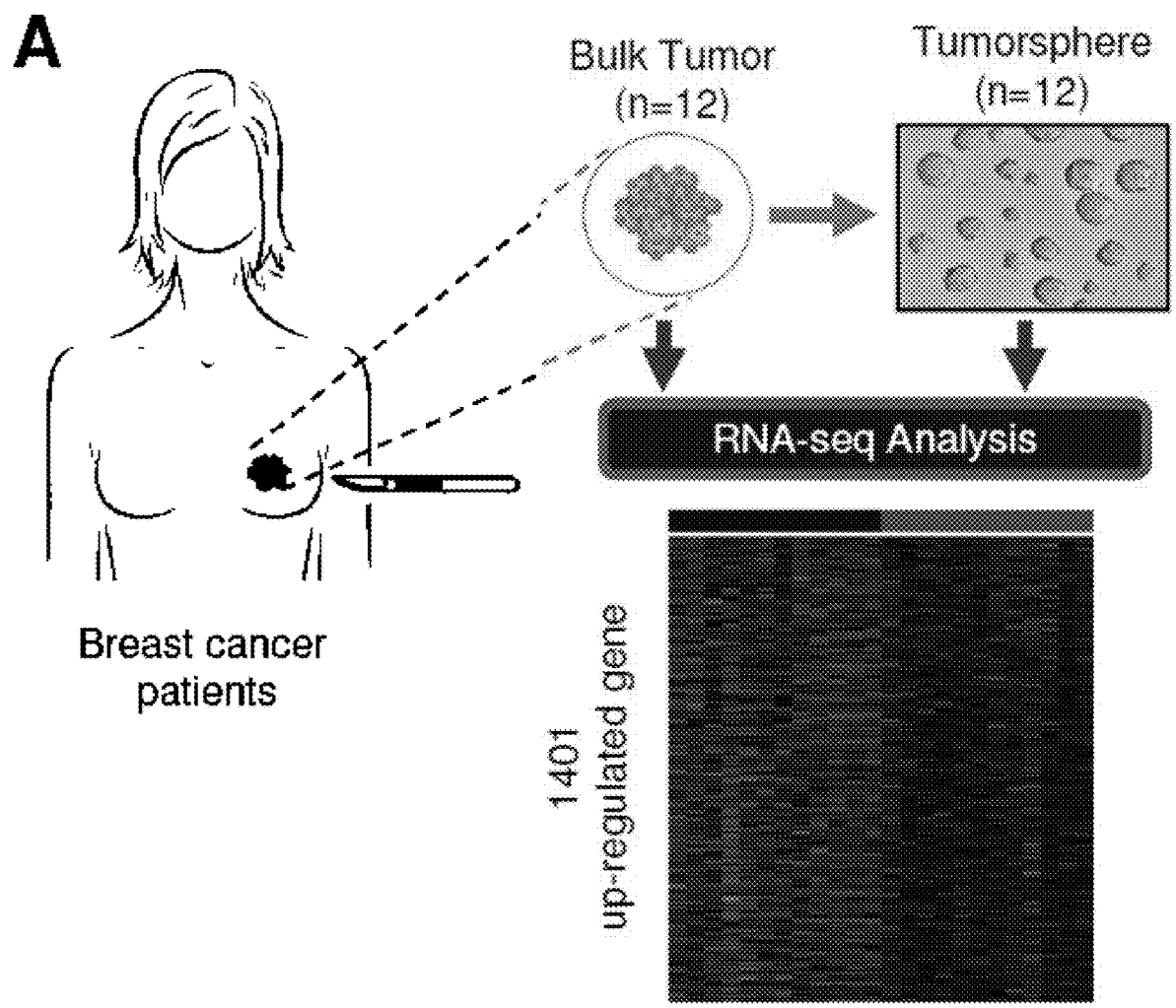
FIG. 1 shows that genomic interrogation of TICs identifies 1q21.3 amplification in breast cancer. (A) Schematic overview of sample preparation for RNA-seq analysis. Heat map displaying 1401 up-regulated genes in 12 patient-derived tumoursphere samples compared to matching bulk tumours as determined by RNA-seq. (B) Copy number variation of 1401 TICs-upregulated genes in breast cancer The Cancer Genome Atlas (TCGA) dataset (Breast Invasive Carcinoma, Cell 2015) in different chromosomes. Red, gene amplification; blue, gene deletion. (C) Location of the 17 up-regulated genes on chromosome 1q21.3. (D) Percentage of patients with 1q21.3 amplification in different breast cancer subtypes in the TCGA dataset (n=1098 patients). (E) Correlation of 1q21.3 or 8q amplifications and corresponding gene expressions in TCGA breast cancer dataset. p-values were calculated with Kruskal-Wallis test. (F) Time to death analysis of patients with 1q21.3 or 8q amplifications in TCGA breast cancer dataset. p-values were calculated with Mann-Whitney test. * $p<0.05$, n.s., not significant. (G) Kaplan-Meier relapse-free survival (RFS) analysis of the combined gene signature (17 genes on 1q21.3) in indicated breast cancer patients.
Figure 1:
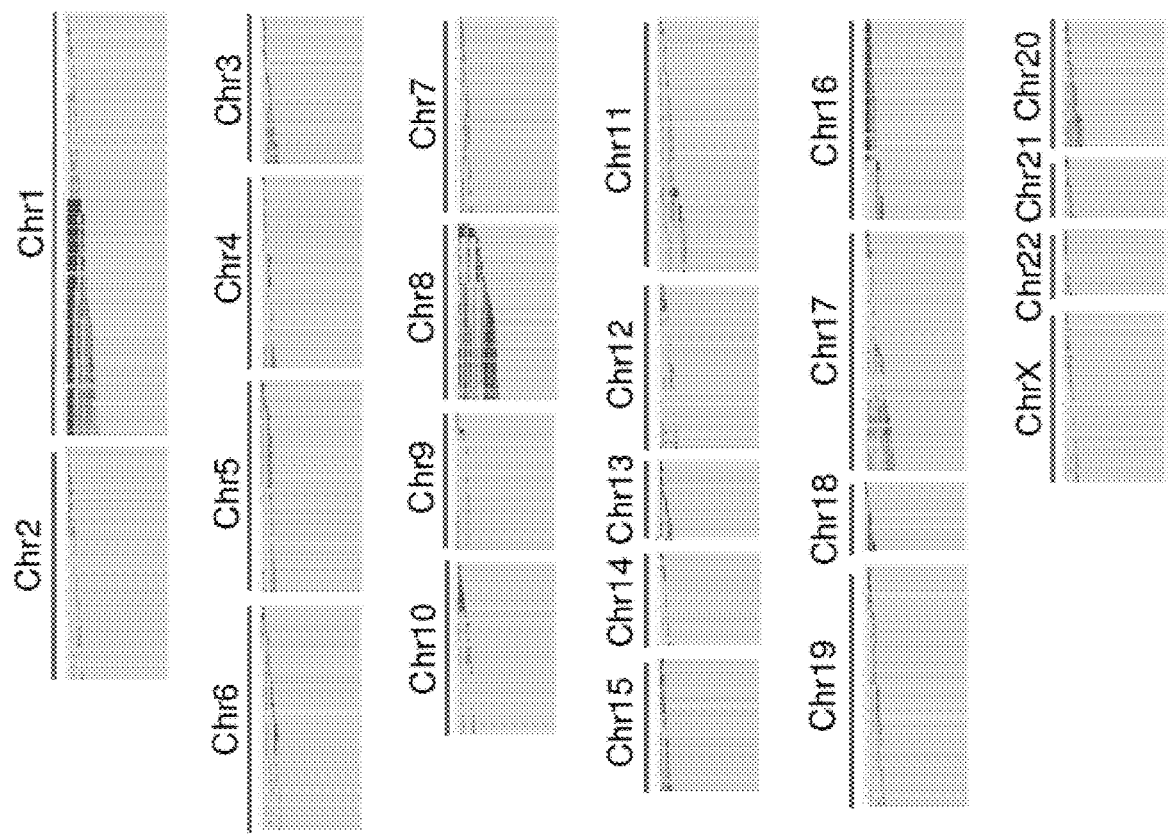
Figure 1:
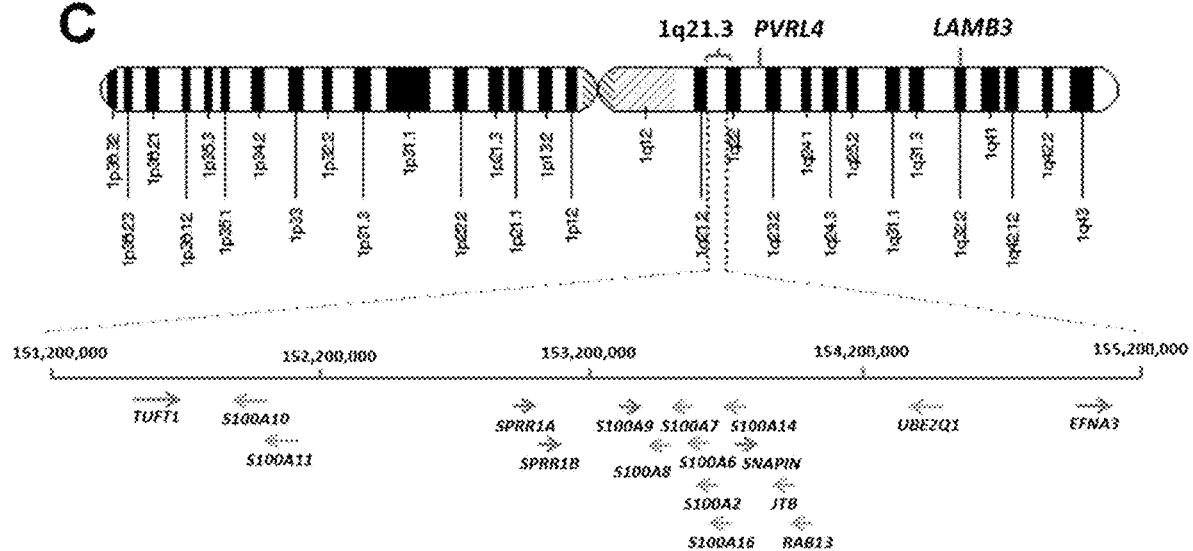
Figure 1:
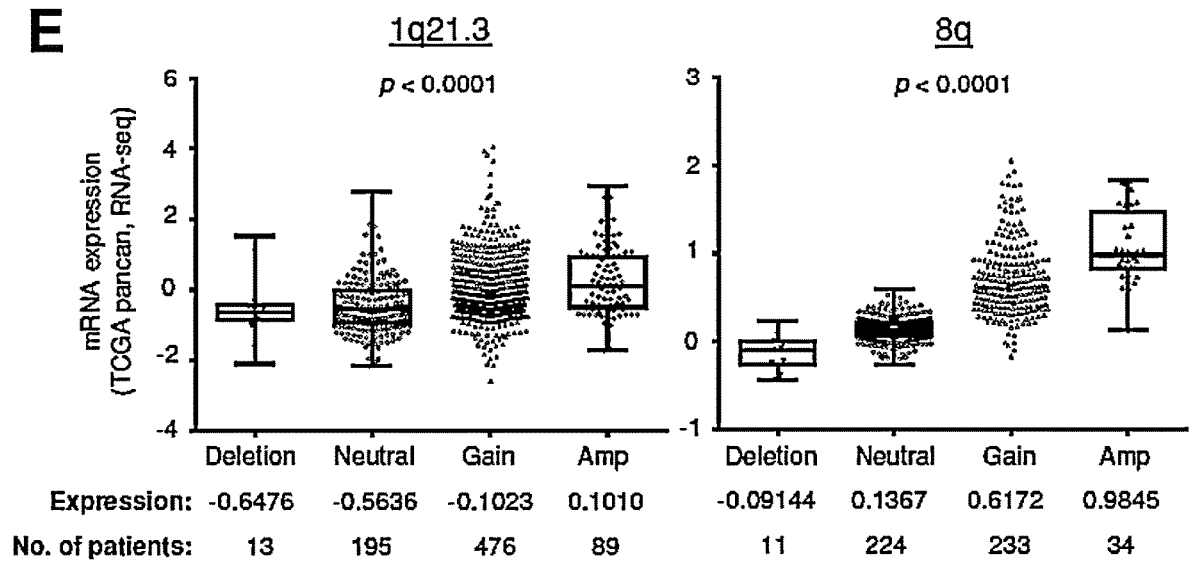
Figure 1:
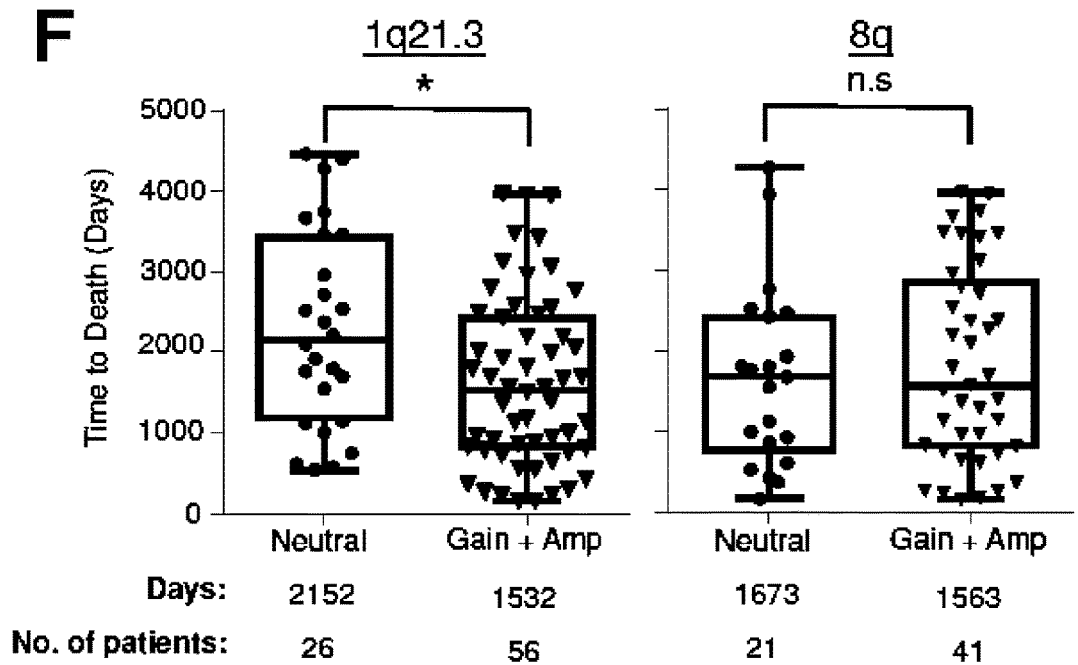
Figure 1:
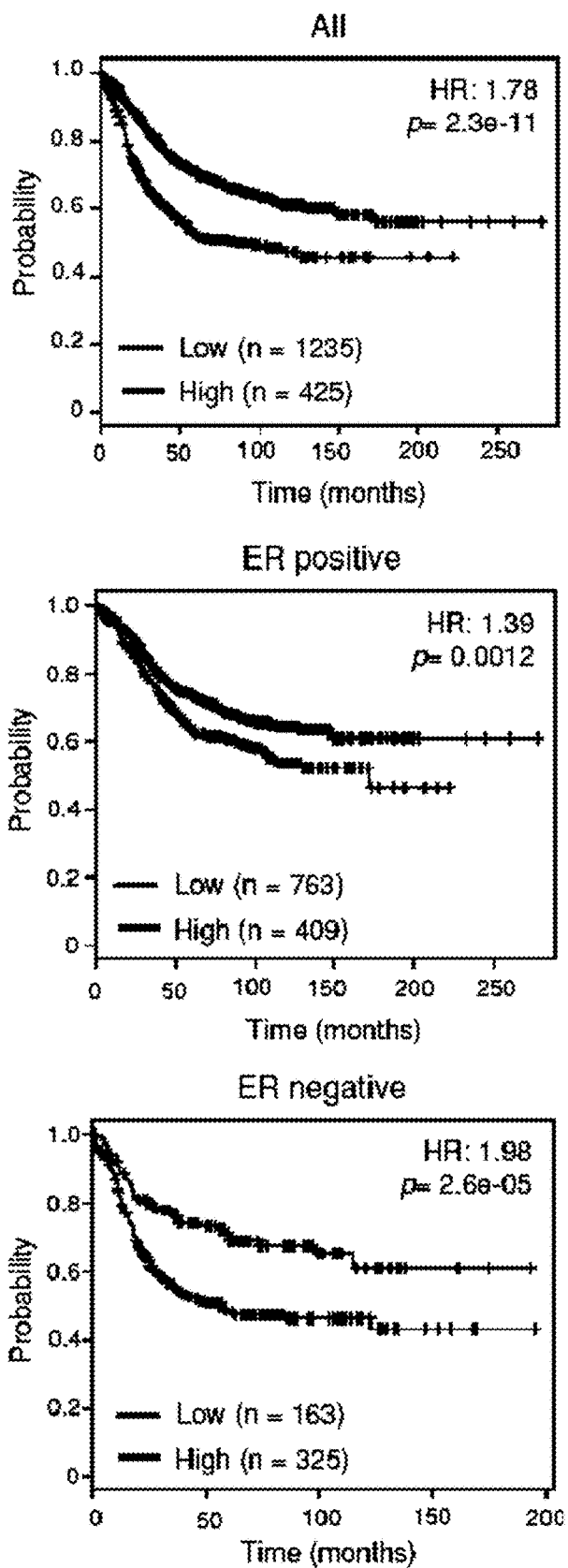
Figure 7:
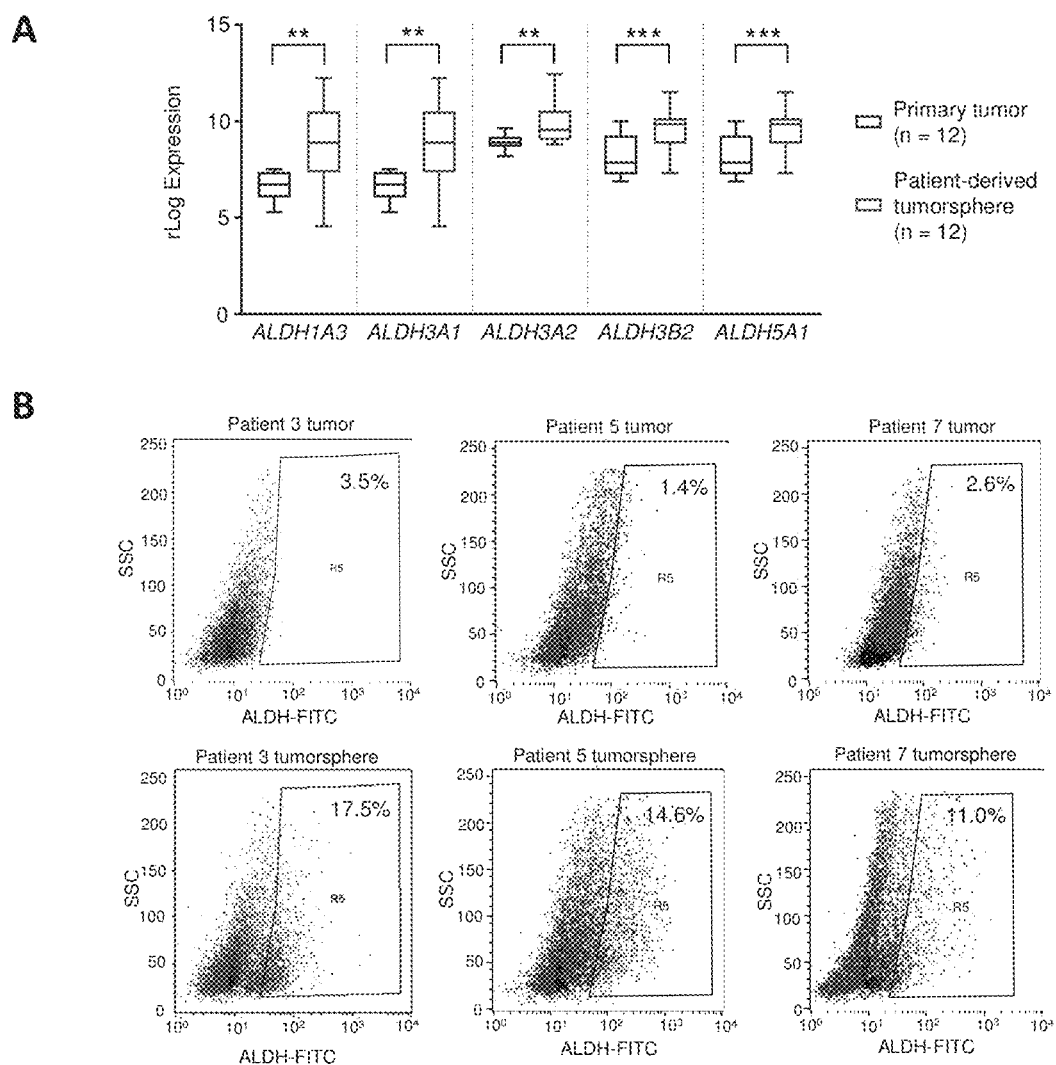
FIG. 7 (A) shows a boxplot of several aldehyde dehydrogenase (ALDH) family members' gene expression in primary tumours versus matching patient-derived tumourpsheres. p-value was calculated with Wilcoxon signed-rank test.  $p<0.01$, * $p<0.001$.

Example 1: Integrative Genomic Analysis of TICs Identifies 1q21.3 Amplification in Breast Cancer Cancer cells growing as tumourspheres in serum free medium are enriched for tumour initiating cells (TICs) and highly tumourigenic. To identify the genomic features associated with TICs, tumoursphere culture was used to enrich the TIC subpopulation of tumour cells from 12 surgical breast tumours and RNA-sequencing (RNA-seq) analysis was performed to compare their gene expression profiles with matched bulk tumours. This analysis identified 1401 genes which expressions were commonly up-regulated in the TIC-enriched tumourspheres as compared to the matched tumours (fold change>2, FDR<0.05) (FIG. 1A). Consistent with other reports, several ALDH family members such as ALDH1A3 were significantly up-regulated in the patient-derived tumourspheres (FIG. 7A). These patient-derived tumoursphere cells displayed much higher ALDH activity compared to their bulk tumour cells (FIG. 7B) and were able to initiate tumour formation when engrafted into immunodeficient mice at low cell numbers (data not shown).

Genomic instability is a hallmark and major contributing factor for cancer. The inventors next proceeded to determine whether the identification of DNA copy number alterations associated with TIC could potentially be used as a biomarker to track and predict cancer relapse.

To identify genes which up-regulation in the RNA-seq analysis may potentially be associated with copy number amplification (CNA), the list of 1401 TIC up-regulated genes was categorized based on chromosome locations and checked for CNA using The Cancer Genome Atlas (TCGA) breast cancer genomic dataset. The analysis revealed two subgroups of genes located on chromosome 1 (86 genes) and chromosome 8 (38 genes) which displayed CNA in a substantial number of breast cancer patients (~12% and ~16% respectively) (FIG. 1B). Further analysis revealed that 17 out of the 86 genes on chromosome 1 (chr1) were clustered at 1q21.3 (FIG. 1C), indicating a gain of 1q21.3.

Figure 15:
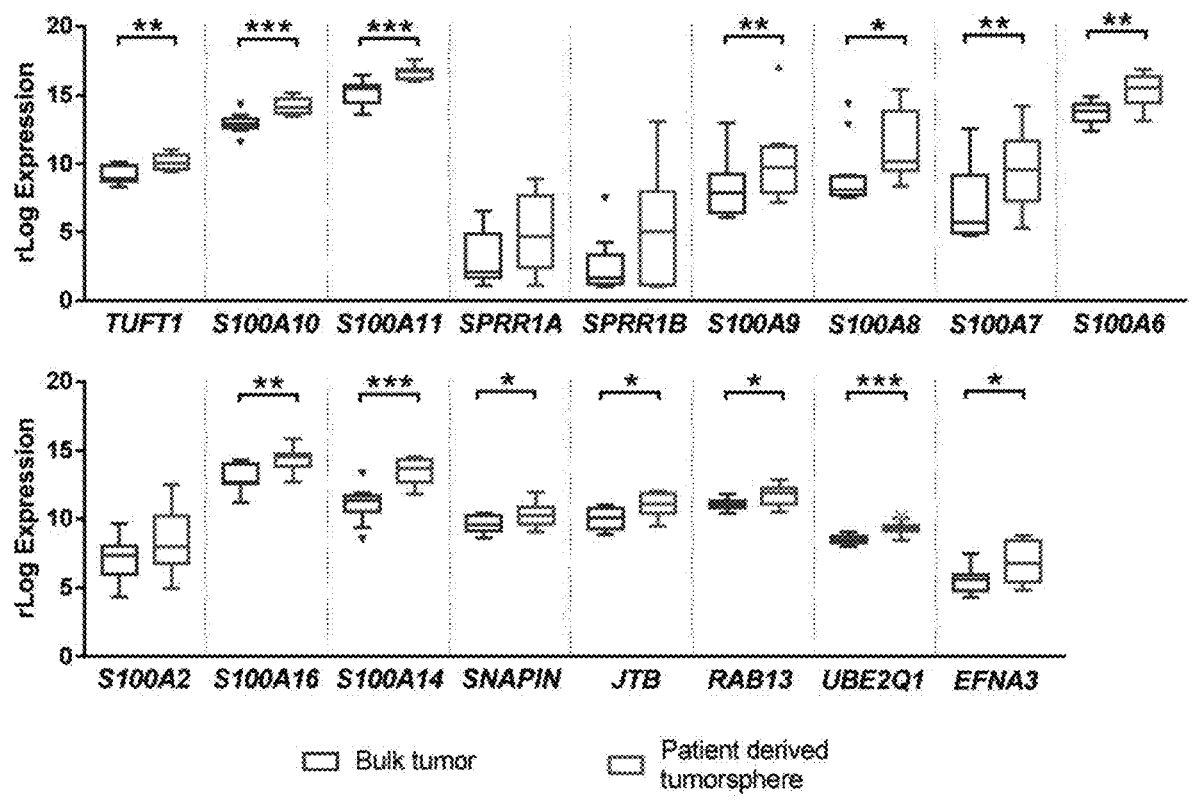
FIG. 15 is a boxplot of 17 chr1q21.3 genes up-regulated in patient-derived tumourspheres compared to matching bulk tumour. p-value was calculated with Wilcoxon signed-rank test. *p<0.05, p<0.01, *p<0.001.

These genes were all up-regulated in the patient-derived tumourspheres compared to the primary bulk tumours (FIG. 15). Detailed stratification of the patients into the four different breast cancer molecular subtypes revealed that the 17 genes amplified in 1q21.3 were present in all breast cancer subtypes but more enriched in basal-like breast tumours (31% in basal-like tumours vs. 12% in human epidermal growth factor receptor 2 positive (HER2+) tumours and 10% in luminal tumours) (GISTIC annotation: +2) (FIG. 1D).

Further analysis in TCGA showed correlation of both 1q21.3 (17 genes) and 8q (38 genes) copy number amplifications with their respective mRNA gene expressions (FIG. 1E). However, only patients with 1q21.3 amplification showed a significantly shorter time to death from initial pathologic diagnosis (p=0.0248) (FIG. 1F), indicating a potential role of 1q21.3 amplification in breast cancer progression. Consistently, a meta-analysis of breast cancer patient survival using Kaplan-Meier plotter online breast cancer survival analysis (www.kmplot.com) showed that the 17-gene expression signature of 1q21.3 was able to predict relapse-free survival in breast cancer patients, regardless of ER status (FIG. 1G), demonstrating the potential prognostic value of 1q21.3 amplification in breast cancer.

The potential of chr1q21.3 CNA as a diagnostic biomarker was validated in a retrospective a cohort of 67 breast cancer patients (Singapore discovery cohort), whose clinical pathological characteristics are summarized in Table 2 below.

TABLE 2

Clinical pathological characteristics of patients used in Singapore TTSH discovery cohort
Singapore TTSH Discovery Cohort

| Characteristics | Patients (n = 67) |
|---|---|
| Age | |
| <41 | 6 |
| 41-50 | 15 |
| 51-60 | 18 |
| >60 | 28 |
| Tumor size | |
| pT1 (<2.0 cm) | 12 |
| pT2 (2.0 to 5.0 cm) | 39 |
| pT3 (>5.0 cm) | 6 |
| pT4 | 10 |
| Stage | |
| I | 11 |
| II | 29 |
| III | 18 |
| IV | 9 |
| Subtype | |
| ER+ | 40 |
| HER2+ | 13 |
| TNBC | 14 |
| Lymph node status | |
| pN0 | 27 |
| pN1 | 19 |
| pN2 | 11 |
| pN3 | 10 |

TABLE 2-continued

Clinical pathological characteristics of patients used in Singapore TTSH discovery cohort
Singapore TTSH Discovery Cohort

| Characteristics | Patients (n = 67) |
|---|---|
| Race | |
| Chinese | 51 |
| Malay | 7 |
| Indian | 5 |
| Others | 4 |

Figure 8:
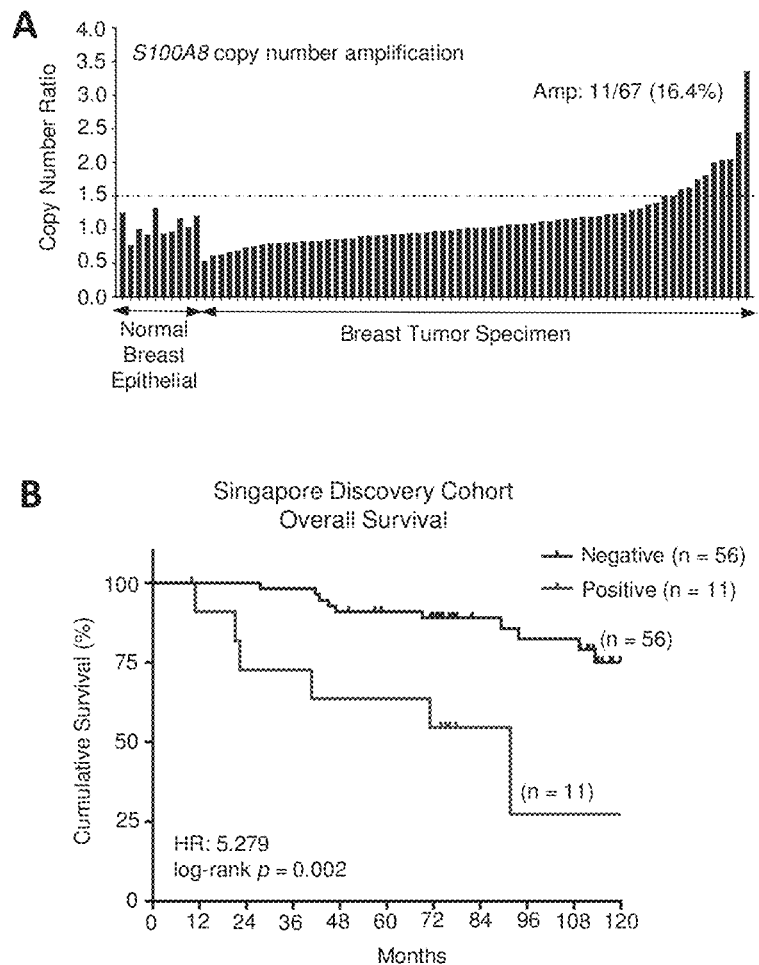
FIG. 8 (A) shows the clinical validation of copy number amplification of S100A8 gene in 67 breast tumour samples using real-time PCR. Ten normal breast epithelial tissues were used as control. A cutoff of 1.5 copy number ratio for S100A8 gene was used to yield two groups.

Using genomic real-time polymerase chain reaction (PCR) and S100A8 gene as a readout of 1q21.3, it was found that 11 out of the 67 primary tumours (16.4%) had S100A8 gene amplification (using 1.5 fold relative to the normal genome as the cutoff) (FIG. 8A). Furthermore, breast cancer patients positive for S100A8 amplification had significantly lower overall survival compared to non-amplified patients (FIG. 8B) [HR: 5.279, 95% confidence interval (CI), 1.868 to 14.916, log-rank p=0.002]. In particular, the patient group with S100A8 amplification showed a significantly higher death rate within 10 years follow-up (5 of 11 patients, 45.5%) compared to patients without S100A8 amplification (10 of 56 patients, 17.9%) [p=0.0447].]. These results are consistent with the data analysis from the TCGA dataset. Multivariate Cox regression analysis confirmed S100A8 amplification as an independent predictor of poor survival [HR: 7.134; 95% Cl, 2.226 to 22.869; log-rank p=0.001] which outperformed other tumour characteristics (see Table 3 below). These findings collectively supported a prognostic value of 1q21.3 amplification in breast cancer.

TABLE 3

Multivariate Cox regression analysis of 1q21.3 amplification status for overall survival of Singapore TTSH discovery cohort

| Clinical variable | Tumor DNA HR | 95% CI | p-value |
|---|---|---|---|
| CNA status (Negative vs Positive) | 7.134 | 2.226 to 22.869 | 0.001 |
| ER status (Positive vs Negative) | 2.666 | 0.916 to 7.761 | 0.072 |
| HER2 status (Negative vs Positive) | 0.527 | 0.159 to 1.750 | 0.296 |
| Tumor size (T1-2 vs T3-4) | 3.355 | 0.317 to 35.524 | 0.315 |
| Lymph nodes (N0 vs N1-3) | 1.538 | 0.364 to 6.494 | 0.558 |
| Stage (Stage 1-2 vs Stage 3-4) | 2.091 | 0.634 to 6.897 | 0.226 |

Figure 2:
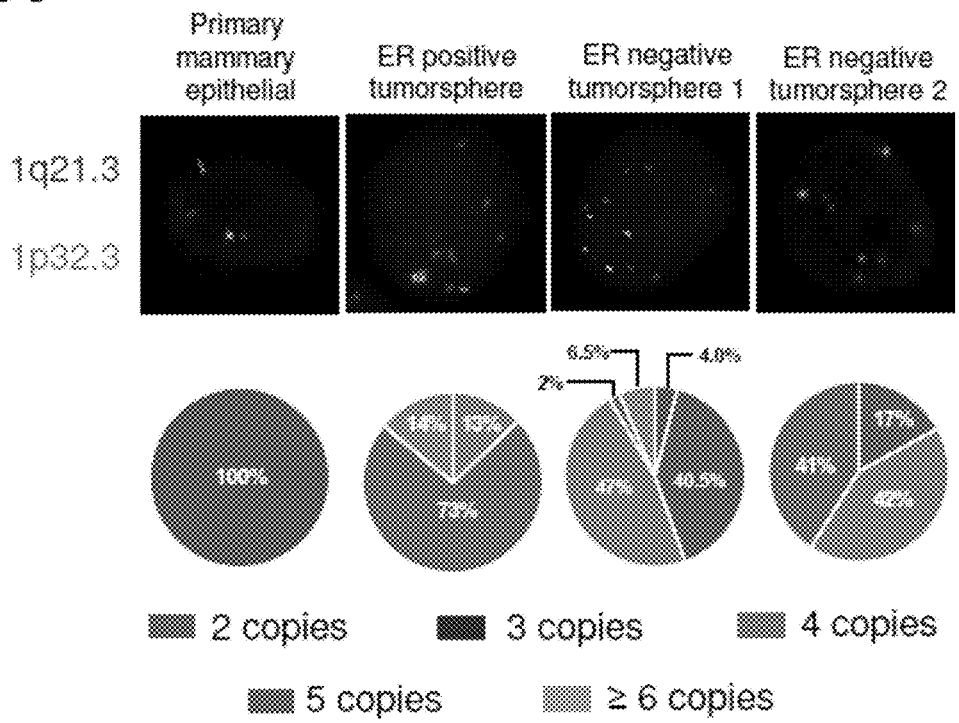
FIG. 2 shows that 1q21.3 amplification is enriched in TICs and associated with tumour recurrence. (A) Representative DNA-FISH images of primary mammary epithelial cells and patient-derived tumoursphere cells hybridized with DNA probes to detect 1q21.3 (red) and 1p32.3 (green). Percentage of cells with different copy numbers of 1q21.3 is shown in the pie chart below the corresponding representative images. (B) ddPCR analysis of 1q21.3 amplification in primary tumours and matched tumoursphere cells. (C) ddPCR analysis of primary tumours from patients without recurrence within 5 years. (D) ddPCR analysis of the primary tumours and matched recurrent tumours from patients who had a recurrence within 5 years. (E) Scatterplot graph summarizing the results from (C), and (D). p-values were calculated with McNemar test.  $p<0.01$, * $p<0.001$.
Figure 2:
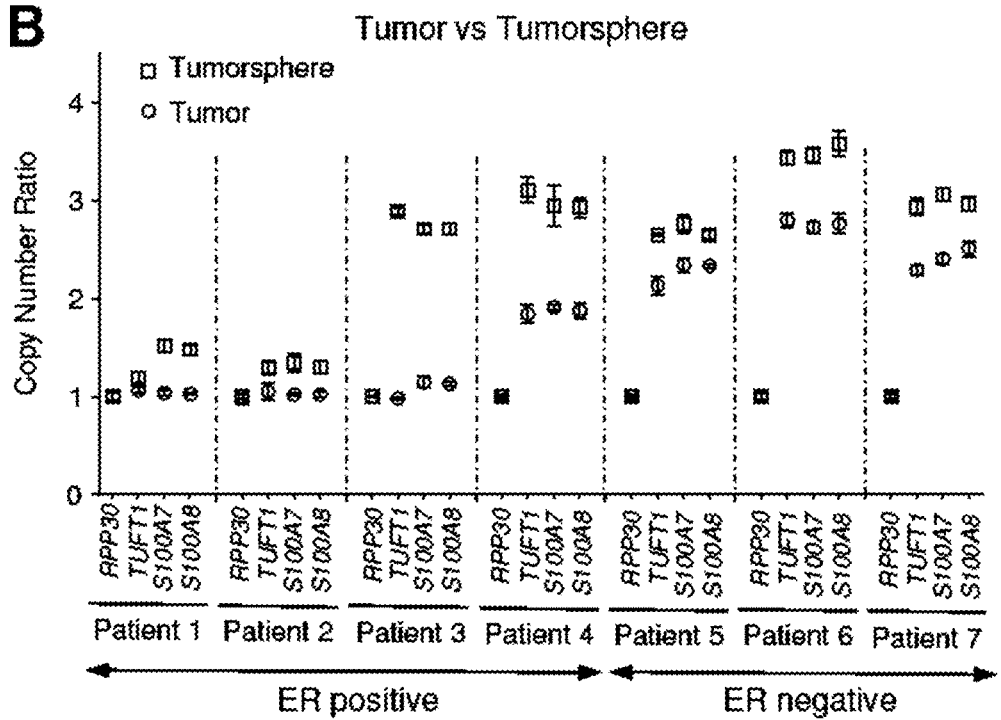
Figure 2:
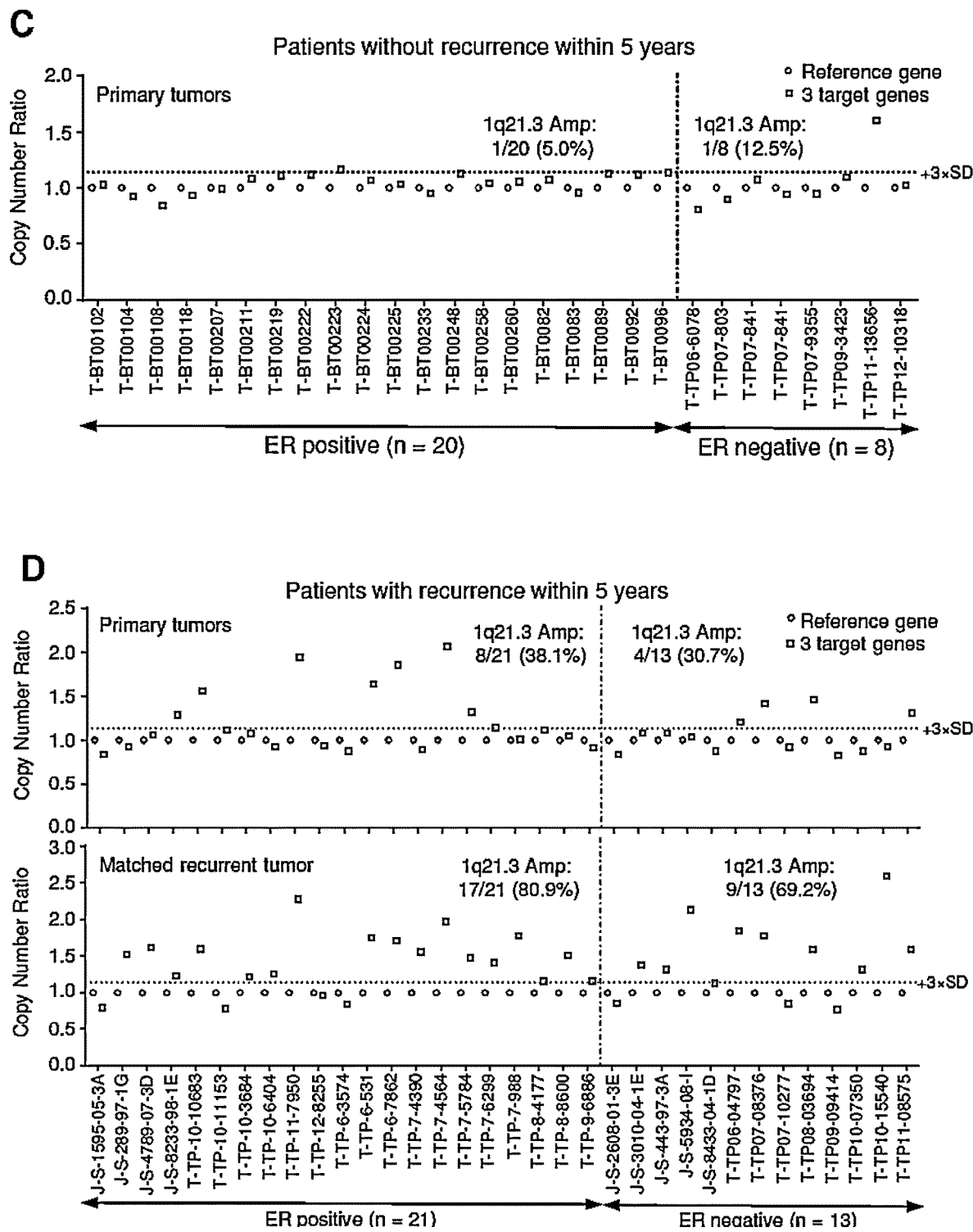
Figure 2:
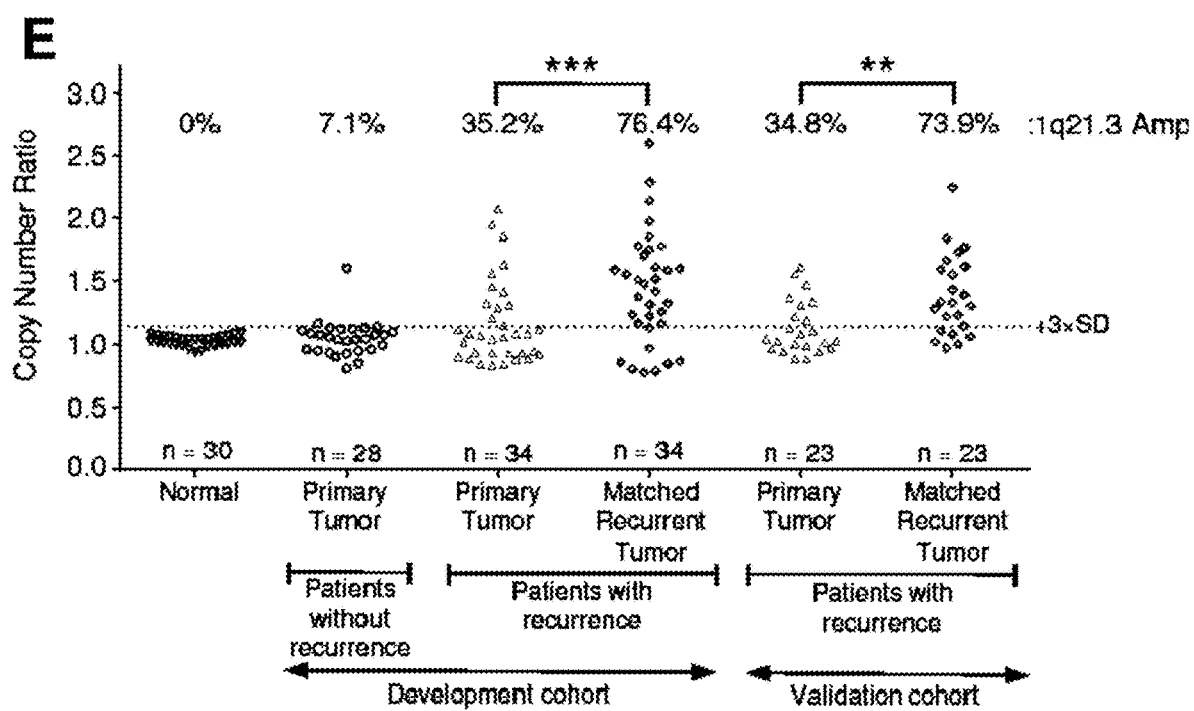

Example 2: 1q21.3 Amplification is Enriched in TICs and Associated with Tumour Recurrence To validate the relevance of 1q21.3 amplification to TICs, DNA fluorescence in situ hybridization (FISH) was performed on patient-derived tumoursphere cells by using a molecular probe to detect 1q21.3 and another probe to detect 1p32.3 as an adjacent genomic region control. DNA-FISH analysis revealed multiple copies of 1q21.3 in examined tumourspheres derived from both ER-positive and ER-negative tumours (FIG. 2A). Of note, the tumoursphere cells were highly heterogeneous with at least 3 different karyotypic clones present in each tumoursphere sample. Also, the majority of the cells quantitated had more copies of 1q21.3 compared to 1p32.3, indicating that the 1q21.3 gain in TICs was not simply a consequence of chromosome aneuploidy (FIG. 2A and Table 4 below).

TABLE 4

DNA FISH quantitation of 1q21.3 (Red - R) and 1p32.3 (Green - G)

| Samples | 2R2G | 3R3G | 4R3G | 5R3G | 5R4G | 6R3G | 6R4G | 6R5G | 6R6G | 7R3G | 7R4G | 7R5G | 8R4G | 8R6G | 12R6G | Total |
|---|---|---|---|---|---|---|---|---|---|---|---|---|---|---|---|---|
| Primary mammary epithelial | 100 | 0 | 0 | 0 | 0 | 0 | 0 | 0 | 0 | 0 | 0 | 0 | 0 | 0 | 0 | 100 |
| ER positive tumorsphere | 0 | 0 | 13 | 38 | 35 | 8 | 2 | 0 | 0 | 4 | 0 | 0 | 0 | 0 | 0 | 100 |
| ER negative tumorsphere 1 | 8 | 81 | 94 | 4 | 0 | 1 | 0 | 1 | 1 | 3 | 0 | 1 | 1 | 4 | 1 | 200 |
| ER negative tumorsphere 2 | 0 | 17 | 42 | 41 | 0 | 0 | 0 | 0 | 0 | 0 | 0 | 0 | 0 | 0 | 0 | 100 |

Cells were quantitated based on the number of both 1q21.3 and 1p32.3. A total of 100 cells were enumerated for primary mammary epithelial, ER positive tumoursphere and ER negative tumoursphere 2. 200 cells were enumerated for ER negative tumoursphere 1 due to presence of minor subclones within population.

A robust assay to detect 1q21.3 amplification was developed utilizing the highly sensitive and quantitative droplet digital PCR (ddPCR) and designing three PCR probes targeting TUFT1, S100A8 and S100A7 as a proxy to cover 1q21.3 and a control gene RPP30. The assay was able to detect 1q21.3 amplification in three positive tumours (identified in FIG. 8A) but not in the matched adjacent normal tissues (FIG. 9A), validating its specificity.

Figure 9:
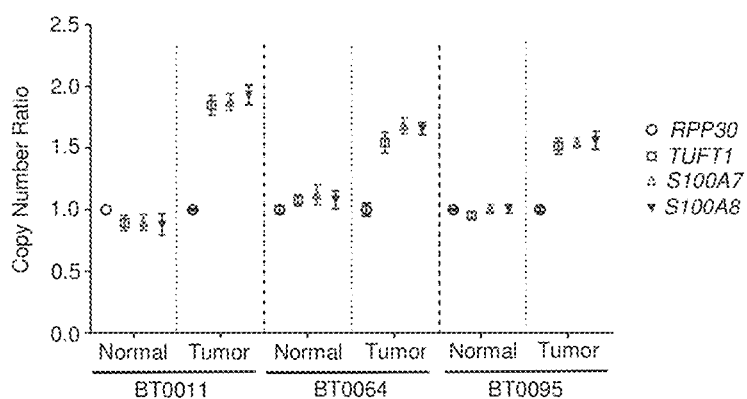
FIG. 9 (A) is a ddPCR result showing the relative copy number amplification of TUFT1, S100A8 and S100A7 genes in three positive primary tumours and matched normal adjacent tissues normalized to the control reference gene RPP30.
Figure 9:
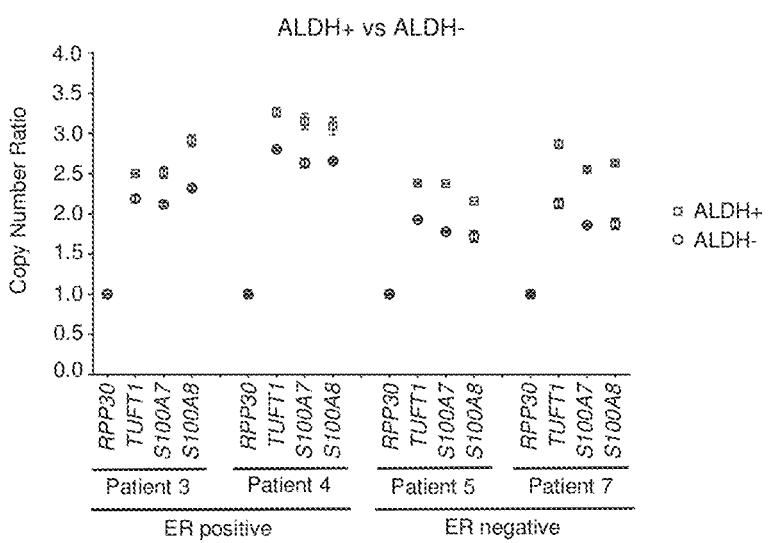
Figure 9:
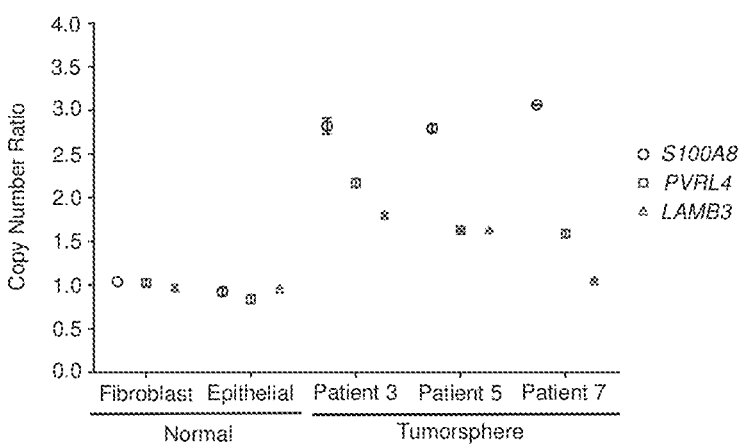

The 1q21.3 amplification in tumourspheres cultured in vitro and matched primary breast tumours were examined using this ddPCR assay. In all seven such paired samples (both ER-positive and ER-negative), tumoursphere samples displayed an enrichment of 1q21.3 amplification compared to corresponding bulk tumours (FIG. 2B). Moreover, ALDH+ tumoursphere cells sorted by fluorescence-activated cell sorting (FACS) showed further enhancement of 1q21.3 amplification compared to the ALDH− tumoursphere cells (FIG. 9B). In contrast to 1q21.3, genes located at other bands of the 1q arm, including PVRL4 at 1q23.3 and LAMB3 at 1q32.2, did not exhibit a consistent copy number gain (FIG. 9C), supporting a focal amplification of 1q21.3 in TICs.

Figure 10:
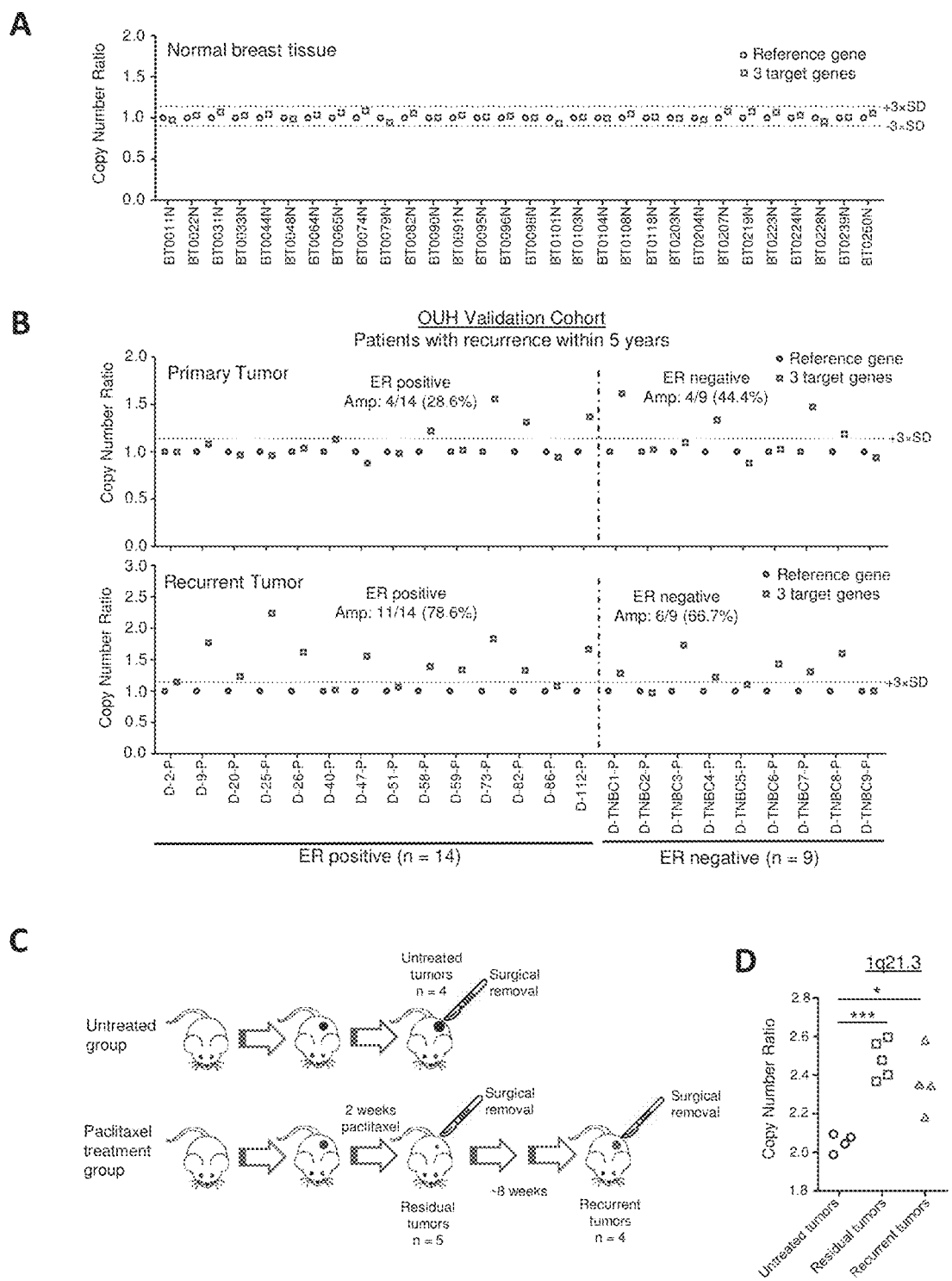
FIG. 10 (A) is a ddPCR analysis of 1q21.3 amplification in normal adjacent breast tissues from breast cancer patients.

Next, the potential of 1q21.3 amplification in predicting clinical tumour recurrence was investigated. To do this, primary tumours from patients who did not develop recurrence within 5 years and patients who developed recurrence within 5 years, together with their matched recurrent tumours, were procured. To set a cutoff value to define positive 1q21.3 amplification, averaged copy number ratios of the three genes (TUFT1, S100A8, and S100A7) relative to the control gene RPP30 from 30 normal breast tissues adjacent to breast cancer tumours were determined. A cutoff for a positive sample was set at 3× standard deviation (SD) above the mean (FIG. 10). In this case, the mean and SD of the copy number ratio in normal breast tissues were 1.0206 and 0.0396 respectively, leading to a positive CNA cutoff value of 1.139.

Using this criterion, the assay detected 2 of 28 primary tumours that were positive for 1q21.3 amplification from patients without recurrence [7.1%; 95% Cl, 1.3% to 25.0%] (FIG. 2C and FIG. 2E), while 12 of 34 primary tumours from patients with matched clinical characteristics who later developed recurrence were positive [35.3%; 95% Cl, 20.3% to 52.1%] (FIG. 2D and FIG. 2E, Table 5 below).

TABLE 5

Stage Information for FIG. 2D and FIG. 2E

| Characteristics | Patient without Recurrence Patients (n = 28) | Patient with Recurrence Patients (n = 34) |
|---|---|---|
| Stage | | |
| I | 2 (7.1%) | 5 (14.7%) |
| II | 10 (35.7%) | 8 (23.5%) |
| III | 14 (50.0%) | 14 (41.2%) |

TABLE 5-continued

Stage Information for FIG. 2D and FIG. 2E

| Characteristics | Patient without Recurrence Patients (n = 28) | Patient with Recurrence Patients (n = 34) |
|---|---|---|
| IV | 2 (7.1%) | 2 (5.9%) |
| Unknown | NA | 5 (14.7%) |

Tumour DNA samples from patients of various stages were collected to validate 1q21.3 amplification association with tumour recurrence.

Intriguingly, among 34 paired recurrent tumours, 26 were positive [76.5%; 95% Cl, 58.4% to 88.6%] (FIGS. 2D and 2E). Of note, 14 out of 34 recurrent patients (41.2%) were negative in their primary tumours but had acquired 1q21.3 amplification upon recurrence [McNemar test, p<0.001]. A similar result was obtained from another validation cohort obtained from Odense University Hospital (OUH) in Denmark (FIG. 2E and FIG. 10B). Importantly, the 1q21.3 enrichment in tumour recurrence was seen in both ER-positive and ER-negative tumours, suggesting a broad coverage of this biomarker in breast cancer patients. Statistical analysis with Pearson's chi-squared test of independence between the primary tumours of patients with and without recurrence showed a significant association between 1q21.3 amplification and tumour recurrence [p<0.008; Odds ratio: 7.091].

Figure 16:
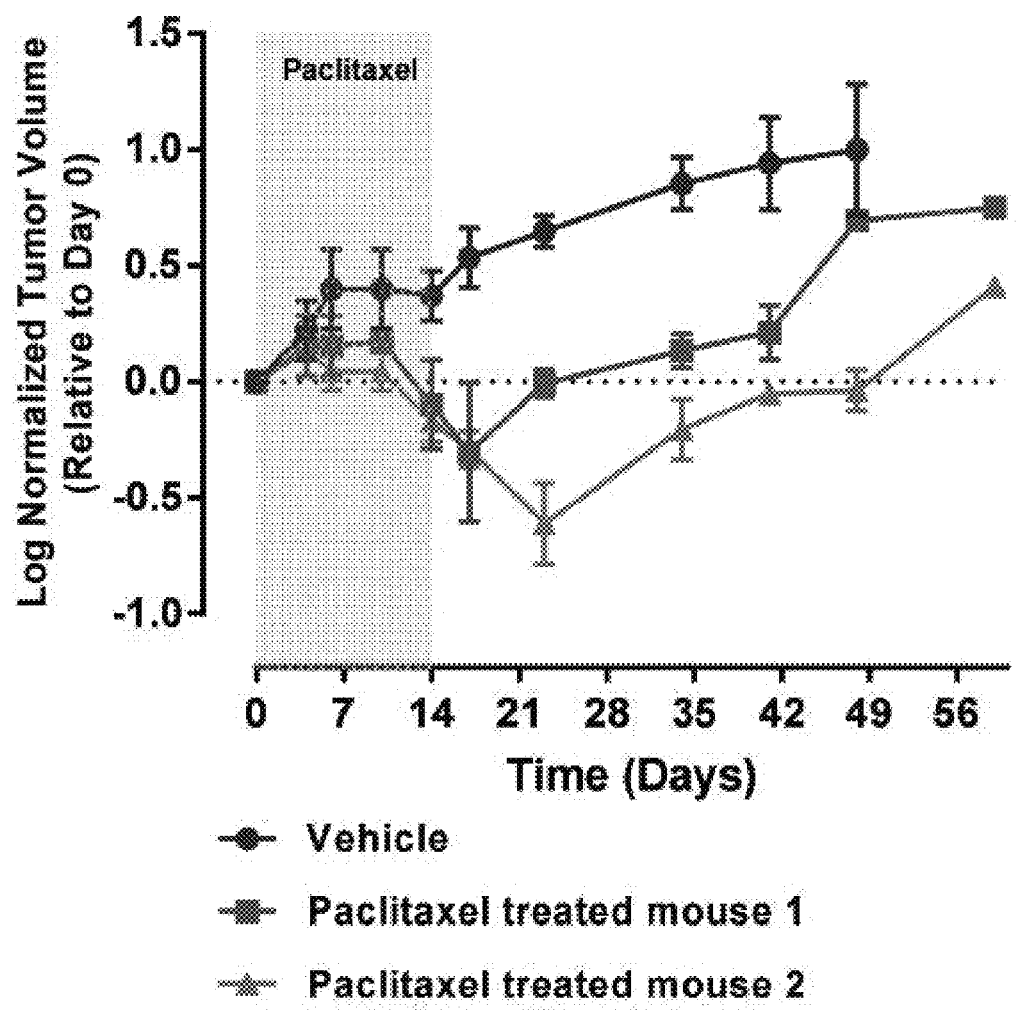
FIG. 16 is a graph of log normalized tumour volume against time with respect to the PDX mouse model. NOD-SCID mice bearing breast PDX tumour were treated with vehicle or 20 mg/kg paclitaxel for 14 days. Recurrent PDX tumours were harvested when the tumour volume reached ~800 mm$^3$.
Figure 17:
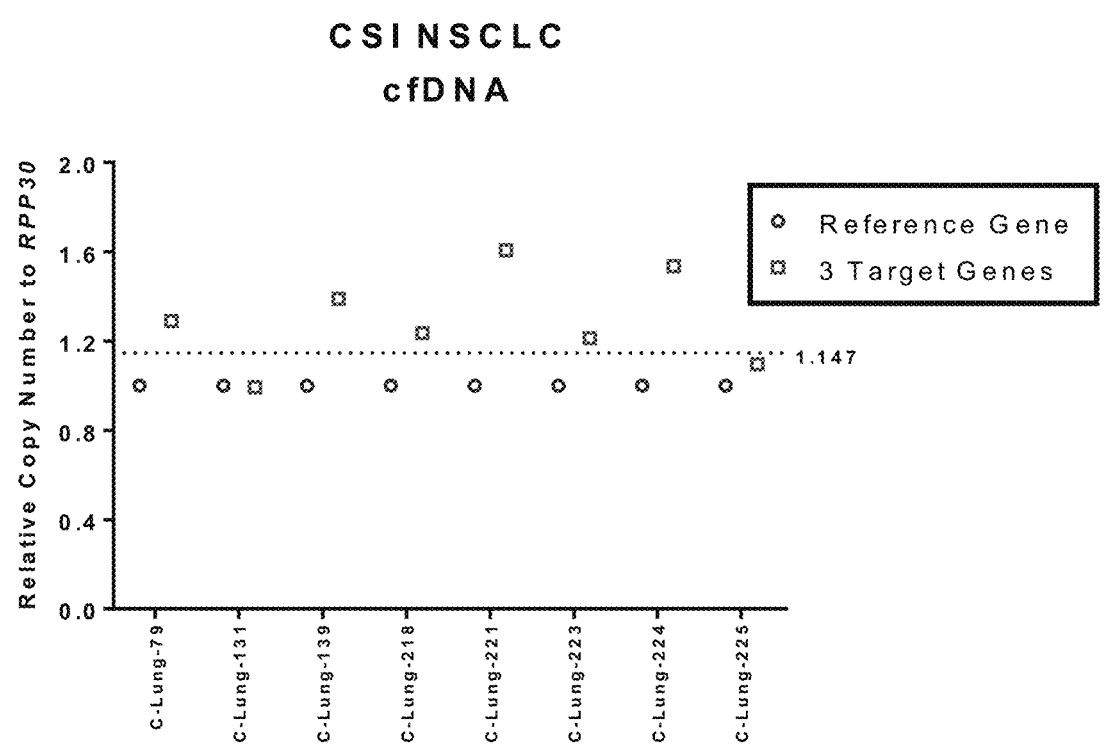
FIG. 17 shows the chromosome 1q21.3 copy number amplification analysis results based on the circulating free DNA of patients suffering from metastatic non-small cell lung cancer (NSCLC). TaqMan probes were designed for each of the four genes S100A7, S100A8, TUFT1 and RPP30 for use with their primer pairs in a ddPCR assay. The probe for the reference gene RPP30 was labelled with the fluorophore HEX while the probes for the three other target genes S100A7, S100A8, TUFT1 were labelled with the fluorophore FAM to allow duplex reaction in the ddPCR. The results showed that 6 out of 8 metastatic cfDNA samples (75%) have copy number amplification of chr1q21.3.

Moreover, a breast cancer patient-derived xenograft (PDX) mouse model was also used to test if 1q21.3 amplification is associated with tumour recurrence following chemotherapy. To this end, PDX tumours were engrafted orthotopically into the mammary fat pad of NOD-SCID mice and upon the formation of the tumours (100 mm$^3$), the mice were treated with 20 mg/kg of paclitaxel for 2 weeks to induce tumour regression (FIG. 16), before the tumours were surgically removed, and the mice were subsequently monitored for tumour recurrence (FIG. 10C). The recurrent tumours harvested at day 56 after treatment termination and considered to arise from paclitaxel-resistant cancer cells, were examined for chr1q21.3 CNA. Indeed, ddPCR analysis revealed that both residual tumours post-paclitaxel treatment and recurrent tumours showed marked enrichment of 1q21.3 amplification compared to treatment naive PDX tumours (FIG. 10D). This result indicates that 1q21.3 amplification is associated with acquired resistance to chemotherapy and tumour recurrence.

Figure 11:
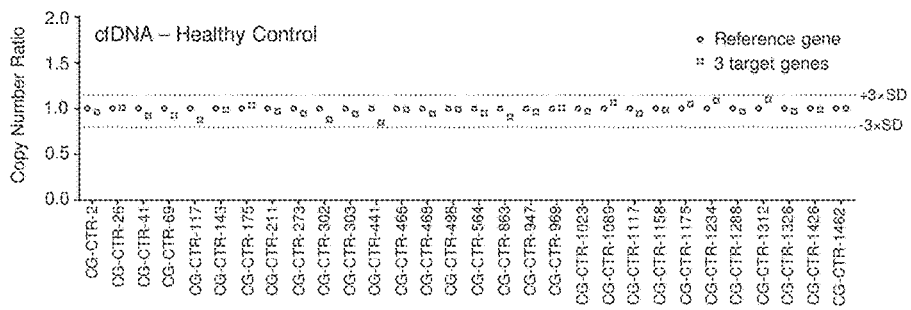
FIG. 11 (A) is a ddPCR analysis of cfDNA isolated from healthy female blood to establish normal baseline. Shown are the averaged ratios of the three target genes TUFT1, S100A8 and S100A7 relative to the reference gene RPP30. Cutoff value for positive 1q21.3 amplification is determined (3× SD above mean).
Figure 11:
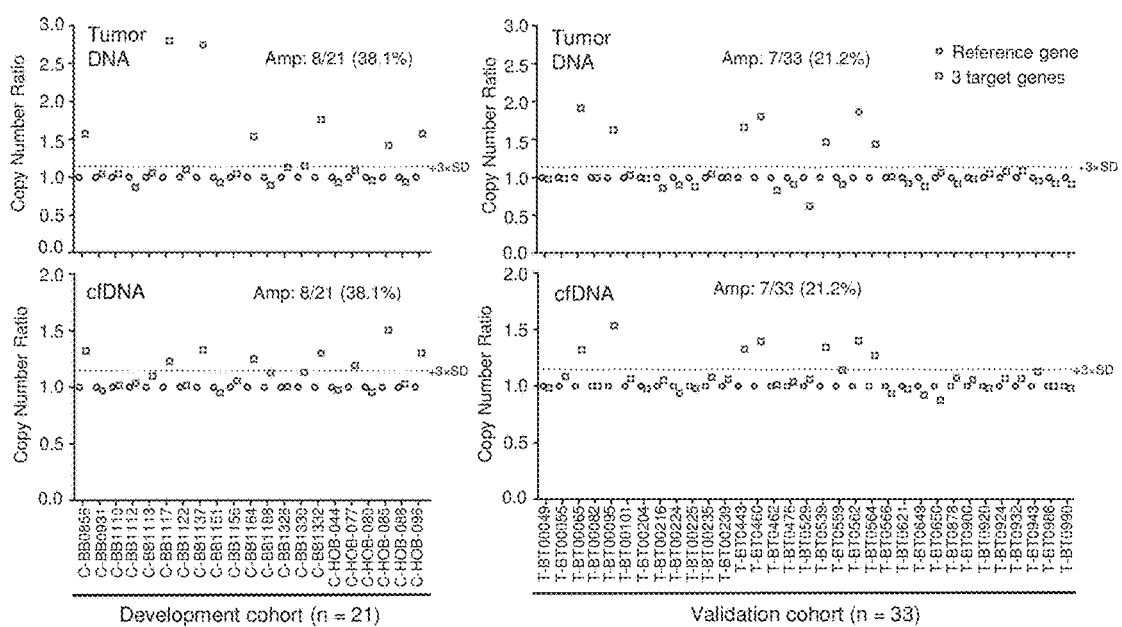

Example 3: Blood-Based Cell Free DNA Detection of ch1q21.3 in Patients at Diagnosis and Recurrence To assess whether the ddPCR assay may be implemented as a liquid biopsy diagnostic, the ddPCR assay was evaluated for its ability to detect 1q21.3 amplification in the circulating free DNA (cfDNA) of patient's blood. To this end, a ddPCR assay was performed using the plasma from 30 healthy women to determine the background and cutoff value (FIG. 11A). Similar to what was performed for tumour DNA, the copy number ratio of the three genes (TUFT1, S100A8 and S100A7) were averaged before applying 3×SD to the mean of the averaged copy number ratios, resulting in a cutoff value of 1.147 in the case of cfDNA.

Figure 3:
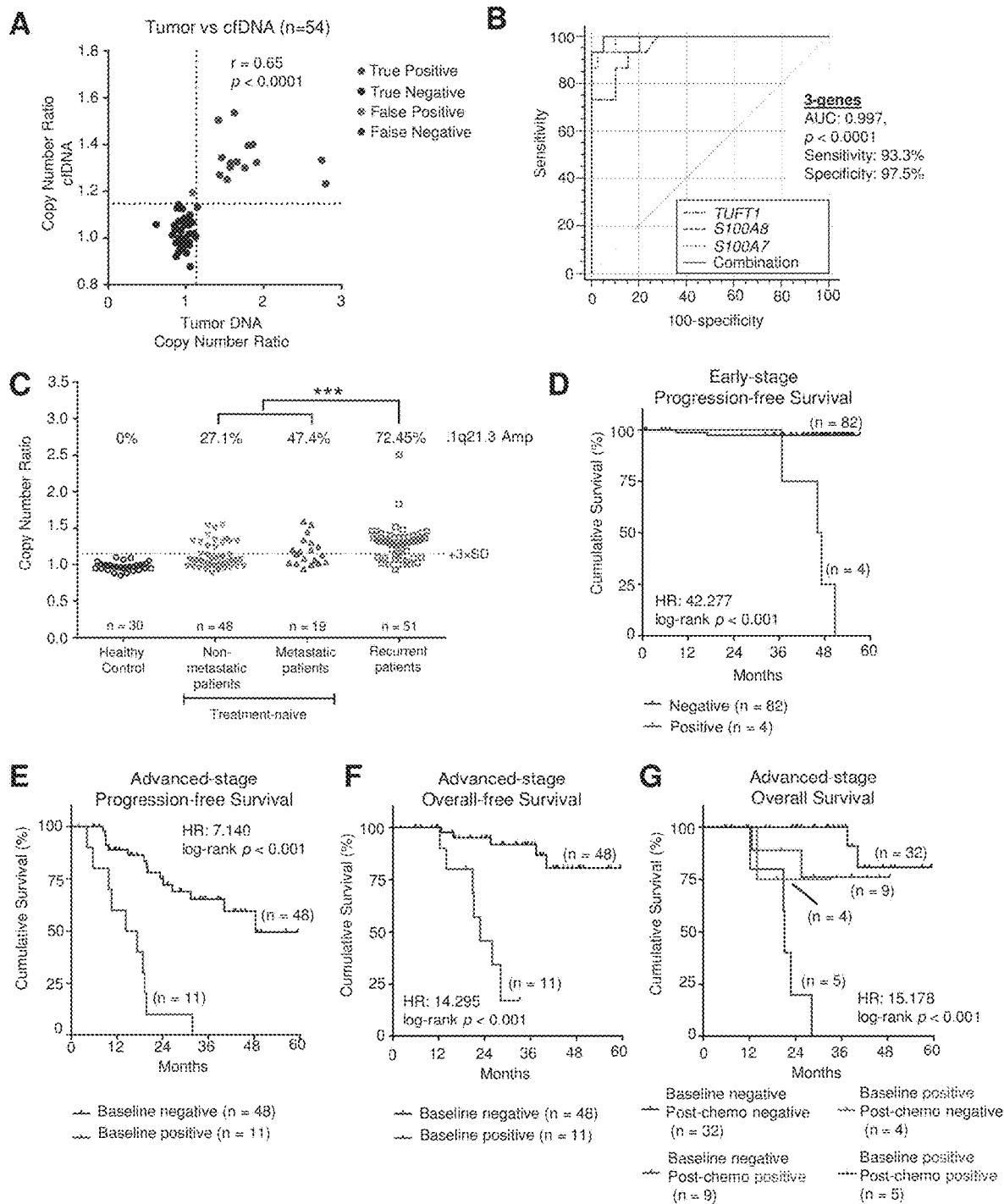
FIG. 3 shows that cfDNA detection of 1q21.3 amplification is associated with recurrence and predicts poor patient outcome. (A) Correlation analysis between tumour DNA and cfDNA in both development and validation cohort. Red dots: True positive, Blue dots: True negative, Green dots: False positive, Purple dots: False negative. (B) Individual genes (TUFT1, S100A8 and S100A7) and 3-genes (Combination) Receiver Operating Characteristic (ROC) curves for the detection of 1q21.3 amplification in 54 breast cancer patients (development and validation cohort) were generated. The Area Under Curve (AUC) value for 3-genes combination is 0.997 [95% CI, 0.927 to 1.00, $p<0.0001$]. The dotted diagonal line denotes an AUC=0.50. (C) Scatter plot showing the 1q21.3 amplification in the cfDNA of healthy control patients as well as breast cancer patients at the time of diagnosis and time of recurrence. p-value was calculated with Mann-Whitney test. *** $p<0.001$. (D) Kaplan-Meier progression-free survival analysis of Denmark OUH early-stage breast cancer patients with or without 1q21.3 amplification in cfDNA at the time of diagnosis. (E) Kaplan-Meier progression-free survival analysis of Singapore NUHS advanced-stage breast cancer patients with or without 1q21.3 amplification in cfDNA at the time of diagnosis (baseline). (F) Kaplan-Meier overall survival analysis of Singapore NUHS advanced-stage breast cancer patients with or without 1q21.3 amplification in cfDNA at the time of diagnosis (baseline). (G) Kaplan-Meier overall survival analysis of Singapore NUHS advanced-stage breast cancer patients with cfDNA analyzed at both baseline and post-chemotherapy.

Subsequently, matching tumours and blood plasma samples from breast cancer patients in two different cohorts were used to test the assay's accuracy. In the first development cohort of 21 patients, the assay detected 8 primary tumour samples that were positive for 1q21.3 amplification, 7 of which their plasma samples were also positive for 1q21.3 amplification (FIG. 3A and FIG. 11B). Overall, only one false-positive and one false-negative in the 21 plasma samples tested were obtained. In the second independent cohort of 33 patients for verification, the assay detected 7 positive patients in both their primary tumours and corresponding plasma samples in their blood, with 100% tumour-plasma concordance (FIG. 3A and FIG. 11B). Overall, the prevalence of breast cancer patients with CNA of chr1q21.3 was determined to be 27.8% [15 out of 54 patients; 95% CI, 16.9% to 41.9%]. Therefore, the ddPCR assay using plasma cfDNA was able to detect 1q21.3 amplification with a sensitivity of 93.3% and a specificity of 97.5%. The analysis of the combined cohorts by receiver operating characteristic (ROC) curve showed an increased AUC of 0.997 when using the three gene average [95% CI, 0.927 to 1.00, p<0.0001] compared to individual genes (FIG. 3B). These data indicate the robustness of the digital PCR assay in detecting the CNA of chr1q21.3 in patients' blood.

The cfDNA assay was next used to assess 1q21.3 amplification in metastatic progression. In 51 plasma samples collected from breast cancer patients upon metastatic recurrence after chemotherapy, 37 were positive for 1q21.3 amplification [72.5%, 95% CI, 58.0% to 83.7%], which was much higher than those collected at initial diagnosis before any treatment (p<0.0001, Mann-Whitney test). Moreover, among treatment-naive samples, metastatic patients showed more positive samples compared to non-metastatic patients (47.4% vs. 27.1%) (FIG. 3C). Together, these findings established the association of 1q21.3 amplification in disease progression and highlighted the value of 1q21.3 as a potential circulating biomarker for clinical metastasis and relapse of breast cancer.

Example 4: cfDNA Detection of CNA of chr1q21.3 is Highly Prognostic in Both Early and Late Stage Breast Cancer Patients Next, the cfDNA assay was tested for its ability to predict the clinical outcomes of breast cancer patients. The assay was investigated on whether it is sensitive enough in early-stage breast cancer patients as the abundance of circulating tumour DNA (ctDNA) in early stage patients is known to be much lower (by approximately 10 fold) than in advanced patients. The cfDNA assay was performed for 86 newly diagnosed breast cancer patients from a Denmark cohort in which the majority of the patients were at Stage I and II (Denmark early-stage breast cancer cohort). The clinical pathological characteristics of these patients are shown in Table 6 below.

TABLE 6

Clinical pathological characteristics of Denmark OUH early stage breast cancer cohort
Denmark OUH Early-Stage Breast Cancer Cohort

| Characteristics | Patients (n = 86) |
| --- | --- |
| Age | |
| <41 | 2 |
| 41-50 | 9 |
| 51-60 | 25 |
| >60 | 48 |
| Unknown | 2 |
| Tumor size | |
| pT1 (<2.0 cm) | 54 |
| pT2 (2.0 to 5.0 cm) | 31 |
| pT3 (>5.0 cm) | 1 |
| Stage | |
| I | 54 |
| II | 24 |
| III | 6 |
| Unknown | 2 |
| Malignancy Grade | |
| 1 | 29 |
| 2 | 30 |
| 3 | 17 |
| Unknown | 10 |
| Lymph node status | |
| pN0 | 52 |
| pN1 | 27 |
| pN2 | 4 |
| pN3 | 1 |
| Unknown | 2 |
| Subtype | |
| ER+ | 72 |
| HER2+ | 3 |
| TNBC | 6 |
| Unknown | 5 |

In the cohort of 86 patients, 4 were positive in their cfDNA and remarkably all these 4 patients had disease relapse within 5 years [HR: 42.277; 95% CI, 7.660 to 233.336; log-rank p<0.001] (FIG. 3D). Overall, 6 patients developed relapse within 5 years in this cohort.

The cfDNA assay was then tested for its ability to predict the clinical outcomes of advanced-stage patients. Plasma samples from a cohort of patients consisting of newly diagnosed advanced stage breast cancer patients undergoing neoadjuvant chemotherapy were obtained and analyzed for their cfDNA before chemotherapy (baseline) and after chemotherapy (post-chemo) to evaluate the survival outcome of the patients (Singapore NUHS advanced-stage breast cancer cohort). The clinical pathological characteristics of these patients are shown in Table 7 below.

TABLE 7

Clinical pathological characteristics of Singapore NUHS advanced-stage breast cancer cohort
Singapore NUHS Advanced-Stage Breast Cancer Cohort

| Characteristics | Patients (n = 59) |
| --- | --- |
| Age | |
| <41 | 9 |
| 41-50 | 22 |

TABLE 7-continued

Clinical pathological characteristics of
Singapore NUHS advanced-stage breast cancer cohort
Singapore NUHS Advanced-Stage Breast Cancer Cohort

| Characteristics | Patients (n = 59) |
|---|---|
| 51-60 | 20 |
| >60 | 8 |
| Tumor size | |
| cT1 (<2.0 cm) | 2 |
| cT2 (2.0 to 5.0 cm) | 23 |
| cT3 (>5.0 cm) | 19 |
| cT4 | 15 |
| Stage | |
| I | 0 |
| II | 26 |
| III | 26 |
| IV | 7 |
| Malignancy Grade | |
| 1 | 3 |
| 2 | 20 |
| 3 | 32 |
| Unknown | 4 |
| Subtype | |
| ER+ | 47 |
| HER2 | 1 |
| TNBC | 11 |
| Lymph node status | |
| cN0 | 30 |
| cN1 | 12 |
| cN2 | 11 |
| cN3 | 5 |
| cNx | 1 |
| Race | |
| Chinese | 40 |
| Malay | 14 |
| Indian | 2 |
| Others | 3 |

Analysis of the baseline cfDNA samples identified 11 patients who were positive for 1q21.3 amplification and 10 of them developed relapse [HR: 7.140; 95% CI, 3.006 to 16.960; log-rank p<0.001] (FIG. 3E) and 7 died [HR: 14.295; 95% CI, 3.621 to 56.441; log-rank p<0.001] (FIG. 3F) within three years of initial diagnosis. Further analysis of the four patients with baseline positive samples who survived so far showed that three of the patients had negative post-chemotherapy cfDNA samples (copy number ratio<1.140), suggesting that they might have responded well to the chemotherapy. When assessing both baseline and post-treatment plasma samples, patients whose baseline and post-treatment samples were both positive all relapsed and died (5 of 5 patients) within three years of initial diagnosis [HR: 15.178; 95% CI, 4.217 to 54.625; log-rank p<0.001] (FIG. 3G). Similar to the previous study cohort, univariate analysis showed that CNA status diagnosed from circulating cfDNA of patients was a statistically significant prognostic predictor of survival ($x^2$=24.396, p<0.001). Further multivariate analysis demonstrated that cfDNA detection of 1q21.3 amplification was a strong and independent predictor of survival outcome in advanced-stage breast cancer [HR: 25.34, 95% CI, 2.40 to 267.66, p=0.007] (see Table 8 below).

TABLE 8

Multivariate Cox regression analysis of 1q21.3 amplification status
for overall survival of Singapore NUHS advanced-stage cohort

| Clinical variable | HR | Baseline cfDNA 95% CI | p-value |
|---|---|---|---|
| CNA status (Negative vs Positive) | 25.341 | 2.399 to 267.657 | 0.007 |
| ER status (Negative vs Positive) | 0.145 | 0.017 to 1.224 | 1.224 |
| HER2 status (Negative vs Positive) | 3.925 | 0.120 to 128.274 | 0.442 |
| Tumor size (T1-2 vs T3-4) | 1.036 | 0.129 to 8.338 | 0.973 |
| Lymph nodes (N0 vs N1-3) | 0.62 | 0.083 to 4.614 | 0.641 |
| Metastatic status (M0 vs M1) | 3.919 | 0.118 to 130.359 | 0.445 |

Taken together, cfDNA detection of 1q21.3 amplification using blood has provided a potential liquid biopsy to identify high-risk patients who might suffer an early relapse. It also indicates that 1q21.3 amplification can identify a group of patients with particularly aggressive disease, in whom the current chemotherapy regimens appear inadequate, and may be candidates for additional and/or alternative treatments.

Figure 12:
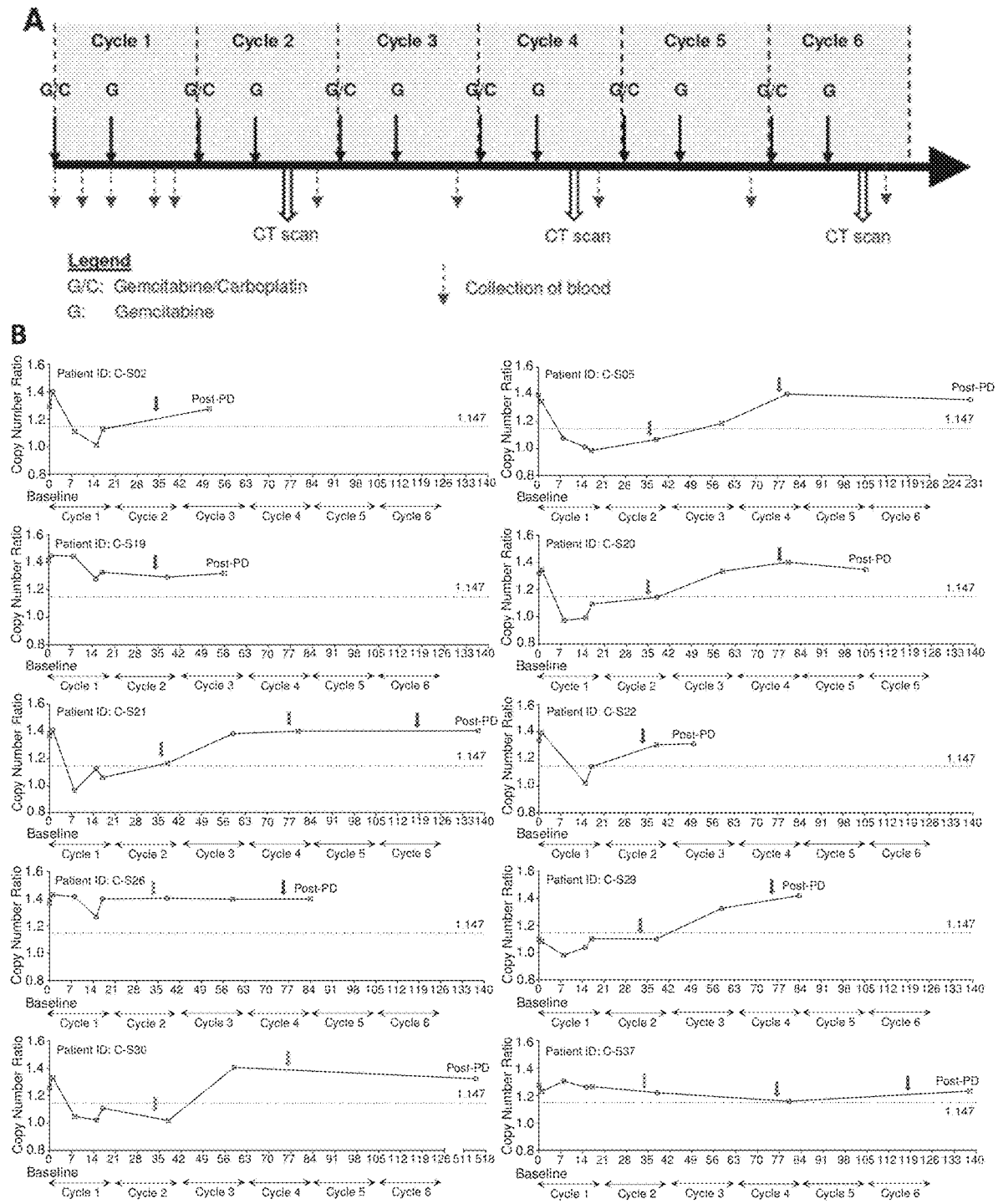
FIG. 12 shows the cfDNA detection of 1q21.3 amplification in the course of chemotherapy. (A) Schematic illustration of the gemcitabine and carboplatin chemotherapy regimen. (B) Serial ddPCR analysis of cfDNA of metastatic breast cancer patients treated with gemcitabine and carboplatin chemotherapy regimen in a phase II clinical study. Patients were treated with gemcitabine (day 1 and 8) and carboplatin (day 1) every 3-week for a maximum of 6 cycles. Blood samples were taken at the baseline time point before the treatment and indicated time points during the course of treatment. CT scans were performed after every 2 cycles as denoted by the colored arrows. Patients stopped treatment when their CT scan show disease progression. Green arrow indicates partial response, yellow arrow indicates stable disease, and red arrow indicates progressive disease.

Example 5: cfDNA Detection of 1q21.3 Monitors the Dynamic Tumour Response to Chemotherapy To determine the potential utility of 1q21.3 cfDNA assay to monitor tumour response to treatment, the blood samples from a retrospective cohort of refractory metastatic breast cancer patients in a Phase II study were examined. In this Phase II study, patients were administered with gemcitabine and carboplatin for a maximum of 6 cycles and blood samples were collected prior to the start of every new cycle and also on day 1, day 8 and day 15 of the first cycle (FIG. 12A). Patients stopped treatment if they were deemed to have disease progression as evaluated with radiological computerized tomography (CT) scans performed every 6 weeks.

Among the 29 patients in this study, 22 were found to be positive for 1q21.3 amplification at the baseline level (before gemcitabline and carboplatin treatment). Among the 22 positive patients, 10 patients had serial blood samples available from start of chemotherapy to disease progression. cfDNA from the serial samples were analyzed for chr1q21.3 amplification (FIG. 12B). Most of the patients except one (C-S29) had positive 1q21.3 amplification at baseline and became negative by day 8 or of cycle 1 treatment, indicating a decrease in tumour burden and initial drug response. However, cfDNA marker showed a trend of rebound in most of the patients by cycle 2 or cycle 3, although CT scans of some patients (C-S05, C-S20, C-S21, C-S29) showed the partial radiological response of the tumours. On the other hand, 3 patients (C-S26, C-S37, C-S30) with CT scan evaluation of stable disease at the end of cycle 2 showed no change or decrease in cfDNA marker, while all patients who had progressive disease despite chemotherapy showed either persistent or rebound cfDNA marker during the later cycles of treatment which preceded radiological evidence of tumour progression by CT scan. Particularly, two patients, (C-S05, C-S21) showed return of copy number ratio to baseline level at the end of cycle 4 but CT scan showed partial drug response, though these two patients eventually have disease progression at the end of cycle 6. These results suggested that the cfDNA detection of 1q21.3 amplification could be an early indication of chemoresistance and can detect radiologically occult disease. Taken together, these results demonstrate the potential application of the cfDNA assay, as a more favourable alternative to conventional radiological scans, to track and monitor early tumour response. The TICs-associated cfDNA assay may prove valuable by enabling early decision making during disease monitoring, such that clinicians and patients may explore other treatment alternatives to prolong the survival of patients.

Example 6: 1q21.3-Encoded S100A7/8/9 and IRAK1 Forms a Functional Regulatory Circuitry to Drive Tumoursphere Growth To identify therapeutic solutions which can target 1q21.3-amplified tumours, the functionality of 1q21.3 amplification in breast cancer, particularly in relation to IRAK1 activation and tumoursphere growth, was investigated. 1q21.3 harbours up to 17 members of S100A gene family, and several of them have been previously implicated in breast cancer progression. Moreover, some S100A proteins have been shown in other contexts to act upstream of Toll-like receptor (TLR) signaling to induce activation of IRAK/NF-κB signaling. The inventors have also found out that increased IRAK1 phosphorylation is associated with breast cancer recurrence and IRAK1-directed NF-κB signaling plays an important role in breast cancer metastasis, chemoresistance and tumour recurrence.

Figure 4:
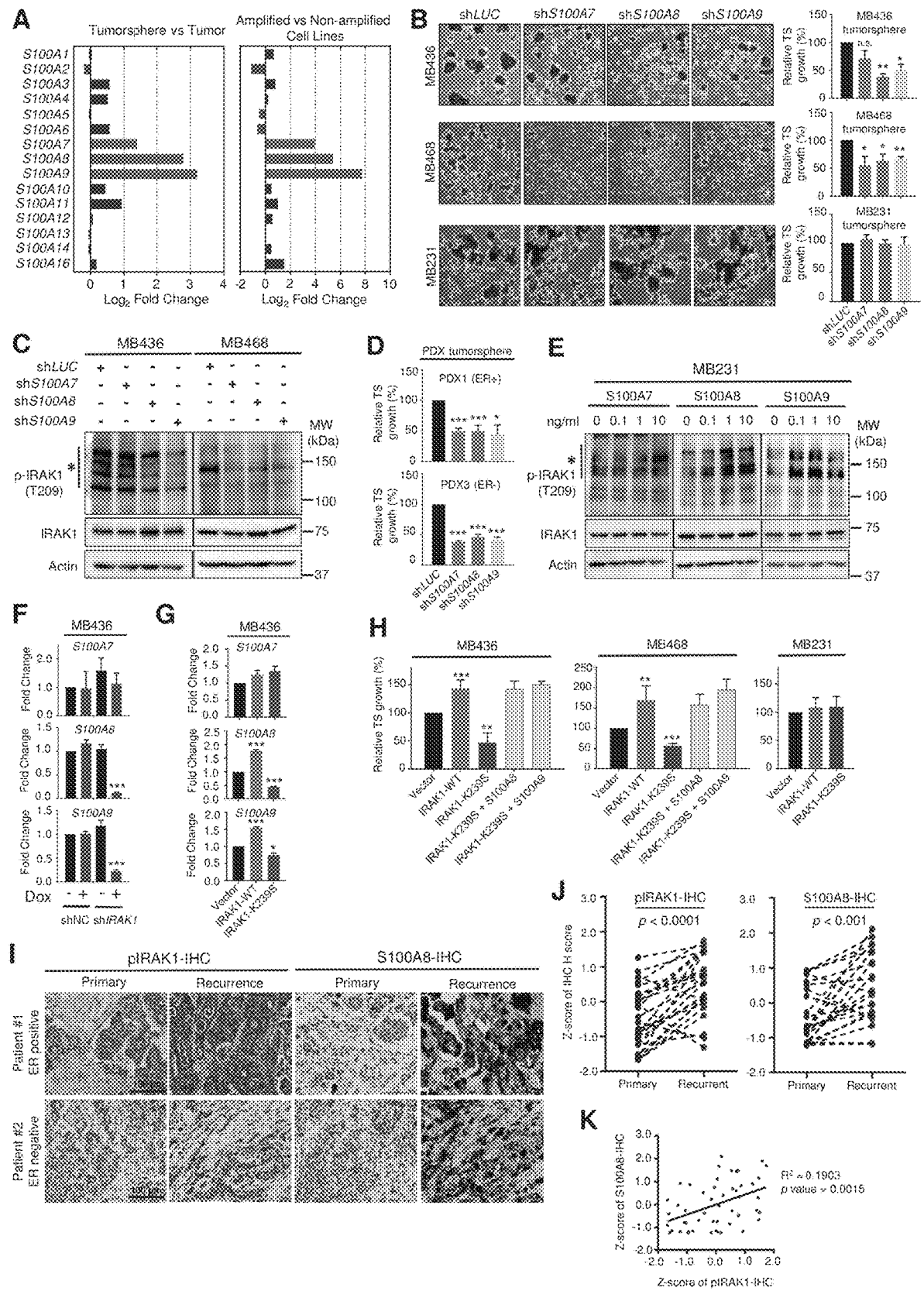
FIG. 4 shows that 1q21.3-encoded S100A7/8/9 forms a functional feedback loop with IRAK1 to drive tumoursphere growth. (A) Microarray gene expression analysis of S100A family members in tumour versus its derivative tumoursphere (left panel), and 1q21.3 non-amplified (BT549, BT474, MB361, MB231) versus amplified (MB436, MB468, MCF7, T47D) breast cancer cell lines (right panel). (B) Representative images and quantification of the number of tumourspheres after single knockdown of S100A7/8/9 in MB436, MB468 and MB231. Data are expressed as means±s.e.m. of three independent experiments. (C) Representative western blot showing a reduction of phospho-IRAK1 in MB436 and MB468 cells upon single shRNA knockdown of S100A7/8/9. Actin was used as loading control. (D) Quantification of the number of tumourspheres after single knockdown of S100A7/8/9 in two different PDX-derived tumourspheres. Data are expressed as means±s.e.m. of three technical replicates. (E) Representative western blot showing induction of phospho-IRAK1 upon treatment of individual S100A7/8/9 recombinant protein in MB231 at indicated concentrations. Actin was used as loading control. (F) Real-time PCR analysis of S100A7/8/9 gene expression after inducible knockdown of IRAK1 in MB436 tumoursphere cells. Data are expressed as means±s.d. of three technical replicates. (G) Real-time PCR analysis of S100A7/8/9 gene expression after overexpression of IRAK1 wild-type (WT) and K239S mutant in MB436 tumoursphere cells. Data are expressed as means±s.d. of three technical replicates. (H) Quantification of the number of tumourspheres after overexpression of IRAK1 wild-type (WT) and K239S mutant in MB436, MB468 and MB231 cells. S100A8 and S100A9 recombinant protein were added separately to K239S IRAK1 mutant to rescue tumoursphere formation. Data are expressed as means±s.e.m. of three independent experiments. (I) Representative IHC images of phospho-IRAK1 (S376) and S100A8 in matched primary and recurrent breast tumour samples. Scale bar, 100 μm. (J) IHC analysis of phospho-IRAK1 (S376) and S100A8 in matched primary and recurrent breast tumour samples. Quantification of phospho-IRAK1 and S100A8 levels in 25 paired tumour samples (paired two-tail t-tests). (K) Correlation analysis of S100A8 and phospho-IRAK1 IHC staining. Linear regression was determined using GraphPad Prism. The linear regression Pearson's correlation coefficient ($R^2$) and its p-value are indicated. All p-values were calculated with two-tailed t-tests. * $p<0.05$,  $p<0.01$, * $p<0.001$.
Figure 6:
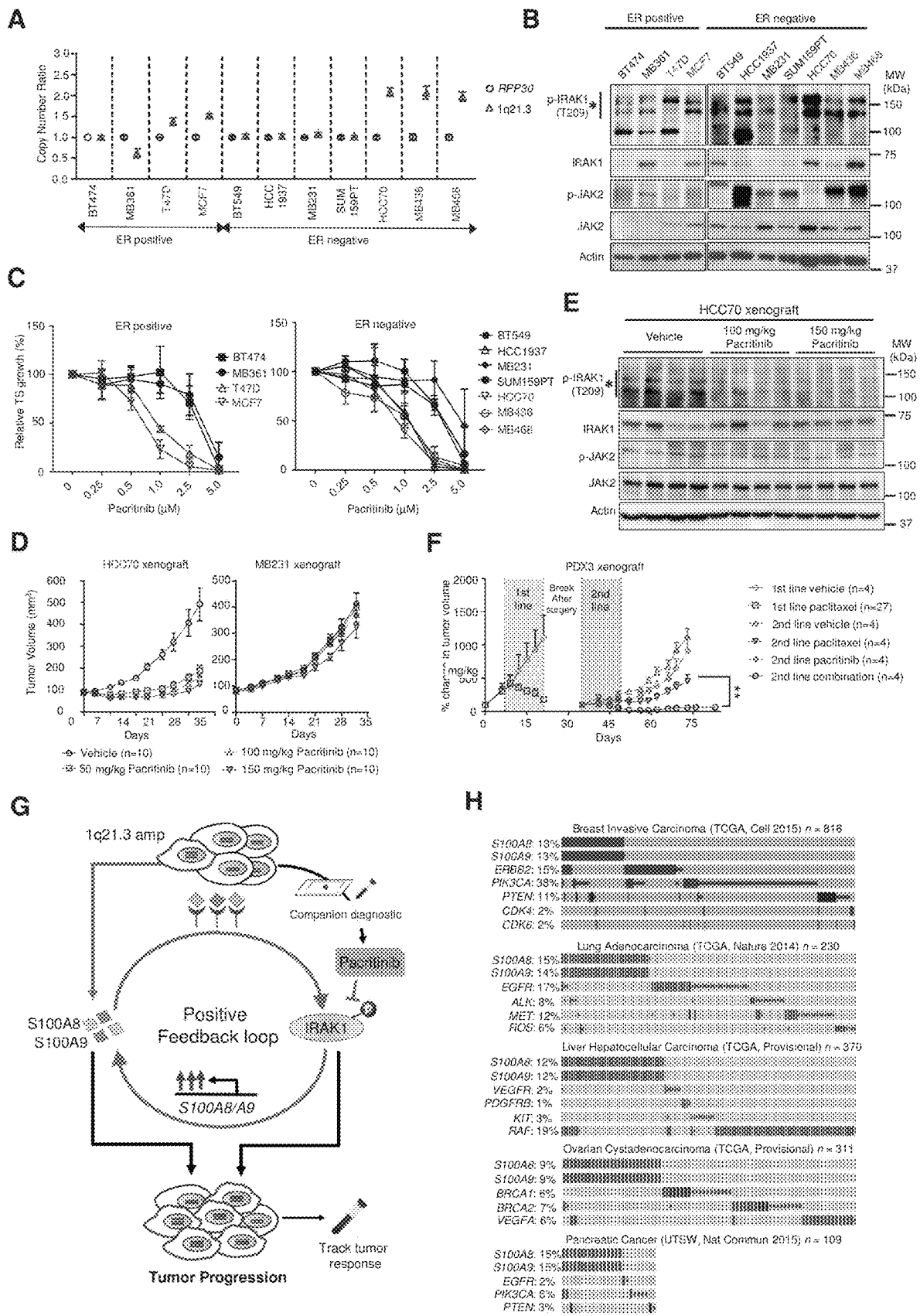
FIG. 6 shows that 1q21.3 amplification status correlates with the efficacy of pacritinib in vitro and in vivo. (A) ddPCR analysis of genomic DNA of various breast cancer cell lines to determine the status of 1q21.3. (B) Representative western blot showing phospho-IRAK1 and phospho-JAK2 levels in the breast cancer cell lines in (A). Actin was used as loading control. (C) Growth curve of ER positive and ER negative breast cancer cell lines tumourspheres treated with increasing dose of pacritinib. Red line: Amplified, Black line: Non-amplified. Data are expressed as means±s.e.m. of three independent experiments. (D) NOD-SCID mice bearing MB231 and HCC70 tumours were treated with 50, 100 and 150 mg/kg pacritinib by oral gavage. (E) Western blot analysis of phospho-IRAK1 level in HCC70 xenograft (n=4) treated with pacritinib. (F) NOD-SCID mice bearing EL12-58 PDX tumours were treated with 20 mg/kg paclitaxel by intravenous tail-vein injection for 14 days to induce tumour regression. The residual tumours were surgically removed and rested for 14 days before treatment with 20 mg/kg paclitaxel, 150 mg/kg pacritinib or combination of both. p-value was calculated with two-tailed unpaired t-tests. ** $p<0.01$ (G) Schematic representation of the proposed mechanisms of an S100A8/9-IRAK1 feedback loop in 1q21.3 amplified tumours, as well as the application of 1q21.3 amplification as a biomarker for companion diagnostic and tracking tumour response. (H) Genomic alterations of S100A8, S100A9 (1q21.3) and genes with targeted therapy in various TCGA cancer databases.
Figure 13:
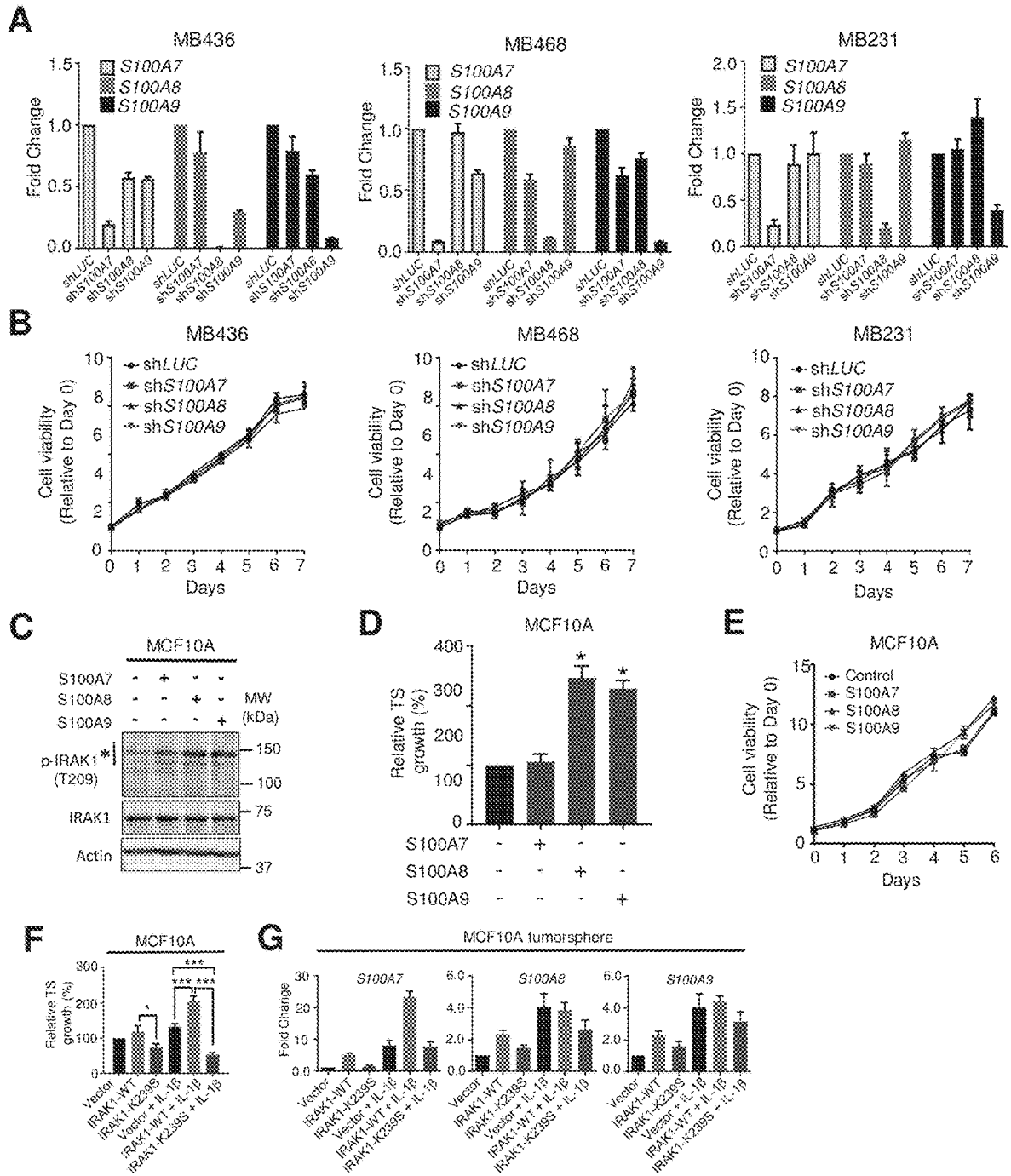
FIG. 13 (A) is a Real-time RT-PCR analysis of shRNA knockdown efficiency in MB231, MB436 and MB468 cell lines. Data are expressed as means±s.d. of three technical replicates.

In a series of PDX ex vivo tumoursphere and breast cancer cell line models, S100A7, S100A8, and S100A9, but not other family members, consistently showed gene up-regulation in 1q21.3 amplified tumourspheres or breast cancer cell lines compared to the corresponding bulk tumours or 1q21.3 non-amplified cancer cell lines respectively (FIG. 4A, also see FIG. 6A). This observation suggested a close correlation of S100A7/8/9 expression with 1q21.3 amplification. Efficient knockdown of S100A7, S100A8 or S100A9 in 1q21.3-amplified MDA-MB-436 (thereafter named MB436) and MDA-MB-468 (thereafter named MB468) cells (FIG. 13A) was sufficient to impair the tumoursphere growth (FIG. 4B), as well as IRAK1 phosphorylation (FIG. 4C), though the effect of S100A7 knockdown only had a modest effect on MB436 cells due to a low level of S100A7 expression in this line. By contrast, these knockdowns did not seem to affect MDA-MB-231 (thereafter named MB231) which does not harbour the 1q21.3 amplification (FIG. 4B). Similarly, knockdown of S100A7, S100A8 or S100A9 also effectively abolished the PDX-derived tumoursphere growth (FIG. 4D). Notably, the above knockdown did not affect the proliferation of these cancer cell lines cultured in monolayer, regardless of 1q21.3 status (FIG. 13B), suggesting that the impairment of tumoursphere growth upon knockdown of S100A7/8/9 was not a consequence of reduced cell proliferation. These findings demonstrated a preferential role of S100A7/8/9 in the growth of TICs with 1q21.3 amplification. In addition, treatment of MB231 cells with as low as 1 ng/ml recombinant S100A7, S100A8 or S100A proteins was able to induce IRAK1 phosphorylation (FIG. 4E). Moreover, when MCF10A was treated long-term with recombinant S100A7/8/9 proteins individually for 10 days, increased IRAK1 phosphorylation and increased mammosphere formation in cells treated with S100A8 or S100A9 (FIG. 13C and FIG. 13D) were observed. No obvious effect was observed in monolayer growth of MCF10A cells (FIG. 13E). Conversely, exploration of the functional activity of IRAK1 towards regulating S100A7/8/9 revealed that IRAK1 might also regulate the expression of S100A7/8/9. Inducible IRAK1 knockdown in MB436 tumourspheres resulted in downregulation of S100A8 and S100A9 expression, though the S100A7 expression was not affected (FIG. 4F). Ectopic overexpression of a kinase-dead IRAK1 (K239S) in MB436 cells resulted in downregulation of S100A8 and S100A9, while overexpression of a wild-type IRAK1 led to their induction (FIG. 4G), thereby demonstrating that IRAK1 kinase activity is required for regulating the expression of S100A7/8/9. Accordingly, the K239S mutant IRAK1 compared to WT IRAK1 inhibited the tumoursphere growth in 1q21.3-amplified MB436 and MB468 but not in MB231 cells (FIG. 4H). The addition of S100A8 or S100A9 recombinant protein in the culture medium of K239S mutant cells was able to rescue the tumoursphere growth (FIG. 4H). Moreover, overexpression of WT IRAK1 but not K239S mutant IRAK1 in non-cancerous breast epithelial cell line MCF10A led to increased tumoursphere formation and upregulation of S100A7/8/9 expressions, which was more evident in the presence of IL-1β treatment (FIGS. 13F and 13G). These studies through both loss and gain-of-function experiments in various cellular models established a functional regulatory circuitry between S100A7/8/9 and IRAK1 signaling in driving tumoursphere growth. Of note, it also suggests that S100A8/9 promotes tumoursphere growth through both IRAK1 (via feedback regulation) and IRAK1-independent manner (FIG. 6G). Furthermore, in 25 paired primary and recurrent tumour samples including 17 ER positive and 8 ER negative tumours, immunohistochemistry (IHC) analysis showed that 88% and 80% of patients showed increased phospho-IRAK1 and S100A8 expression, respectively, in their recurrent tumours compared to the corresponding primary tumours (FIG. 4I and FIG. 4J), and that phospho-IRAK1 was significantly correlated with S100A8 expression (FIG. 4K). These results indicated the relevance of IRAK1 phosphorylation and S100A8 expression in majority of tumour recurrence.

Figure 5:
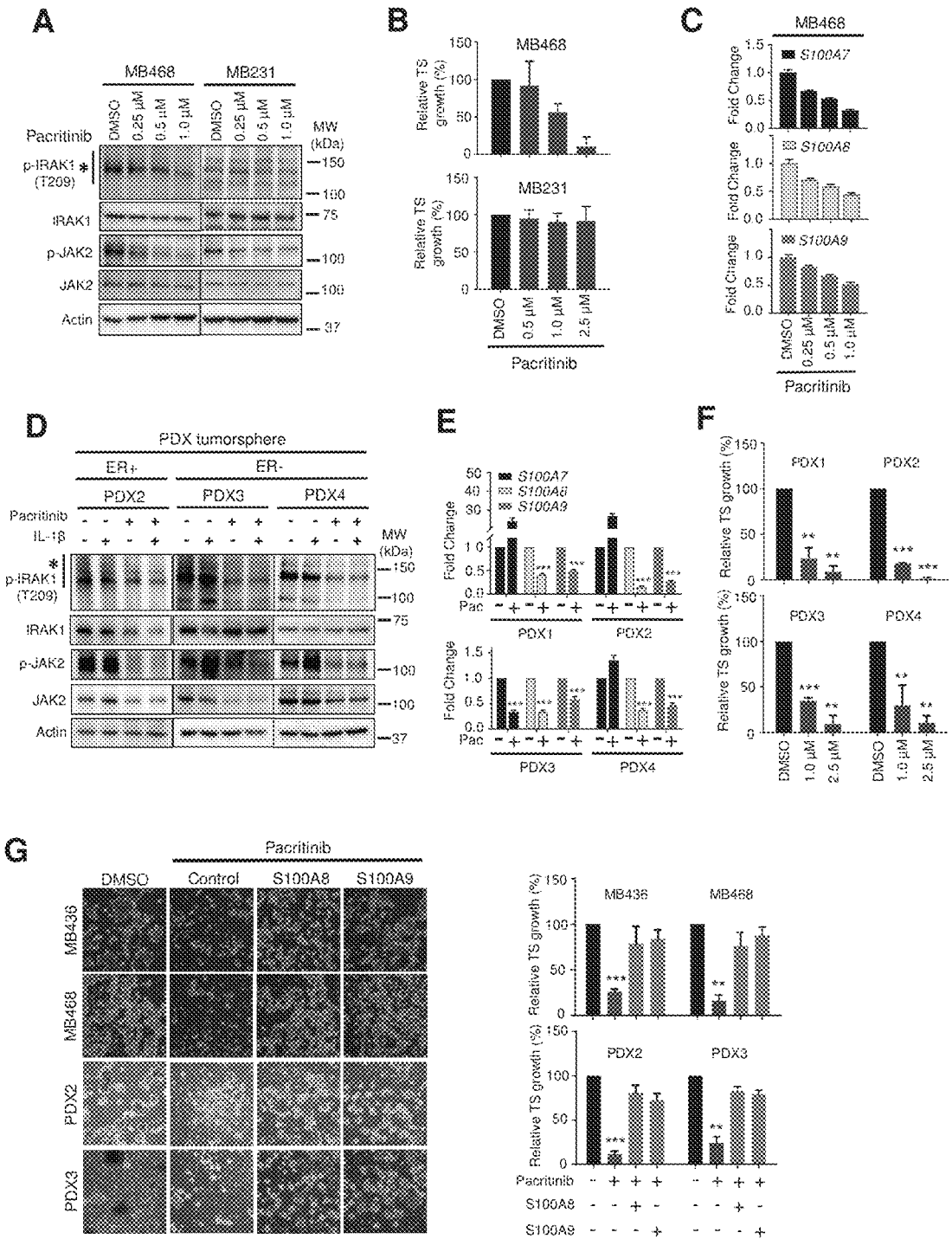
FIG. 5 shows that pacritinib effectively disrupts the IRAK-S100A7/8/9 feedback loop to inhibit tumoursphere growth. (A) Representative western blot showing inhibition of phospho-IRAK1 and phospho-JAK2 within 6 hr pacritinib treatment of MB468 and MB231 cells. Actin was used as loading control. (B) Quantification of the number of tumourspheres after pacritinib treatment in MB468 and MB231 tumourspheres. Data are expressed as means±s.e.m. of three independent experiments. (C) Real-time PCR analysis of S100A7/8/9 gene expression after 24 hr pacritinib treatment in MB468. (D) Representative western blot showing prolonged inhibition of phospho-IRAK1 after 24 hr pacritinib (2.5 μM) treatment of various PDX-derived tumourspheres with and without IL-1. Actin was used as loading control. (E) Real-time PCR analysis of S100A7/8/9 transcript levels after 24 hr pacritinib (2.5 μM) treatment. Data are expressed as means±s.d. of three technical replicates. (F) Quantification of the number of tumourspheres after pacritinib treatment in four different PDX-derived tumourspheres. Data are expressed as means±s.e.m. of three independent experiments. (G) Representative images and quantification of the number of tumourspheres in rescue assay. S100A8/9 recombinant protein (10 ng/ml) treatment is able to rescue pacritinib (2.5 μM) treated tumourspheres in various cell lines. Data are expressed as means±s.d. of three independent experiments. All p-values were calculated with two-tailed t-tests.  $p<0.01$, * $p<0.001$.

Example 7: Pacritinib Treatment Disrupts IRAK1-S100A7/8/9-Mediated Tumoursphere Growth Next, the IRAK1-S100A7/8/9 circuitry was explored as an actionable drug target in breast cancer. Pacritinib, a potent small molecule inhibitor of JAK2 is currently being evaluated in multiple phase II/III clinical trials for the treatment of myelofibrosis, has been recently reported to be a potent IRAK1 inhibitor. The ability of pacritinib to inhibit S100A-IRAK1 signaling in breast cancer cells was thus tested. Pacritinib was able to effectively block the phosphorylation of both IRAK1 and JAK2 as early as 6 hours in a dose-dependent manner in MB468 cells, though it also inhibited phosphorylation of JAK2 in MB231 cells (FIG. 5A). Remarkably, pacritinib treatment resulted in strong tumoursphere inhibitory effect in MB468 cell line but little effect in MB231 cell line (FIG. 5B), suggesting that JAK2 inhibition alone was insufficient to lead to growth inhibition in MB231 cells. Consistent with IRAK1 knockdown or mutant IRAK1 overexpression, pacritinib treatment also reduced the expression of S100A7/8/9 in MB468 cells in a dose-dependent manner (FIG. 5C). Pacritinib treatment can also induce a sustained inhibition of phospho-IRAK1 (FIG. 5D) and reduced expression of S100A7/8/9 (FIG. 5E) in patient-derived tumoursphere cells treated for 24 hours, which was concomitant with a strong tumoursphere growth inhibition (FIG. 5F). Interestingly, IL-1p treatment remarkably induced JAK2 phosphorylation but did not have an obvious effect on IRAK1 phosphorylation, suggesting the constitutive activation of phospho-IRAK1 in these patient-derived tumourspheres (FIG. 5D). Of note, although expressions of S100A8 and S100A9 were consistently reduced by pacritinib, the effect of pacritinib on S100A7 expression seemed to be cell specific, indicating a more consistent role of S100A8 and S100A9 in regulating tumoursphere growth. Crucially, the addition of the recombinant S100A8 or S100A9 protein to the culture medium effectively rescued pacritinib-induced growth inhibition in multiple cellular models of tumourspheres from both cell lines and patient-derived samples (FIG. 5G). These observations revealed a robust function of S100A8/9 in driving tumoursphere growth and demonstrated that inhibiting IRAK1-mediated S100A8 and S100A9 expressions contributed substantially to the effect of pacritinib.

Figure 14:
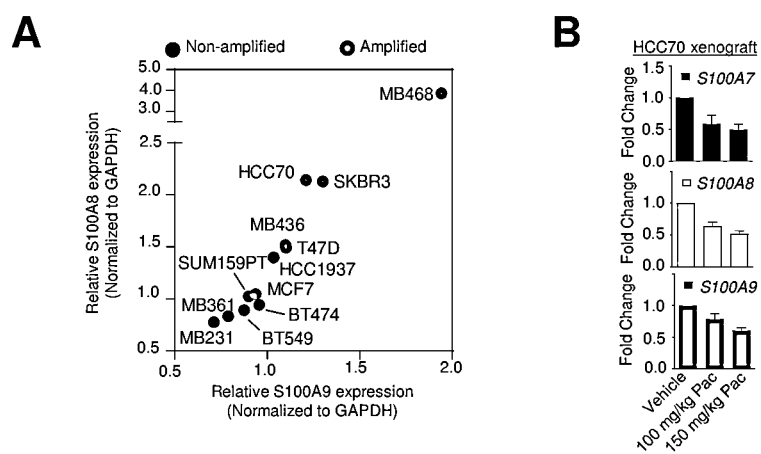
FIG. 14 (A) is a correlation analysis of S100A8 and S100A9 gene expression in 1q21.3 amplified and non-amplified breast cancer cell lines. Red: Amplified, Blue: Non-amplified.

Example 8: 1q21.3 Amplification is Associated with the Efficacy of Pacritinib Both In Vitro and In Vivo The presence of a correlation between 1q21.3 amplification and pacritinib sensitivity in breast cancer cells was investigated. For this purpose, the 1q21.3 gene amplification in a series of breast cancer cell lines was profiled using ddPCR (FIG. 6A). Of note, 1q21.3 status in these cell lines was in general correlated with phospho-IRAK1 and expression of S100A8/9 (FIG. 6B and FIG. 14A), but not with phospho-JAK2 status (FIG. 6B). Accordingly, pacritinib treatment was more effective in impairing tumoursphere growth in cancer cell lines positive for 1q21.3 amplification compared to negative cell lines (FIG. 6C). Of note, HCC1937, despite being negative for 1q21.3 amplification, expressed a high level of both phospho-IRAK1 and phospho-JAK2, and thus was sensitive to pacritinib treatment. These observations suggest that pacritnib response is more strongly associated with 1q21.3 amplification and IRAK1 compared to JAK2, and therefore 1q21.3 amplification could be a potential biomarker to stratify patients for an optimal drug response.

Next, the efficacy of pacritinib was tested in vivo using mice orthotopically engrafted with 1q21.3-amplified HCC70 that expresses a high level of phospho-IRAK1 but a low level of phospho-JAK2, as well as 1q21.3 non-amplified MB231 cell lines that express a low level of phospho-IRAK1 but a high level of phospho-JAK2 (See western blot in FIG. 6B). Pacritinib treatment in different doses resulted in substantial inhibition in tumour growth in HCC70 xenograft tumours but had no obvious effect on MB231 (FIG. 6D). The efficacy of pacritinib on HCC70 tumour growth was confirmed to be associated with downregulation of phospho-IRAK1 (FIG. 6E) and S100A7/8/9 expression (FIG. 14B), but not associated with JAK2.

To assess the potency of pacritinib in mitigating tumour recurrence in a mouse model, a clinically relevant "neoadjuvant" setting in which a breast cancer PDX mouse model was treated with paclitaxel to induce tumour regression before surgical removal of the remaining residual tumour as described above in relation to FIG. 10C was used. Mice were rested for 2 weeks to recover from surgery before further treatment with paclitaxel, pacritinib or combination of both. Although the tumour regrowth was slowed down by paclitaxel or pacritinib treatment and upon termination of the treatment the tumours showed faciliated growth, the combination of both eliminated the tumour regrowth for up to 2 months (FIG. 6F). Of note, the mice tolerated very well to pacritinib both alone and in combination with paclitaxel during the course of treatment, and there was no obvious toxicity and body weight loss (data not shown). These in vivo findings demonstrated the potential use of pacritinib in combination with standard chemotherapy regimen in the management of 1q21.3 amplified breast tumours.

Materials and Methods

Breast Tumour Dissociation and Patient-Derived Tumoursphere Culture Surgery resected tumour specimens were obtained from consenting patients.

Tumours were first washed with PBS supplemented Antibiotic-Antimycotic (Invitrogen, Cat. No. 15240-062) and then mechanically disaggregated followed by enzymatic digestion at 37° C. for 2 hr in DMEM/F12 solution with 1 mg/ml Collagenase Type IV (SIGMA, St. Louis, Mo.). After incubation, the cell suspensions were triturated and passed through a 40 µm pore strainer (BD Falcon, San Jose, Calif., USA), single cells were seeded onto ultra-low attachment plate (Corning, Kennebunk, Me.) at 50,000 cells/mL in serum-free DMEM/F12 supplemented with N2 and B27 (Gibco, Grand Island, N.Y.), 20 ng/ml epidermal growth factor (MACS, Auburn, Calif.), 20 ng/ml basic fibroblast growth factor (MACS, Auburn, Calif.), 0.2 µM Thiazovivin (STEMCELL Technologies, Vancouver, BC) and penicillin/streptomycin (Gibco, Carlsbad, Calif.). After 12-15 days, tumour spheres were passaged with 0.05% trypsin digestion followed by replating in the same manner as previous generation. All cells were maintained at 37° C. in a humidified atmosphere at 5% $CO_2$.

Cell Lines

All cell lines were obtained, authenticated, and cultured according to American Type Culture Collection (ATCC, Manassas, Va.) instructions. All cell lines used for functional studies were tested and found to be free of *mycoplasma* contamination. BT474, BT549, MB231, MB361, MB436, MB468, MCF7, SKBR3 and T47D breast cancer cell lines, HEK293T and Platinum-A (Plat-A) retroviral packaging cell lines were grown in Dulbecco's modified Eagle's medium (DMEM) (Invitrogen) supplemented with 10% fetal bovine serum (FBS). HCC70 and HCC1937 were maintained in RPMI (Invitrogen) medium supplemented with 10% FBS. SUM159PT cells were maintained in Ham's F-12 (Invitrogen) supplemented with 5% FBS, 5 µg/ml insulin (Invitrogen), and 1 µg/ml hydrocortisone (Invitrogen). All media were supplemented with 5000 U/ml penicillin/streptomycin (Invitrogen). All cell lines were maintained at 37° C. in a humidified atmosphere at 5% $CO_2$.

Reagents

Recombinant IL-1β (Cat no: 200-01B) was purchased from Peprotech (Rocky Hill, N.J.). Recombinant S100A7 (Cat no: pro-149), S100A8 (Cat no: pro-800) and S100A9 (Cat no: pro-814), were purchased from ProSpec (East Brunswick, N.J.). Cells were treated with recombinant proteins at stated concentration for 20 min before harvesting for western blot. Paclitaxel (Cat no: P-9600) was purchased from LC Lab (Woburn, Mass.). Pacritinib (Cat no: HY-16379) was purchased from MedChem Express (Princeton, N.J.).

Mammosphere Formation Assay PDX-derived tumoursphere cells were trypsinized and passed through 40 µm cell strainer to achieve single cell suspensions. $3 \times 10^4$ cells were seeded in 6-well ultra-low attachment plates (Corning, N.Y.; CLS3471) in serum-free DMEM/F12 supplemented with N2 and B27 (Gibco, Grand Island, N.Y.), 20 ng/ml epidermal growth factor (MACS, Auburn, Calif.), 20 ng/ml basic fibroblast growth factor (MACS, Auburn, Calif.), 0.2 µM Thiazovivin (STEMCELL Technologies, Vancouver, BC) and penicillin/streptomycin (Gibco, Carlsbad, Calif.). For breast cancer cell lines and MCF10A cell line, $3 \times 10^4$ cells were seeded in 6-well ultra-low attachment plates in Mammocult medium (Stem Cell Technologies, Vancouver, BC, Canada), supplemented with fresh hydrocortisone (0.5 μg/ml) and heparin (1:500). Mammospheres were maintained at 37° C. with 5% $CO_2$ and topped up with medium every 3 days. After 7-9 days, mammospheres were stained with INT (2-(4-iodophenyl)-3-(4-nitrophenyl)-5-phenyl-2H-tetrazolium chloride, Sigma-Aldrich) and quantified. Imaging and quantification were done using GelCount apparatus and associated software (Oxford Optronix, Abingdon, UK). For pacritinib treatment, cells were seeded in mammosphere medium and treated at indicated concentrations, and supplemented with fresh drug at respective dosage every 3 days until quantification. For S100A8 and S100A9 recombinant protein rescue experiments, tumourspheres were pretreated 10 ng/ml of respective S100A8 or S100A9 recombinant protein for 1 hr before treatment with 1 μM pacritinib. Every 3 days, 0.5 ml of fresh growth medium, pacritinib and respective recombinant protein were supplemented to the corresponding initial tumoursphere treatment condition.

Cell Proliferation Assay

For cell proliferation assay, the optimal cell seeding was first determined empirically for all cell lines by examining the growth of a wide range of seeding densities in a 96-well format to identify conditions that permitted proliferation for 7 days. Cells were then plated at the optimal seeding density in triplicate. Plates were incubated for 7 days at 37° C. in 5% $CO_2$. Cells were then lysed with CellTiter-Glo (CTG) (Promega, Madison, Wis.) and chemiluminescent signal was detected with a microplate reader on Day 0, 1, 3, 5, and 7. Luminescence signal values obtained during the 7 days were plotted against time.

shRNAs and Ectopic Overexpression

Inducible IRAK1 shRNA as well as ectopic IRAK1 wild-type and K239S kinase dead mutant were generated as described previously (see for e.g. Wee, Z. N., et al. IRAK1 is a therapeutic target that drives breast cancer metastasis and resistance to paclitaxel. *Nature communications* 6, 8746 (2015)). To generate S100A7, S100A8 and S100A9 knockdown cell lines, shRNA oligos were subcloned into pLV-H1-EF1a-RFP-Puro (Cat. No: SORT-B31) vector according to manufacturer's instruction (Biosettia, San Diego, Calif.). The shRNA sequence was confirmed with DNA sequencing of plasmid. Stable knockdown cell lines were generated via lentiviral infection using HEK293T to package lentivirus. Briefly, 2 μg of pLV shRNA plasmid together with 1.5 μg of psPAX2 μlasmid (Addgene) and 0.5 μg of pMD2.G plasmid (Addgene) were transfected into HEK293T cells using Lipofectamine 2000 (Invitrogen). Media containing transfection reagent was removed 8 hours post transfection and replaced with 5% FBS containing DMEM medium. Lentivirus containing media were collected 24 hr later and passed through 0.45 μm filter to remove detached HEK293T cells. Adherent monolayer cells were infected with lentivirus harbouring shRNA plasmids at Multiplicity of Infection (MOI) of 3 for 24 hr in the presence of 8 μg/ml of polybrene and then maintained with puromycin (MB436: 1.5 μg/ml, MB468: 0.5 μg/ml). Cells selected for 7 days were immediately seeded for tumoursphere assay and cell proliferation assay concurrently.

For PDX-derived tumoursphere cell lines, lentivirus containing media was first concentrated with Amicon® (Millipore, Ireland) ultra-centrifugal filter columns (Cat. No: UFC910096) before infecting tumoursphere cells at MOI of 3 for 24 hr in the presence of 8 μg/ml of polybrene. Positive cells were selected with puromycin (1 μg/ml) before performing downstream assays.

The specific shRNA oligos used for cloning are summarized in the following table.

TABLE 9

| GENE | ACCESSION NO. | OLIGO SEQUENCE | TARGET |
|---|---|---|---|
| S100A7 | NM_002963.3 | AAAAGCCGATGTCTTTGAGAAAATTG GATCCAATTTTCTCAAAGACATCGGC (SEQ ID NO: 17) | ORF |
| S100A8 | NM_002964.4 | AAAAGGGATGACCTGAAGAAATTTT GGATCCAAAATTTCTTCAGGTCATCC C (SEQ ID NO: 18) | ORF |
| S100A9 | NM_002965.3 | AAAAGCAACATAGAGACCATCATTTG GATCCAAATGATGGTCTCTATGTTGC (SEQ ID NO: 19) | ORF |

RNA-Seq 12 primary human breast tumours and corresponding tumoursphere cells were used to generate RNA-seq data. RNA-seq libraries were generated by using the cDNA amplification kit SMARTer® Ultra™ Low RNA Kit (Cat. No. 634935, Clontech Laboratories, Inc. Mountain View, USA) for small amount of RNA or less than 200 cells according to manufacturer's manual followed by DNA library construction using the NEBNext® DNA Library Prep Master Mix Set for Illumina® kit (Cat. No. E6040S, New England Biolabs, Ipswich, Mass.). In brief, c.a. 50 ng of total RNA or 200 tumour cells were first lysed in reverse transcription buffer and the reaction was initiated with oligodT containing primer. Complete first strand synthesis was followed by template switching and the incorporation of SMARTer oligonucleotide. Full-length cDNAs are amplified using PCR to obtain DNA. Fragmentation and adapter introduction was performed using acoustic shearing to approximately 200 to 500 bp length and NEBNext® DNA Library Prep kit incorporating multiplex index primers. A pooled multiplexed library consisting equal amount of 6 individual libraries were sequenced on The HiSeq 2500 System by the GIS core facility.

For data processing and analysis, Illumina 100 bp paired-end sequenced reads were aligned to reference human genome 19 using Bowtie2 and TopHat2. All further analysis were performed using R Statistical Programming. summarizeOverlap command from Genomic Alignments package was used to count reads with the default mode of "Union". AnnotationDbi package was used to annotate the genes. Genes were ranked according to significance of differential expression between primary tumours and its derived tumourspheres using DESeq. The differentially expressed gene list was narrowed down by using statistical analysis values such as false discovery rate and fold change. Genes showing>2-fold alteration in expression, false discovery rate (FDR)<0.05 cutoff were considered as significantly altered expression. Heatmap of upregulated genes was generated using gplots package.

Expression Microarray Analysis

To identify the S100 family members important in breast cancer stem cells, two sets of expression microarray analysis were performed. The first microarray set consisted of RNA extracted from four PDX tumours and the corresponding ex vivo tumoursphere cultures. The second microarray set consisted of four 1q21.3 amplified cell lines (MB436, MB468, MCF7 and T47D) and four 1q21.3 copy number non-amplified cell lines (BT549, BT474, MB361, MB231). RNA extracted from cells were used for expression microarray analysis using the Illumina Gene Expression Sentrix BeadChip HumanHT-12_V4 (Illumina, San Diego, Calif.)

according to the manufacturer's recommended protocol. In brief, 500 ng total RNA was converted to single-stranded cDNA using a T7 Oligo(dT) primer, and subsequently converted to double-stranded DNA (dsDNA) template for transcription. The dsDNA was then amplified and labeled with biotin to generate biotinylated cRNA. The labeled cRNAs were hybridized to Illumina BeadChip HumanHT-12_V4 microarray slides for 20 hr. After extensive washing, the Cy3-SA was introduced to bind to the analytical probes that had been hybridized to the BeadChip. The microarrays were then scanned with Illumina BeadArray Reader. The Illumina BeadArray Reader used a laser to excite the fluor of the hybridized single-stranded product on the beads of the BeadChip sections. Light emissions from these fluors were then recorded in high-resolution images of the BeadChip sections. Data from these images were analyzed using Illumina's GenomeStudio Gene Expression Module. The raw intensity data for gene expression profile were further analyzed using GeneSpring GX software (Agilent Technologies, Santa Clara, Calif.). The differentially expressed S100 genes (fold change 2) were identified by comparison between tumourspheres vs PDX tumour, amplified vs non-amplified breast cancer cell lines.

TCGA Analysis

Copy number variation of upregulated genes were analyzed using web-based cBioPortal (http://www.cbioportal.org/) using TCGA Breast Invasive Carcinoma (TCGA, Cell 2015) dataset (see Ciriello, G., et al. Comprehensive Molecular Portraits of Invasive Lobular Breast Cancer. *Cell* 163, 506-519 (2015)). Briefly, gene sets of interest were submitted through cBioPortal and putative copy number alternations data from Genomic Identification of Significant Targets in Cancer (GISTIC) (see Mermel, C. H., et al. GISTIC2.0 facilitates sensitive and confident localization of the targets of focal somatic copy-number alteration in human cancers. *Genome biology* 12, R41 (2011)) for each gene were retrieved and presented in a graphical OncoPrints, showing putative homozygous (deep) genetic deletions and genetic amplification (gain in two or more copy numbers).

To study copy number variation in relation to its gene expression, the normalized gene expression TCGA dataset for Breast Invasive Carcinoma (TCGA, Cell 2015) along with its copy number data (with GISTIC annotations) were downloaded from the UCSC Cancer Genomics Browser. Patients were stratified according to their copy number status (Deletion: −1, Neutral: 0, Gain: +1, Amp: +2). The mean mRNA expression of the 17 genes identified on 1q21.3 was calculated for each individual patient and plotted against its copy number status. p-values were calculated with Kruskal-Wallis test.

To correlate the copy number variation with clinical prognosis, the clinical information (Time to death from initial diagnosis) and copy number data (with GISTIC annotations) of TCGA Breast Invasive Carcinoma dataset (TCGA, Cell 2015) were downloaded from the UCSC Cancer Genomics Browser. Copy number status of 1q21.3 and 8q were analyzed. Patients were grouped into two groups (Neutral vs Gain+Amp) and their Time to Death clinical feature was analyzed. p-values were calculated with Mann Whitney test.

Breast Cancer Survival Analysis of Public Dataset

Kaplan-Meier (KM) survival analysis for relapse-free survival (RFS) were performed using the online database (www.kmplot.com). The following 17 probes were used to generate the KM plots: TUFT1 (205807_s_at), S100A10 (200872_at), S100A11 (200660_at), SPRR1A (213796_at), SPRR1B (205064_at), S100A9 (203535_at), S100A8 (202917_s_at), S100A7 (205916_at), S100A6 (217728_at), S100A2 (204268_at), S100A16 (227998_at), S100A14 (218677_at), SNAPIN (223066_at), JTB (200048_s_at), RAB13 (202252_at), UBE2Q1 (222480_at), EFNA (210132_at). Mean expression of the 17 probes was used to generate survival curves. ER status of patient was derived from gene expression dataset. The percentiles of the patients between the upper and lower quartiles were auto-selected based on the computed best performing thresholds as cut-offs. All other parameters were left at default settings unless otherwise stated.

Kaplan-Meier Survival Analysis of Breast Cancer Patient Cohorts

To generate Kaplan-Meier plots for Singapore TTSH discovery cohort tumour samples, a cutoff of 1.5 copy number ratio for S100A8 gene was used to yield two groups. To generate Kaplan-Meier plots for Denmark OUH early-staged and Singapore NUHS advanced-staged cohort blood samples, a cutoff of 1.147 (3×SD above mean) copy number ratio for 3-gene (TUFT1, S100A8 and S100A7) was used to yield two groups for progression-free and overall survival analysis. For the Singapore NUHS advanced-stage cohort, baseline and post-chemo 1q21.3 amplification status was also evaluated to yield four different groups for overall survival analysis. KM plots were generated for the respective groups using GraphPad Prism version 6.0.

Genomic DNA Extraction and Analysis

Fresh frozen tumour samples were homogenized with QIAGEN TissueLyzer II and genomic DNA was extracted with a QIAamp DNA Mini kit (QIAGEN, Hilden, Germany), as described by the manufacturer. DNA was isolated from formalin fixed, paraffin-embedded (FFPE) samples after extraction of 5 µm thick paraffin sections in xylene and by using the QIAamp DNA FFPE Tissue kit (QIAGEN, Hilden, Germany) DNA extraction protocol as described by the manufacturer. FFPE slides were stained with hematoxylin eosin to evaluate tumour cell content.

Quantitative PCR assays were performed using KAPA SyBr Fast qPCR kit (KAPA Biosystems, Wilmington, Mass.). 10 ng of genomic DNA was used for each reaction. For relative fold change of genomic DNA, RPP30 level was used as an internal control for normalization. All reactions were analyzed in an Applied Biosystems PRISM 7500 Fast Real-Time PCR system in 96-well plate format.

ALDEFLUOR Assay and Fluorescence-Activated Cell Sorting (FACS) ALDEFLUOR assay was performed using the manufacturer's recommended protocol (ALDEFLUOR kit, Stemcell Technologies; catalogue number: #01700). In brief, one million single-cell suspensions were centrifuged and resuspended in ALDEFLUOR assay buffer supplied in the kit. Each sample cells were incubated with or without an ALDH-specific inhibitor 15 mM diethylaminobenzaldehyde (DEAB) in the presence of 0.15 mM ALDH substrate. For FACS analysis only, ALDEFLUOR staining was detected using fluorescein isothiocyanate (FITC) channel of a FACSCalibur Flow Cytometry System (BD Biosciences) after 30 min incubation at 37° C. DEAB inhibitor control sample was used as sorting gate reflecting background fluorescence levels for each cell lines. For cell sorting, ALDH-positive and -negative cell populations were sorted after ALDEFLUOR staining using BD FACSAria II, BD FACSAria Fusion or Beckman MoFlo. Sorted cells were pelleted and extracted for genomic DNA using QIAamp DNA Mini Kit (QIAGEN, Hilden, Germany).

DNA Fluorescence In Situ Hybridization (FISH).

All FISH assays were carried out in accordance to the manufacturers' specifications. In brief, cells were trypsinized and harvested for DNA FISH. Cell pellet was washed once with phosphate buffered saline (PBS) and treated with 75 mM KCl for 15 min before fixing with modified Carnoy's fixative. For preparation of the glass microscope slide, a circle with a 12 mm diameter was etched on the underside of the slide and a drop of the fixed cell suspension was placed over it and allowed to air-dry. The slide was dehydrated through an ethanol series (70%, 85% and 100%) for about 2 min each at room temperature and allowed to dry.

FISH assays were carried out using a DNA probe mixture consisting of a 1q21.3 probe labelled in Texas Red® and a 1p32.3 probe labelled in FITC (Cytocell Aquarius, Cambridge, United Kingdom, Catalog No. LPH 039-A). The DNA probe mixture was applied to the target area and co-denatured, followed by overnight hybridization at 37° C. Washes were performed and the slide was counterstained with DAPI anti-fade solution (Vectashield, Vector Laboratories, CA) and analyzed under an epi-fluorescence microscope. Signals from 100 non-overlapping nuclei were enumerated for copy number changes and a normal signal pattern is defined as two copies.

Animal Work

Surgical procedures and experiments were conducted in compliance with animal protocols approved by the A*STAR-Biopolis Institutional Animal Care and Use Committee of Singapore (IACUC). 6-8 wk old female NOD/MrkBomTac-Prkdcscid mice were purchased from InVivos (Singapore). For PDX orthotopic xenotransplantation, tissue suspension was first prepared from whole tumour explant from mammary fat pad of immunodeficient mice. Whole tumours were washed in PBS, minced with sterile scalpel and triturated until cells could pass through needle bore. The PDX cell suspension was resuspended in reduced Matrigel (BD Bioscience, Cat No: 356230), and then 10 µl was injected into the mammary fat pad. Autoclips was used for primary wound closure. Mice were observed post-procedure for 1-2 hr, and their body weights and wound healing were monitored weekly. Tumours were measured by vernier caliper twice weekly and the tumour volume was calculated with the following formula: $V=W \times W \times L/2$.

For in vivo pacritinib sensitivity test, one million MB231 or HCC70 cells mixed 1:1 in PBS:Matrigel were injected into the mammary fat pad of mice using standard procedures. After the tumours reached 100 $mm^3$, the mice were randomized into four groups: Treatment with vehicle, 50 mg/kg pacritinib, 100 mg/kg pacritinib and 150 mg/kg pacritinib. Mice were then dosed daily by oral gavage for 21 days. Tumour growth was monitored for 1 month.

For in vivo PDX model, each mouse bore one PDX tumour on one side of the mammary fat pad. After the tumours reach 100 $mm^3$, the mice were randomized into two groups: Vehicle treated control tumour (n=4) and paclitaxel treated tumour (n=27). Treated mice were given 20 mg/kg of paclitaxel (P-9600, LC Lab) every other day for two consecutive weeks to induce tumour regression. Upon completion of paclitaxel treatment, the tumours were surgically removed. The mice were given one week to recover before randomization into four groups: Vehicle alone (n=4), paclitaxel (20 mg/kg) treatment alone (n=4), pacritinib (150 mg/kg) treatment alone (n=4), paclitaxel+pacritinib combination treatment (n=4). Following the drug treatments, the tumours were monitored for approximately one month. Tumours were excised when it reached 1000 $mm^3$ or at the end of study. Genomic DNA was extracted from the untreated (n=4), residual tumours following paclitaxel treatment (n=5) and recurrent tumours following paclitaxel treatment (n=4) for ddPCR analysis. Mice were euthanized as per ethical guidelines, and the harvested tumours were flash-frozen in liquid nitrogen.

Isolation and Quantification of Circulating cfDNA

For blood serum collection, approximately 3 mL of whole blood was allowed to clot after collection in a cover tube by leaving undisturbed at room temperature for 30 min. Then the clot was removed by centrifugation at 1,500×g at 4° C. for 10 min. The resulting supernatant portion of blood serum was further aliquoted and stored at −80° C. For blood plasma collection, approximately 3 mL of whole blood was collected in EDTA containing tube according to hospital standard procedure. Then the blood was centrifuged at 1,500×g at 4° C. for 7 min. The upper layer of clear plasma was further aliquoted and stored at −80° C. On the day of cfDNA isolation, c.a. 500 µl of frozen plasma or serum was quickly thawed in a warm water bath immediately followed by a further centrifugation at 20,000×g for 10 min at 4° C. cfDNA was isolated using the QIAamp circulating nucleic acid kit (QIAGEN, Hilden, Germany, cat. no. 55114) from the cleared supernatant according to manufacturer's instructions. Purified cfDNA was quantified using Quant-iT PicoGreen dsDNA Assay Kit (Thermo Fisher Scientific, Carlsbad, Calif., cat. no. P7589) and DNA fragment size distribution was further visualized using a High Sensitivity DNA Analysis Chip running on a 2100 Bioanalyzer Instrument (Agilent Technologies, Waldbronn, Germany, Cat. no. 5067-4626).

Droplet Digital PCR

Digital PCR was performed on a QX200 ddPCR system (Bio-Rad) using EvaGreen chemistry with primers at a final concentration of 100 nM primers. PCR reactions were prepared with ddPCR Supermix for EvaGreen (Bio-Rad) and partitioned into a median of 20,000 droplets per sample in a QX-200 droplet generator according to the manufacturer's instructions. For genomic DNA analysis, 5 ng of genomic DNA was used for each reaction. For cfDNA, 2 ng of cfDNA extracted from 300-500 µl of plasma or serum was analyzed. At least two negative control wells with no DNA template were included in every batch. Emulsified PCR reactions were run on a 96-well plate thermal cycler (C1000 Touch, Bio-Rad), incubating the plates at 95° C. for 5 min, followed by 40 cycles of 95° C. for 30 sec and 60° C. extension temperature for 90 sec, then followed by a 5 min incubation at 4° C. and another 5 min at 98° C. The temperature ramp increment was 2° C./sec for all steps. Plates were read on a Bio-Rad QX200 droplet reader using QuantaSoft version 1.4.0.99 software from Bio-Rad to assess the number of droplets positive for DNA. Analysis of the ddPCR data was also performed with the QuantaSoft software (Bio-Rad).

The specific primers used for ddPCR and qPCR are summarized in the following table:

TABLE 10

| GENE | FORWARD PRIMER | REVERSE PRIMER | AMPLI-CON LENGTH |
| --- | --- | --- | --- |
| LAMB3 | CAGCGCTGAATAAACGGCAA (SEQ ID NO: 13) | TCAGGGCTCTTCACCAAACC (SEQ ID NO: 14) | 85bp |
| PVRL4 | GGGGAACTTCCATACCAGCA (SEQ ID NO: 15) | CACTCCCTGGCTAAGGAACC (SEQ ID NO: 16) | 83bp |

TABLE 10-continued

| GENE | FORWARD PRIMER | REVERSE PRIMER | AMPLI-CON LENGTH |
|---|---|---|---|
| RPP30 | GTTAGAGAGTCTCCAG GCCC (SEQ ID NO: 10) | ACTGTAATCCAGCAAAAGCGG (SEQ ID NO: 11) | 70bp |
| S100A7 | TTTTAATCAGAGGGTG AGGGTGAT (SEQ ID NO: 1) | GCTTCTCAATGTTGGAGGA TACA (SEQ ID NO: 2) | 70bp |
| S100A8 | GTCAAGATTGAGGAGG AAGAAGC (SEQ ID NO: 3) | TTCATAGATGGCTATGCCT CGG (SEQ ID NO: 4) | 70bp |
| TUFT1 | GGTGTTTCCCCACTA GCCA (SEQ ID NO: 5) | CCCAGAGAGTGTATTGGCCC (SEQ ID NO: 6) | 79bp |

Droplet Digital PCR with Probes

Digital PCR with probes is carried out in accordance to the manufacturer's instructions (Bio-Rad ddPCR™ Supermix for Probes instruction manual (10026235 Rev C)). TaqMan probes were designed for each of the four genes S100A7, S100A8, TUFT1 and RPP30 for use with their primer pairs in a ddPCR assay. The probe for the reference gene RPP30 was labelled with the fluorophore HEX while the probes for the three other target genes S100A7, S100A8, TUFT1 were labelled with the fluorophore FAM.

The specific probes for each of the four genes are summarized in the following table:

TABLE 11

| GENE | PROBE SEQUENCE | FLUORO-PHORE |
|---|---|---|
| S100A7 | TGCTATGTGGCCTTGGACAGATCACC (SEQ ID NO: 7) | FAM |
| S100A8 | AGTTTAAAGATCTCAGAGAGAGCCGAGGCA (SEQ ID NO: 8) | FAM |
| TUFT1 | CCTTAGCGTATCACATGTGGACATGGACA (SEQ ID NO: 9) | FAM |
| RPP30 | TGTCCACAGACTTTCTCAAAAGATAGGGCC (SEQ ID NO: 12) | HEX |

Immunoblotting

All immunoblots shown in this specification represent at least two independent experiments. In brief, cells were washed with PBS and lysed in RIPA buffer supplemented with protease and phosphatase inhibitors and further sonicated using an XL2000 Microson Ultrasonice Processor (Misonix). Equal amounts of protein extract were separated on SDS-polyacrylamided gels and transferred to PVDF membranes. Membranes were further blocked with 5% milk or BSA, and then probed with the following antibodies: anti-IRAK1 was purchased from Santa Cruz Biotechnology (Santa Cruz, Calif.; sc-7883), anti-phospho-IRAK1 (T209) was purchased from Assay Biotech (Sunnyvale, Calif.; A1074), anti-JAK2 (Danvers, Mass.; #3230) and anti-phospho-JAK2 (Y221) (Danvers, Mass.: #3774) were purchased from Cell Signaling Technology, anti-actin was purchased from Sigma Aldrich CA; A5441). For protein extraction of xenograft tumours, snap frozen samples were resuspended in RIPA buffer supplemented with protease and phosphatase inhibitors and homogenized with QIAGEN TissueLyzer II as described by the manufacturer, followed by immunoblotting as described above.

Quantitative RT-PCR Analysis

Total RNA was isolated using TRIzol® reagent (Life Technologies, Carlsbad, Calif.; 15596026) and purified with Direct-zol™ RNA MiniPrep (Zymo Research, Irvine, Calif.; R2050). Reverse transcription and quantitative PCR assays were performed using High-Capacity cDNA Reverse Transcription Kit (Applied Biosystems, Carlsbad, Calif.; 4368813) and KAPA SyBr Fast qPCR kit (KAPA Biosystems, Wilmington, Mass.; KK4601). For quantification of mRNA levels, GAPDH level was used as an internal control. All reactions were analysed in an Applied Biosystems PRISM 7500 Fast Real-Time PCR system in 96-well plate format. For RNA extraction of xenograft tumours, snap frozen samples were resuspended in TRIzol® reagent and homogenized with QIAGEN TissueLyzer II as described by the manufacturer, followed by purification with Direct-zol™ RNA MiniPrep.

IHC Staining for Clinical Samples

Paraffin-embedded sections of primary and recurrent tumours were obtained from Tan Tock Seng Hospital, Singapore. Staining and image analysis of clinical samples were performed by Histopathology Department of Institute of Molecular and Cell Biology, Agency for Science, Technology, and Research (A*STAR), Singapore. Briefly, paraffin-embedded tissue sections were deparaffinized, rehydrated and antigens were retrieved by proteinase K solution; sections were then incubated in 3% $H_2O_2$ at room temperature, to block endogenous peroxidase. Slides were incubated in phospho-IRAK1 (S376) antibody from Genetex (Cat No: GTX60149, 1:500 dilution) or S100A8 (also known as MRP8) antibody from Abcam (Cat No: ab92331, 1:500 dilution) overnight, followed by 30 min incubation with anti-mouse Labelled Polymer (Dako, Calif.). Specificity of the immunostaining was determined by the inclusion of isotype specific IgG as a negative control. The detection system was DAB+ Substrate-Chromagen Solution (Dako, Calif.). The sections were counterstained with haematoxylin. Slides were scanned at 20× using a Leica SCN400 slide scanner (Leica Microsystems, Germany). Images were exported to Slidepath Digital Image Hub (Leica Microsystems) for viewing. The total cellular H-score were then further normalized and expressed as Z-score after conversion with the following formula, z=(total cellular H-score of each tumour—mean H-score)/std. dev. of all tumours. Scanning and image analysis was performed by the Advanced Molecular Pathology Laboratory, IMCB, Singapore.

Statistical Analysis

All statistical analyses were performed with GraphPad Prism version 6.0 or IBM SPSS Statistics version 20. Non-parametric tests, Kruskal Wallis and Mann-Whitney were used to investigate the effect of copy number variation (CNV) on mRNA expression of genes and Time to Death respectively in GraphPad Prism. The McNemar test was used to test the change in the number of patients who have 1q21.3 amplification in matching primary tumour and recurrent tumour using GraphPad Prism. The Chi-Square independence test used to find the relation of CNV in primary tumour and relapse was done with SPSS. Correlation analyses were done using Spearman's correlation coefficients in GraphPad Prism. Receiver operator character curve was generated and Area under curve was calculated using MedCalc statistical software. All p-values were two-sided and significance was accepted at p-value<0.05 unless otherwise stated.

Study Approval

Human tissue samples were provided by Tan Tock Seng Hospital and National University Cancer Institute, Singapore, National Cancer Center of Singapore, John Wayne Cancer Institute (USA) and Odense University Hospital (Denmark). Studies with these samples were approved by institutional review boards of each institution, respectively. Informed written consent was obtained from each individual who agreed to provide tissue and/or blood samples for research purposes.

Applications

The inventors have identified human chromosome chr1q21 amplification, particularly 1q21.3 amplification and associated S1007/8/9-IRAK1 signaling feedback loop as an important driver event in breast cancer progression. The inventors have further demonstrated the enrichment of 1q21.3 amplification in breast cancer TICs and in up to 70% of recurrent breast cancer tumours, which detection in the blood using cfDNA could serve as a potential circulating biomarker to predict disease outcomes and monitor treatment response. Importantly, the inventors have also established 1q21.3-directed molecular event as an actionable target which has significant implications for the clinical management of breast cancer patients.

The high occurrence rate of 1q21.3 amplification in recurrent tumours of both ER-positive and ER-negative breast cancer patients indicates that embodiments of the method based on determining human chromosome chr1q21 amplification, particularly 1q21.3 amplification might be useful to cover the majority of breast cancer patients across different subtypes. The inventors have shown that in both early-stage and advanced-stage patients, embodiments of the method are able to identify patients who are at high risk of early relapse. Embodiments of the method may also be used to evaluate tumour response and monitor the onset of chemoresistance earlier than radiological imaging during the course of treatment, as demonstrated in the examples describing serial sample analysis during the course of chemotherapy. It is envisaged that embodiments of the method could be used to supplement clinical decision-making and reduce repetitive imaging follow-up of patients.

Due to a high degree of inter-tumour heterogeneity and thus the lack of hotspot mutation common in the different breast cancer subtypes, current mutation tracking approach requires NGS for the identification of tumour-associated mutations for personalized assay development. In addition, current NGS-based cfDNA assay in development focusing on mutation tracking lacks prognostic value at the time of diagnosis, though such assays could predict outcomes of patients based on the amount of ctDNA detected after surgery.

Embodiments of the method based on cfDNA detection of human chromosome chr1q21 amplification, particularly 1q21.3 amplification could be easily adopted for clinical use, and in contrast to current blood-based assays which have poor capacity in monitoring breast tumour progression, embodiments of the method are able to yield more accurate and sensitive outcome predictions, as demonstrated by the examples.

The inventors further demonstrated the functional relevance of human chromosome chr1q21 amplification, particularly 1q21.3 amplification to IRAK1 activation and unraveled a functional circuitry involving S100A7/8/9 and IRAK1 in empowering tumoursphere growth (See model in FIG. 6G). S100A8, secreted by myeloid cells found in the tumour microenvironment, has been previously shown to promote breast cancer chemoresistance and metastasis. However, the inventors have demonstrated a cancer cell-autonomous role of S100A family members, resulting from human chromosome chr1q21 amplification, particularly 1q21.3 amplification, in disease progression. The inventors have further found out that IRAK1 activity is important in triple negative breast cancer metastasis and chemoresistance.

In the present specification, the inventors have shown elevated IRAK1 phosphorylation and S100A8 in up to 70-80% of both ER-positive and ER-negative recurrent breast cancer tumours, which is consistent with the high proportion of recurrent breast cancer tumours showing human chromosome chr1q21 amplification, particularly 1q21.3 amplification. Importantly, the inventors have further demonstrated that human chromosome chr1q21 amplification, particularly 1q21.3 amplification and associated IRAK1 activation could be targeted by an existing small molecule agent, pacritinib, as demonstrated in both in vitro and in vivo models. Intriguingly, pacritinib-induced growth inhibition can be effectively rescued by recombinant S1008/9 indicating a crucial role of S100A8/9 in mediating the effects of pacritinib. Moreover, the inventors have shown that breast cancer cells which harbored human chromosome chr1q21 amplification, particularly 1q21.3 amplification are more sensitive to pacritinib treatment compared to cancer cells without 1q21.3 amplification, suggesting the potential value of 1q21.3 amplification as a biomarker to guide patient selection for a better response to pacritinib. Pacritinib can be re-purposed in breast cancer treatment to address the unmet clinical need of disease recurrence. Importantly, 1q21.3 amplification is also found in other cancers whereby it shows consistent exclusivity with other druggable driver mutations (FIG. 6H).

Therefore, embodiments of the method based on targeting 1q21.3 amplified tumours with therapeutic agents such as pacritinib may provide benefits for those patients without druggable mutations and encourage a "basket" trial of therapeutic agents such as pacritinib in patients whose tumours carry 1q21.3 amplification.

The widespread 1q21.3 amplification and S100A7/8/9-IRAK1 functional loop present in recurrent tumours across distinct breast cancer subtypes highlighted the broad applicability of embodiments of the method.

The invention claimed is:

1. A method of treating breast cancer in a subject, the method comprising:
   determining that a copy number amplification of a region specific to human chromosome 1q21.3 is present in a tumour tissue and/or blood sample from the subject,
   wherein determining that a copy number amplification of a region specific to human chromosome 1q21.3 is present in a tumour tissue and/or blood sample from the subject comprises evaluating a copy number ratio of at least one continuous genomic region located on human chromosome 1q21.3 in the subject to a reference continuous genomic region in the subject, wherein if the copy number ratio exceeds a threshold value it is indicative of copy number amplification, and
   wherein the at least one continuous genomic region selected from the group consisting of: a human TUFT1 gene, a gene from the human S100 family, and combinations thereof,
   administering to the subject pacritinib or therapeutically effective analogs thereof,
   wherein the pacritinib or therapeutically effective analogs thereof leads to a reduction in the expression of a human S100 family gene driving breast cancer progression in the subject,
   wherein the human S100 family gene is selected from S100A7, S100A8, S100A9 and combinations thereof.

2. The method of claim 1, wherein the subject was previously ineffectively treated for breast cancer by an earlier therapy, wherein the earlier therapy does not comprise administration of pacritinib or therapeutically effective analogs thereof.

3. The method of claim 1, wherein the blood sample comprises cell-free DNA.

4. The method of claim 1, wherein the threshold value is obtained by establishing the copy number ratio of the at least one continuous genomic region in a healthy subject to the reference continuous genomic region in the healthy subject.

5. The method of claim 1, wherein said evaluating the copy number ratio of the at least one continuous genomic region comprises evaluating an average copy number ratio of at least two continuous genomic regions located on human chromosome 1q21.3 and wherein said average copy number comprises:
   obtaining the copy number ratio of each of the at least two continuous genomic regions; and
   averaging the copy number ratios of the at least two continuous genomic regions to obtain the average copy number ratio.

6. The method of claim 1, wherein the threshold value is obtained by evaluating a mean copy number ratio of the at least one continuous genomic region located on human chromosome 1q21.3 based on two or more healthy reference subjects and wherein said evaluating the mean copy number ratio based on two or more healthy reference subjects comprises:
   evaluating the copy number ratio of the at least one continuous genomic region of a first healthy reference subject;
   evaluating the copy number ratio of the at least one continuous genomic region of a second healthy reference subject; and
   adding the copy number ratios of the two or more healthy reference subjects; and
   dividing by the number of healthy reference subjects.

7. The method of claim 1, wherein said evaluating the copy number ratio of the at least one continuous genomic region comprises evaluating a copy number ratio of the at least one continuous genomic region of one or more subsequent healthy reference subjects to obtain one or more subsequent copy number ratios.

8. The method of claim 1, wherein said determining whether a copy number amplification of a region specific to human chromosome 1q21.3 is present in the tumour tissue/blood sample from the subject comprises contacting the tumour tissue/blood sample with one or more oligonucleotides for hybridizing to the region specific to human chromosome 1q21.3.

9. The method of claim 8, wherein the one or more oligonucleotides comprises a primer for amplifying the at least one continuous genomic region located on human chromosome 1q21.3.

10. The method of claim 8, wherein the one or more oligonucleotides comprise a sequence selected from the group consisting of:

```
                                       (SEQ ID NO. 1)
TTTTAATCAGAGGGTGAGGGTGAT;

(SEQ ID No. 2)
GCTTCTCAATGTTGGAGGATACA;

(SEQ ID No. 3)
GTCAAGATTGAGGAGGAAGAAGC;

(SEQ ID No. 4)
TTCATAGATGGCTATGCCTCGG;

(SEQ ID No. 5)
GGTGTTTCCCCACTAGCCA;

(SEQ ID No. 6)
CCCAGAGAGTGTATTGGCCC;

(SEQ ID No. 7)
TGCTATGTGGCCTTGGACAGATCACC;

(SEQ ID No. 8)
AGTTTAAAGATCTCAGAGAGAGCCGAGGCA;

(SEQ ID No. 9)
CCTTAGCGTATCACATGTGGACATGGACA;
``` and combinations thereof.

11. The method of claim 1, wherein said determining step has a sensitivity of no less than 85% and a specificity of no less than 85% in detecting a copy number amplification of a region specific to human chromosome 1q21.3.

* * * * *

SEQUENCE LISTING

<160> NUMBER OF SEQ ID NOS: 19

<210> SEQ ID NO 1
<211> LENGTH: 24
<212> TYPE: DNA
<213> ORGANISM: Artificial Sequence
<220> FEATURE:
<223> OTHER INFORMATION: primer

<400> SEQUENCE: 1

-continued ttttaatcag agggtgaggg tgat                                      24

<210> SEQ ID NO 2
<211> LENGTH: 23
<212> TYPE: DNA
<213> ORGANISM: Artificial Sequence
<220> FEATURE:
<223> OTHER INFORMATION: primer

<400> SEQUENCE: 2
gcttctcaat gttggaggat aca                                       23

<210> SEQ ID NO 3
<211> LENGTH: 23
<212> TYPE: DNA
<213> ORGANISM: Artificial Sequence
<220> FEATURE:
<223> OTHER INFORMATION: primer

<400> SEQUENCE: 3
gtcaagattg aggaggaaga agc                                       23

<210> SEQ ID NO 4
<211> LENGTH: 22
<212> TYPE: DNA
<213> ORGANISM: Artificial Sequence
<220> FEATURE:
<223> OTHER INFORMATION: primer

<400> SEQUENCE: 4
ttcatagatg gctatgcctc gg                                        22

<210> SEQ ID NO 5
<211> LENGTH: 19
<212> TYPE: DNA
<213> ORGANISM: Artificial Sequence
<220> FEATURE:
<223> OTHER INFORMATION: primer

<400> SEQUENCE: 5
ggtgtttccc cactagcca                                            19

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
cccagagagt gtattggccc                                           20

<210> SEQ ID NO 7
<211> LENGTH: 26
<212> TYPE: DNA
<213> ORGANISM: Artificial Sequence
<220> FEATURE:
<223> OTHER INFORMATION: probe

<400> SEQUENCE: 7
tgctatgtgg ccttggacag atcacc                                    26

<210> SEQ ID NO 8
<211> LENGTH: 30
<212> TYPE: DNA

```
<213> ORGANISM: Artificial Sequence
<220> FEATURE:
<223> OTHER INFORMATION: probe

<400> SEQUENCE: 8
agtttaaaga tctcagagag agccgaggca                                          30

<210> SEQ ID NO 9
<211> LENGTH: 29
<212> TYPE: DNA
<213> ORGANISM: Artificial Sequence
<220> FEATURE:
<223> OTHER INFORMATION: probe

<400> SEQUENCE: 9
ccttagcgta tcacatgtgg acatggaca                                           29

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
gttagagagt ctccaggccc                                                     20

<210> SEQ ID NO 11
<211> LENGTH: 21
<212> TYPE: DNA
<213> ORGANISM: Artificial Sequence
<220> FEATURE:
<223> OTHER INFORMATION: primer

<400> SEQUENCE: 11
actgtaatcc agcaaaagcg g                                                   21

<210> SEQ ID NO 12
<211> LENGTH: 30
<212> TYPE: DNA
<213> ORGANISM: Artificial Sequence
<220> FEATURE:
<223> OTHER INFORMATION: probe

<400> SEQUENCE: 12
tgtccacaga ctttctcaaa agatagggcc                                          30

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
cagcgctgaa taaacggcaa                                                     20

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
tcagggctct tcaccaaacc                                                     20
```

```
<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
ggggaacttc cataccagca                                               20

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
cactccctgg ctaaggaacc                                               20

<210> SEQ ID NO 17
<211> LENGTH: 52
<212> TYPE: DNA
<213> ORGANISM: Artificial Sequence
<220> FEATURE:
<223> OTHER INFORMATION: shRNA oligonucleotides

<400> SEQUENCE: 17
aaaagccgat gtctttgaga aaattggatc caattttctc aaagacatcg gc           52

<210> SEQ ID NO 18
<211> LENGTH: 52
<212> TYPE: DNA
<213> ORGANISM: Artificial Sequence
<220> FEATURE:
<223> OTHER INFORMATION: shRNA oligonucleotides

<400> SEQUENCE: 18
aaaagggatg acctgaagaa attttggatc caaaatttct tcaggtcatc cc           52

<210> SEQ ID NO 19
<211> LENGTH: 52
<212> TYPE: DNA
<213> ORGANISM: Artificial Sequence
<220> FEATURE:
<223> OTHER INFORMATION: shRNA oligonucleotides

<400> SEQUENCE: 19
aaaagcaaca tagagaccat catttggatc caaatgatgg tctctatgtt gc           52
```